US009205001B2

(12) United States Patent
Blott et al.

(10) Patent No.: US 9,205,001 B2
(45) Date of Patent: Dec. 8, 2015

(54) APPARATUS FOR ASPIRATING, IRRIGATING AND CLEANSING WOUNDS

(71) Applicant: SMITH & NEPHEW PLC, London (GB)

(72) Inventors: Patrick Lewis Blott, York (GB); Bryan Greener, York (GB); Edward Yerbury Hartwell, Hull (GB); Tina Michelle Walker, York (GB); Derek Nicolini, Brough (GB); Julian Lee-Webb, York (GB)

(73) Assignee: Smith & Nephew PLC, London (GB)

( * ) Notice: Subject to any disclaimer, the term of this patent is extended or adjusted under 35 U.S.C. 154(b) by 0 days.

(21) Appl. No.: 14/485,633

(22) Filed: Sep. 12, 2014

(65) Prior Publication Data

US 2015/0080787 A1    Mar. 19, 2015

Related U.S. Application Data

(60) Continuation of application No. 13/363,320, filed on Jan. 31, 2012, now Pat. No. 8,834,451, which is a division of application No. 12/416,829, filed on Apr. 1, 2009, now Pat. No. 8,398,614, which is a continuation of application No. 10/533,275, filed as application No. PCT/GB03/04647 on Oct. 28, 2003, now Pat. No. 7,524,315.

(30) Foreign Application Priority Data

Oct. 28, 2002   (GB) .................................. 0224986.0

(51) Int. Cl.
*A61M 27/00* (2006.01)
*A61F 13/00* (2006.01)
(Continued)

(52) U.S. Cl.
CPC ..... *A61F 13/00068* (2013.01); *A61F 13/00063* (2013.01); *A61M 1/0058* (2013.01);
(Continued)

(58) Field of Classification Search
CPC ............ A61M 1/0058; A61M 1/0088; A61M 1/0094; A61M 3/0229; A61F 13/00068; A61F 13/00062
USPC ........... 604/19, 289–290, 304–308, 543, 317, 604/327, 319–323
See application file for complete search history.

(56) References Cited

U.S. PATENT DOCUMENTS 765,746 A    7/1904  Miner
846,674 A    7/1907  Funk
(Continued)

FOREIGN PATENT DOCUMENTS

CA    2 369 022    10/2001
CA    2 369 024    10/2001
(Continued)

OTHER PUBLICATIONS

U.S. Appl. No. 14/496,305, filed Sep. 25, 2014, Blott et al.
(Continued)

*Primary Examiner* — Michele M Kidwell
(74) *Attorney, Agent, or Firm* — Knobbe, Martens, Olson & Bear, LLP

(57) ABSTRACT

An apparatus for cleansing wounds in which irrigant fluid from a reservoir connected to a conformable wound dressing and wound exudate from the dressing are recirculated by a device for moving fluid through a flow path which passes through the dressing and a means for fluid cleansing and back to the dressing. The cleansing means (which may be a single-phase, e.g. microfiltration, system or a two-phase, e.g. dialytic system) removes materials deleterious to wound healing, and the cleansed fluid, still containing materials that are beneficial in promoting wound healing, is returned to the wound bed. The dressing and a method of treatment using the apparatus.

20 Claims, 22 Drawing Sheets

(51) Int. Cl.
*A61M 1/00* (2006.01)
*A61M 3/02* (2006.01)

(52) U.S. Cl.
CPC ........... *A61M1/0084* (2013.01); *A61M 1/0088* (2013.01); *A61M 1/0094* (2014.02); *A61M 3/0229* (2013.01); *A61M 27/00* (2013.01); *A61F 2013/0054* (2013.01); *A61F 2013/00174* (2013.01); *A61F 2013/00221* (2013.01); *A61F 2013/00536* (2013.01); *A61F 2013/00927* (2013.01)

(56) References Cited

U.S. PATENT DOCUMENTS

| | | |
|---|---|---|
| 1,066,934 A | 7/1913 | Manney |
| 1,355,679 A | 10/1920 | McConnell |
| 1,355,846 A | 10/1920 | Rannells |
| 1,385,346 A | 7/1921 | Taylor |
| 1,480,562 A | 1/1924 | Mock |
| 1,585,104 A | 5/1926 | Montgomery |
| 1,732,310 A | 10/1929 | Naibebt et al. |
| 1,863,534 A | 6/1932 | Odell |
| 1,936,129 A | 11/1933 | Fisk et al. |
| 2,195,771 A | 4/1940 | Estler |
| 2,232,254 A | 2/1941 | Morqan |
| 2,280,915 A | 4/1942 | Johnson |
| 2,318,888 A | 5/1943 | Sanders |
| 2,367,690 A | 7/1943 | Purdy |
| 2,338,339 A | 1/1944 | la Mere et al. |
| 2,366,799 A | 1/1945 | Luisada |
| 2,385,683 A | 9/1945 | Burton et al. |
| 2,547,758 A | 4/1951 | Keeling |
| 2,568,933 A | 9/1951 | Robbins |
| 2,632,443 A | 3/1953 | Lesher |
| 2,682,873 A | 7/1954 | Evans et al. |
| 2,910,763 A | 8/1955 | Lauterbach |
| 2,969,057 A | 1/1961 | Simmons |
| 3,026,526 A | 3/1962 | Montrose |
| 3,026,874 A | 3/1962 | Stevens et al. |
| 3,115,138 A | 12/1963 | McElvenny et al. |
| 3,217,707 A | 11/1965 | Werding |
| 3,238,937 A | 3/1966 | Stein |
| 3,286,711 A | 11/1966 | MacLeod |
| 3,288,140 A | 11/1966 | McCarthy |
| 3,315,665 A | 4/1967 | MacLeod |
| 3,367,332 A | 2/1968 | Groves |
| 3,465,748 A | 9/1969 | Kravchenko |
| 3,478,736 A | 11/1969 | Roberts et al. |
| 3,486,504 A | 12/1969 | Austin, Jr. |
| 3,572,340 A | 3/1971 | Lloyd et al. |
| 3,610,238 A | 10/1971 | Rich, Jr. |
| 3,624,821 A | 11/1971 | Henderson |
| 3,682,180 A | 8/1972 | McFarlane |
| 3,712,298 A | 1/1973 | Snowdon et al. |
| 3,763,857 A | 10/1973 | Schrading et al. |
| 3,783,870 A | 1/1974 | Schachet |
| 3,794,035 A | 2/1974 | Brenner et al. |
| 3,826,254 A | 7/1974 | Mellor |
| 3,859,989 A | 1/1975 | Spielberg |
| 3,871,377 A | 3/1975 | Treace et al. |
| 3,874,387 A | 4/1975 | Barbieri |
| 3,896,810 A | 7/1975 | Akiyama |
| 3,908,642 A | 9/1975 | Vinmont et al. |
| 3,908,664 A | 9/1975 | Loseff |
| 3,954,105 A | 5/1976 | Nordby et al. |
| 3,961,625 A | 6/1976 | Dillon |
| 3,988,793 A | 11/1976 | Abitbol |
| 3,993,080 A | 11/1976 | Loseff |
| RE29,319 E | 7/1977 | Nordby et al. |
| 4,073,294 A | 2/1978 | Stanley et al. |
| 4,080,970 A | 3/1978 | Miller |
| 4,102,342 A | 7/1978 | Akiyama et al. |
| 4,112,947 A | 9/1978 | Nehring |
| 4,117,551 A | 9/1978 | Books et al. |
| 4,136,696 A | 1/1979 | Nehring |
| 4,149,541 A | 4/1979 | Gammons et al. |
| 4,169,563 A | 10/1979 | Leu |
| 4,172,455 A | 10/1979 | Beaussant |
| 4,178,938 A | 12/1979 | Au |
| 4,180,074 A | 12/1979 | Murry et al. |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,228,798 A | 10/1980 | Deaton |
| 4,250,882 A | 2/1981 | Adair |
| 4,252,119 A | 2/1981 | Coates |
| 4,261,363 A | 4/1981 | Russo |
| 4,266,545 A | 5/1981 | Moss |
| 4,275,721 A | 6/1981 | Olson |
| 4,278,089 A | 7/1981 | Huck et al. |
| 4,297,995 A | 11/1981 | Golub |
| 4,316,466 A | 2/1982 | Babb |
| 4,341,207 A | 7/1982 | Steer et al. |
| 4,360,015 A | 11/1982 | Mayer |
| 4,360,021 A | 11/1982 | Stima |
| 4,373,519 A | 2/1983 | Errede et al. |
| 4,382,441 A | 5/1983 | Svedman |
| 4,392,853 A | 7/1983 | Muto |
| 4,392,860 A | 7/1983 | Huck et al. |
| 4,418,691 A | 12/1983 | Yannas et al. |
| 4,419,097 A | 12/1983 | Rowland |
| 4,421,109 A | 12/1983 | Thornton |
| 4,432,354 A | 2/1984 | Lasley |
| 4,465,485 A | 8/1984 | Kashmer et al. |
| 4,469,092 A | 9/1984 | Marshall et al. |
| 4,475,909 A | 10/1984 | Eisenberg |
| 4,480,638 A | 11/1984 | Schmid |
| 4,499,896 A | 2/1985 | Heinecke |
| 4,525,166 A | 6/1985 | Leclerc |
| 4,527,064 A | 7/1985 | Anderson |
| 4,529,402 A | 7/1985 | Weilbacher et al. |
| 4,534,356 A | 8/1985 | Papadakis |
| 4,538,920 A | 9/1985 | Drake et al. |
| 4,540,412 A | 9/1985 | Van Overloop |
| 4,543,100 A | 9/1985 | Brodsky |
| 4,551,141 A | 11/1985 | McNeil |
| 4,561,435 A | 12/1985 | McKnight et al. |
| 4,569,674 A | 2/1986 | Phillips |
| 4,573,965 A | 3/1986 | Russo |
| 4,578,060 A | 3/1986 | Huck et al. |
| 4,587,101 A | 5/1986 | Marsoner et al. |
| 4,605,399 A | 8/1986 | Weston et al. |
| 4,608,041 A | 8/1986 | Nielsen |
| 4,624,656 A | 11/1986 | Clark et al. |
| 4,640,688 A | 2/1987 | Hauser |
| 4,655,202 A | 4/1987 | Potter et al. |
| 4,655,754 A | 4/1987 | Richmond et al. |
| 4,655,766 A | 4/1987 | Theeuwes et al. |
| 4,661,093 A | 4/1987 | Beck et al. |
| 4,664,662 A | 5/1987 | Webster |
| 4,699,134 A | 10/1987 | Samuelsen |
| 4,710,165 A | 12/1987 | McNeil et al. |
| 4,713,052 A | 12/1987 | Beck et al. |
| 4,738,249 A | 4/1988 | Linman |
| 4,740,202 A | 4/1988 | Stacey |
| 4,743,232 A | 5/1988 | Kruger |
| 4,753,536 A | 6/1988 | Spehar et al. |
| 4,759,354 A | 7/1988 | Quarfoot |
| 4,764,167 A | 8/1988 | Tu |
| 4,765,316 A | 8/1988 | Marshall |
| 4,767,026 A | 8/1988 | Keller |
| 4,771,919 A | 9/1988 | Ernst |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,798,583 A | 1/1989 | Beck et al. |
| 4,798,603 A | 1/1989 | Meyer et al. |
| 4,817,594 A | 4/1989 | Juhasz |
| 4,820,265 A | 4/1989 | DeSatnick et al. |
| 4,820,284 A | 4/1989 | Hauri |
| 4,826,494 A | 5/1989 | Richmond et al. |

(56) References Cited

U.S. PATENT DOCUMENTS

| | | |
|---|---|---|
| 4,828,546 A | 5/1989 | McNeil et al. |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg et al. |
| 4,851,545 A | 7/1989 | Song et al. |
| 4,863,449 A | 9/1989 | Therriault et al. |
| 4,867,150 A | 9/1989 | Gilbert |
| 4,872,450 A | 10/1989 | Austad |
| 4,875,473 A | 10/1989 | Alvarez |
| 4,878,901 A | 11/1989 | Sachse |
| 4,882,213 A | 11/1989 | Gaddis et al. |
| 4,902,277 A | 2/1990 | Marhies et al. |
| 4,906,233 A | 3/1990 | Moriuchi et al. |
| 4,917,112 A | 4/1990 | Kalt |
| 4,921,488 A | 5/1990 | Maitz et al. |
| 4,921,492 A | 5/1990 | Schultz |
| 4,923,444 A | 5/1990 | Daoud et al. |
| 4,925,447 A | 5/1990 | Rosenblatt |
| 4,929,477 A | 5/1990 | Will |
| 4,931,519 A | 6/1990 | Song et al. |
| 4,936,834 A | 6/1990 | Beck et al. |
| 4,941,882 A | 7/1990 | Ward et al. |
| 4,950,483 A | 8/1990 | Ksander et al. |
| 4,953,565 A | 9/1990 | Tachibana et al. |
| 4,955,893 A | 9/1990 | Yannas et al. |
| 4,969,880 A | 11/1990 | Zamierowski |
| 4,969,881 A | 11/1990 | Viesturs |
| 4,972,829 A | 11/1990 | Knerr |
| 4,979,944 A | 12/1990 | Luzsicza |
| 4,997,425 A | 3/1991 | Shioya et al. |
| 5,000,164 A | 3/1991 | Cooper |
| 5,009,635 A | 4/1991 | Scarberry |
| 5,030,202 A | 7/1991 | Harris |
| 5,034,006 A | 7/1991 | Hosoda et al. |
| 5,035,884 A | 7/1991 | Song et al. |
| 5,055,198 A | 10/1991 | Shettigar |
| 5,056,510 A | 10/1991 | Gilman |
| 5,064,653 A | 11/1991 | Sessions et al. |
| 5,073,172 A | 12/1991 | Fell |
| 5,080,493 A | 1/1992 | McKown et al. |
| 5,080,661 A | 1/1992 | Lavender et al. |
| 5,086,764 A | 2/1992 | Gilman |
| 5,088,483 A | 2/1992 | Heinecke |
| 5,089,606 A | 2/1992 | Cole et al. |
| 5,100,395 A | 3/1992 | Rosenberg |
| 5,100,396 A | 3/1992 | Zamierowski |
| 5,106,362 A | 4/1992 | Gilman |
| 5,112,323 A | 5/1992 | Winkler et al. |
| 5,113,871 A | 5/1992 | Viljanto et al. |
| 5,134,994 A | 8/1992 | Say |
| 5,141,503 A | 8/1992 | Sewell, Jr. |
| 5,149,331 A | 9/1992 | Ferdman et al. |
| 5,152,757 A | 10/1992 | Eriksson |
| 5,160,315 A | 11/1992 | Heinecke et al. |
| 5,167,613 A | 12/1992 | Karami et al. |
| 5,176,663 A | 1/1993 | Svedman et al. |
| 5,184,077 A | 2/1993 | Day et al. |
| 5,201,780 A | 4/1993 | Dinsmoor et al. |
| 5,218,973 A | 6/1993 | Weaver et al. |
| 5,228,431 A | 7/1993 | Giarretto |
| 5,243,968 A | 9/1993 | Byun |
| 5,249,709 A | 10/1993 | Duckworth et al. |
| 5,261,893 A | 11/1993 | Zamierowski |
| 5,264,218 A | 11/1993 | Rogozinski |
| 5,266,928 A | 11/1993 | Johnson |
| 5,279,608 A | 1/1994 | Cherif Cheikh |
| 5,288,431 A | 2/1994 | Huber et al. |
| 5,307,791 A | 5/1994 | Senoue et al. |
| 5,322,695 A | 6/1994 | Shah et al. |
| 5,328,614 A | 7/1994 | Matsumura |
| 5,333,760 A | 8/1994 | Simmen et al. |
| 5,336,209 A | 8/1994 | Porzilli |
| 5,358,494 A | 10/1994 | Svedman |
| 5,360,398 A | 11/1994 | Grieshaber et al. |
| 5,362,543 A | 11/1994 | Nickerson |
| 5,380,280 A | 1/1995 | Peterson |
| 5,425,742 A | 6/1995 | Joy |
| 5,437,651 A | 8/1995 | Todd et al. |
| 5,445,604 A | 8/1995 | Lang |
| 5,462,514 A | 10/1995 | Harris |
| 5,466,229 A | 11/1995 | Elson |
| 5,486,158 A | 1/1996 | Samuelson |
| 5,487,889 A | 1/1996 | Eckert et al. |
| 5,489,280 A | 2/1996 | Russell |
| 5,489,304 A | 2/1996 | Orgill et al. |
| 5,496,605 A | 3/1996 | Augst et al. |
| 5,498,338 A | 3/1996 | Kruger et al. |
| 5,527,293 A | 6/1996 | Zamierowski |
| 5,527,923 A | 6/1996 | Klingler et al. |
| 5,531,855 A | 7/1996 | Heinecke et al. |
| 5,549,584 A | 8/1996 | Gross |
| 5,549,585 A | 8/1996 | Maher et al. |
| 5,577,994 A | 11/1996 | Celik |
| 5,582,596 A | 12/1996 | Fukunaga et al. |
| 5,593,395 A | 1/1997 | Martz |
| 5,599,289 A | 2/1997 | Castellana |
| 5,609,271 A | 3/1997 | Keller et al. |
| 5,616,387 A | 4/1997 | Augst et al. |
| 5,618,556 A | 4/1997 | Johns et al. |
| 5,624,423 A | 4/1997 | Anjur et al. |
| 5,633,007 A | 5/1997 | Webb et al. |
| 5,636,643 A | 6/1997 | Argenta et al. |
| 5,643,189 A | 7/1997 | Masini |
| 5,645,081 A | 7/1997 | Argenta et al. |
| 5,645,981 A | 7/1997 | Romanet et al. |
| 5,676,650 A | 10/1997 | Grieshaber et al. |
| 5,681,579 A | 10/1997 | Freeman |
| 5,688,225 A | 11/1997 | Walker |
| 5,701,917 A | 12/1997 | Khouri |
| 5,713,881 A | 2/1998 | Rezai et al. |
| 5,714,225 A | 2/1998 | Hansen et al. |
| 5,716,411 A | 2/1998 | Orgill et al. |
| 5,733,305 A | 3/1998 | Fleischmann |
| 5,759,570 A | 6/1998 | Arnold |
| 5,785,688 A | 7/1998 | Joshi et al. |
| 5,792,090 A | 8/1998 | Ladin |
| 5,810,755 A | 9/1998 | LeVeen et al. |
| 5,827,246 A | 10/1998 | Bowen |
| 5,830,176 A | 11/1998 | Mackool |
| 5,830,496 A | 11/1998 | Freeman |
| 5,833,646 A | 11/1998 | Masini |
| 5,840,777 A | 11/1998 | Eagles et al. |
| 5,868,933 A | 2/1999 | Patrick et al. |
| 5,885,237 A | 3/1999 | Kadash et al. |
| 5,893,368 A | 4/1999 | Sugerman |
| 5,899,893 A | 5/1999 | Dyer et al. |
| 5,904,659 A | 5/1999 | Duarte |
| 5,938,626 A | 8/1999 | Sugerman |
| 5,941,859 A | 8/1999 | Lerman |
| 5,944,703 A | 8/1999 | Dixon et al. |
| 5,954,680 A | 9/1999 | Augustine |
| 5,958,420 A | 9/1999 | Jenson |
| 5,964,723 A | 10/1999 | Augustine |
| 5,970,266 A | 10/1999 | Takato |
| 5,981,822 A | 11/1999 | Addison |
| 5,985,990 A | 11/1999 | Kantner et al. |
| 6,045,541 A | 4/2000 | Matsumoto et al. |
| 6,071,267 A | 6/2000 | Zamierowski |
| 6,087,549 A | 7/2000 | Flick |
| 6,110,197 A | 8/2000 | Augustine et al. |
| D430,674 S | 9/2000 | Dunshee et al. |
| 6,117,111 A | 9/2000 | Fleischmann |
| 6,117,444 A | 9/2000 | Orgill et al. |
| 6,135,116 A | 10/2000 | Vogel et al. |
| 6,135,166 A | 10/2000 | Paradies et al. |
| D434,150 S | 11/2000 | Tumey et al. |
| 6,142,982 A | 11/2000 | Hunt et al. |
| 6,168,800 B1 | 1/2001 | Dobos et al. |
| 6,176,307 B1 | 1/2001 | Danos et al. |
| D439,341 S | 3/2001 | Tumey et al. |
| 6,203,563 B1 | 3/2001 | Fernandez |
| 6,225,523 B1 | 5/2001 | Masini |

(56) References Cited

U.S. PATENT DOCUMENTS

| | | |
|---|---|---|
| 6,252,129 B1 | 6/2001 | Coffee |
| 6,254,567 B1 | 7/2001 | Treu et al. |
| 6,255,552 B1 | 7/2001 | Cummings et al. |
| 6,261,276 B1 | 7/2001 | Reitsma |
| 6,287,521 B1 | 9/2001 | Quay et al. |
| 6,291,050 B1 | 9/2001 | Cree et al. |
| 6,293,281 B1 | 9/2001 | Shultz et al. |
| 6,345,623 B1 | 2/2002 | Heaton et al. |
| 6,350,339 B1 | 2/2002 | Sessions |
| 6,368,311 B1 | 4/2002 | Valerio |
| 6,371,976 B1 | 4/2002 | Vrzalik |
| 6,391,294 B1 | 5/2002 | Dettmar et al. |
| 6,398,761 B1 | 6/2002 | Bills et al. |
| 6,398,767 B1 | 6/2002 | Fleischmann |
| 6,402,724 B1 | 6/2002 | Smith et al. |
| 6,450,773 B1 | 9/2002 | Upton |
| 6,458,109 B1 | 10/2002 | Henley et al. |
| 6,465,708 B1 | 10/2002 | Augustine |
| 6,471,685 B1 | 10/2002 | Johnson |
| 6,471,982 B1 | 10/2002 | Lydon et al. |
| 6,486,285 B2 | 11/2002 | Fujita |
| 6,491,684 B1 | 12/2002 | Joshi et al. |
| 6,520,982 B1 | 2/2003 | Boynton et al. |
| 6,527,203 B2 | 3/2003 | Hurray et al. |
| 6,536,056 B1 | 3/2003 | Vrzalik et al. |
| 6,553,998 B2 | 4/2003 | Heaton et al. |
| 6,564,972 B2 | 5/2003 | Sawhney et al. |
| 6,569,113 B2 | 5/2003 | Wirt et al. |
| 6,595,949 B1 | 7/2003 | Shapiro |
| 6,599,262 B1 | 7/2003 | Masini |
| 6,626,827 B1 | 9/2003 | Felix et al. |
| 6,626,891 B2 | 9/2003 | Ohmstede |
| 6,629,774 B1 | 10/2003 | Guruendeman |
| 6,648,862 B2 | 11/2003 | Watson |
| 6,673,028 B1 | 1/2004 | Argenta et al. |
| 6,676,610 B2 | 1/2004 | Morton et al. |
| 6,680,113 B1 | 1/2004 | Lucast et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,730,299 B1 | 5/2004 | Tayot et al. |
| 6,732,887 B2 | 5/2004 | Bills |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| 6,787,682 B2 | 9/2004 | Gilman |
| 6,794,554 B2 | 9/2004 | Sessions et al. |
| 6,797,855 B2 | 9/2004 | Worthley |
| 6,800,074 B2 | 10/2004 | Henley et al. |
| 6,814,079 B2 | 11/2004 | Heaton et al. |
| 6,820,766 B2 | 11/2004 | Keller et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,856,821 B2 | 2/2005 | Johnson |
| 6,936,037 B2 | 8/2005 | Bubb |
| 6,945,987 B2 | 9/2005 | Beard et al. |
| 6,951,553 B2 | 10/2005 | Bubb et al. |
| 6,974,428 B2 | 12/2005 | Knutson et al. |
| 6,977,323 B1 | 12/2005 | Swenson |
| 6,979,324 B2 | 12/2005 | Byordi et al. |
| 6,988,423 B2 | 1/2006 | Bolam et al. |
| 6,994,702 B1 | 2/2006 | Johnson |
| 7,004,915 B2 | 2/2006 | Boynton et al. |
| 7,005,556 B1 | 2/2006 | Becker et al. |
| 7,022,113 B2 | 4/2006 | Lockwood et al. |
| 7,030,288 B2 | 4/2006 | Liedtke et al. |
| 7,041,868 B2 | 5/2006 | Greene et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,735 B2 | 10/2006 | Weston |
| 7,137,968 B1 | 11/2006 | Burrell et al. |
| 7,144,390 B1 | 12/2006 | Hannigan et al. |
| 7,175,336 B2 | 2/2007 | Voellmicke et al. |
| 7,182,758 B2 | 2/2007 | McCraw |
| 7,195,624 B2 | 3/2007 | Lockwood |
| 7,198,046 B1 | 4/2007 | Argenta |
| 7,216,651 B2 | 5/2007 | Argenta et al. |
| 7,276,051 B1 | 10/2007 | Henley et al. |
| 7,291,762 B2 | 11/2007 | Flick |
| 7,335,809 B2 | 2/2008 | Riesinger |
| 7,338,482 B2 | 3/2008 | Lockwood et al. |
| 7,361,184 B2 | 4/2008 | Joshi |
| 7,381,859 B2 | 6/2008 | Hunt et al. |
| 7,470,830 B2 | 12/2008 | Sigurjonsson et al. |
| 7,494,482 B2 | 2/2009 | Orgill et al. |
| 7,507,870 B2 | 3/2009 | Nielsen et al. |
| 7,518,031 B2 | 4/2009 | Liedtke et al. |
| 7,524,315 B2 | 4/2009 | Blott et al. |
| 7,534,240 B1 | 5/2009 | Johnson |
| 7,534,927 B2 | 5/2009 | Lockwood et al. |
| 7,540,848 B2 | 6/2009 | Hannigan et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| 7,625,362 B2 | 12/2009 | Boehringer |
| 7,645,269 B2 | 1/2010 | Zamierowski |
| 7,674,837 B2 | 3/2010 | Gaserod et al. |
| 7,678,090 B2 | 3/2010 | Risk, Jr. |
| 7,699,823 B2 | 4/2010 | Haggstrom et al. |
| 7,699,830 B2 | 4/2010 | Martin |
| 7,708,724 B2 | 5/2010 | Weston |
| 7,722,582 B2 | 5/2010 | Lina et al. |
| 7,723,560 B2 | 5/2010 | Lockwood et al. |
| 7,731,702 B2 | 6/2010 | Byordi et al. |
| 7,745,681 B1 | 6/2010 | Ferguson |
| 7,753,894 B2 | 7/2010 | Blott et al. |
| 7,758,554 B2 | 7/2010 | Lina et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,815,616 B2 | 10/2010 | Boehringer et al. |
| 7,828,782 B2 | 11/2010 | Suzuki |
| 7,846,141 B2 | 12/2010 | Weston |
| 7,883,494 B2 | 2/2011 | Martin |
| 7,896,856 B2 | 3/2011 | Petrosenko et al. |
| 7,909,805 B2 | 3/2011 | Weston |
| 7,927,318 B2 | 4/2011 | Risk, Jr. et al. |
| 7,964,766 B2 | 6/2011 | Blott et al. |
| D642,594 S | 8/2011 | Mattson et al. |
| 7,998,125 B2 | 8/2011 | Weston |
| 8,062,272 B2 | 11/2011 | Weston |
| 8,062,273 B2 | 11/2011 | Weston |
| 8,080,702 B2 | 12/2011 | Blott et al. |
| 8,096,979 B2 | 1/2012 | Lina et al. |
| 8,100,887 B2 | 1/2012 | Weston et al. |
| 8,105,295 B2 | 1/2012 | Blott et al. |
| 8,118,794 B2 | 2/2012 | Weston et al. |
| 8,128,615 B2 | 3/2012 | Blott et al. |
| 8,162,907 B2 | 4/2012 | Heagle |
| 8,162,909 B2 | 4/2012 | Blott et al. |
| 8,168,848 B2 | 5/2012 | Lockwood et al. |
| 8,192,409 B2 | 6/2012 | Hardman et al. |
| 8,235,955 B2 | 8/2012 | Blott et al. |
| 8,241,261 B2 | 8/2012 | Randolph et al. |
| 8,257,327 B2 | 9/2012 | Blott et al. |
| 8,282,611 B2 | 10/2012 | Weston |
| 8,303,552 B2 | 11/2012 | Weston |
| 8,338,402 B2 | 12/2012 | Fry et al. |
| 8,348,910 B2 | 1/2013 | Blott et al. |
| 8,366,692 B2 | 2/2013 | Weston |
| 8,372,049 B2 | 2/2013 | Jaeb et al. |
| 8,372,050 B2 | 2/2013 | Jaeb et al. |
| 8,398,614 B2 | 3/2013 | Blott et al. |

(56) References Cited

U.S. PATENT DOCUMENTS

| | | | |
|---|---|---|---|
| 8,399,730 | B2 | 3/2013 | Kazala, Jr. et al. |
| D679,819 | S | 4/2013 | Peron |
| D679,820 | S | 4/2013 | Peron |
| 8,449,509 | B2 | 5/2013 | Weston |
| 8,529,548 | B2 | 9/2013 | Blott et al. |
| 8,535,296 | B2 | 9/2013 | Blott et al. |
| 8,540,699 | B2 | 9/2013 | Miller et al. |
| D692,565 | S | 10/2013 | Lattimore et al. |
| 8,551,061 | B2 | 10/2013 | Hartwell |
| 8,569,566 | B2 | 10/2013 | Blott et al. |
| 8,613,734 | B2 | 12/2013 | Lina et al. |
| 8,680,360 | B2 | 3/2014 | Greener et al. |
| 8,715,256 | B2 | 5/2014 | Greener |
| 8,758,313 | B2 | 6/2014 | Blott et al. |
| 8,791,315 | B2 | 7/2014 | Lattimore et al. |
| 8,834,451 | B2 | 9/2014 | Blott et al. |
| 8,845,619 | B2 | 9/2014 | Blott et al. |
| 8,882,746 | B2 | 11/2014 | Blott et al. |
| 8,926,592 | B2 | 1/2015 | Blott et al. |
| 2001/0004082 | A1 | 6/2001 | Keller et al. |
| 2001/0027285 | A1 | 10/2001 | Heinecke et al. |
| 2001/0029956 | A1 | 10/2001 | Argenta |
| 2001/0034499 | A1 | 10/2001 | Sessions et al. |
| 2001/0043943 | A1 | 11/2001 | Coffey |
| 2002/0002209 | A1 | 1/2002 | Mork |
| 2002/0038826 | A1 | 4/2002 | Hurray et al. |
| 2002/0068913 | A1 | 6/2002 | Fleischmann |
| 2002/0082567 | A1 | 6/2002 | Lockwood et al. |
| 2002/0114847 | A1 | 8/2002 | Peshoff |
| 2002/0143286 | A1 | 10/2002 | Tumey |
| 2002/0145007 | A1 | 10/2002 | Sawhney et al. |
| 2002/0161346 | A1 | 10/2002 | Lockwood et al. |
| 2002/0183702 | A1 | 12/2002 | Henley et al. |
| 2002/0198490 | A1 | 12/2002 | Wirt et al. |
| 2003/0014025 | A1 | 1/2003 | Allen et al. |
| 2003/0021775 | A1 | 1/2003 | Freeman |
| 2003/0040687 | A1 | 2/2003 | Boynton et al. |
| 2003/0093041 | A1 | 5/2003 | Risk, Jr. et al. |
| 2003/0125646 | A1 | 7/2003 | Whitlock |
| 2003/0134332 | A1 | 7/2003 | Boykin |
| 2003/0144619 | A1 | 7/2003 | Augustine |
| 2003/0148959 | A1 | 8/2003 | Quirk et al. |
| 2003/0171675 | A1 | 9/2003 | Rosenberg |
| 2003/0175798 | A1 | 9/2003 | Raees et al. |
| 2003/0183653 | A1 | 10/2003 | Bills |
| 2003/0212357 | A1 | 11/2003 | Pace |
| 2003/0212431 | A1 | 11/2003 | Brady et al. |
| 2003/0219469 | A1 | 11/2003 | Johnson et al. |
| 2003/0225347 | A1 | 12/2003 | Argenta et al. |
| 2004/0006319 | A1 | 1/2004 | Lina et al. |
| 2004/0019342 | A1 | 1/2004 | Nagasuna et al. |
| 2004/0030304 | A1 | 2/2004 | Hunt et al. |
| 2004/0033466 | A1 | 2/2004 | Shellard et al. |
| 2004/0039391 | A1 | 2/2004 | Argenta et al. |
| 2004/0050411 | A1 | 3/2004 | Lawrence |
| 2004/0054338 | A1 | 3/2004 | Bybordi et al. |
| 2004/0064111 | A1 | 4/2004 | Lockwood et al. |
| 2004/0064132 | A1 | 4/2004 | Boehringer et al. |
| 2004/0121438 | A1 | 6/2004 | Quirk |
| 2004/0122434 | A1 | 6/2004 | Argenta et al. |
| 2004/0127862 | A1 | 7/2004 | Bubb et al. |
| 2004/0127863 | A1 | 7/2004 | Bubb et al. |
| 2004/0162512 | A1 | 8/2004 | Liedtke et al. |
| 2004/0167617 | A1 | 8/2004 | Voellmicke et al. |
| 2004/0171998 | A1 | 9/2004 | Marasco, Jr. |
| 2005/0010153 | A1* | 1/2005 | Lockwood et al. ............ 602/41 |
| 2005/0020955 | A1 | 1/2005 | Sanders et al. |
| 2005/0090787 | A1 | 4/2005 | Risk et al. |
| 2005/0113733 | A1 | 5/2005 | Liedtke et al. |
| 2005/0130299 | A1 | 6/2005 | Suzuki |
| 2005/0131327 | A1 | 6/2005 | Lockwood et al. |
| 2005/0137272 | A1 | 6/2005 | Gaserod et al. |
| 2005/0143697 | A1 | 6/2005 | Riesinger |
| 2005/0163904 | A1 | 7/2005 | Walker et al. |
| 2005/0177190 | A1 | 8/2005 | Zamierowski |
| 2005/0181163 | A1 | 8/2005 | Kose |
| 2005/0230422 | A1 | 10/2005 | Muller et al. |
| 2006/0009744 | A1 | 1/2006 | Erdman et al. |
| 2006/0029675 | A1 | 2/2006 | Ginther |
| 2006/0142687 | A1 | 6/2006 | Liedtke et al. |
| 2006/0173253 | A1 | 8/2006 | Ganapathy et al. |
| 2006/0178608 | A1 | 8/2006 | Stapf |
| 2006/0241689 | A1 | 10/2006 | Leiboff et al. |
| 2006/0273109 | A1 | 12/2006 | Keller |
| 2007/0014837 | A1 | 1/2007 | Johnson et al. |
| 2007/0038172 | A1 | 2/2007 | Zamierowski |
| 2007/0055209 | A1 | 3/2007 | Patel et al. |
| 2007/0073200 | A1 | 3/2007 | Hannigan et al. |
| 2007/0142761 | A1 | 6/2007 | Aali |
| 2007/0167927 | A1 | 7/2007 | Hunt et al. |
| 2007/0219497 | A1 | 9/2007 | Johnson et al. |
| 2007/0219513 | A1 | 9/2007 | Lina et al. |
| 2007/0233022 | A1 | 10/2007 | Henley et al. |
| 2007/0237811 | A1 | 10/2007 | Scherr |
| 2007/0239139 | A1 | 10/2007 | Weston |
| 2007/0292488 | A1 | 12/2007 | Bassiri et al. |
| 2008/0069855 | A1 | 3/2008 | Bonutti |
| 2008/0082059 | A1 | 4/2008 | Fink et al. |
| 2008/0095979 | A1 | 4/2008 | Hatanaka et al. |
| 2008/0213344 | A1 | 9/2008 | McCarthy et al. |
| 2008/0243044 | A1 | 10/2008 | Hunt et al. |
| 2009/0054855 | A1 | 2/2009 | Blott et al. |
| 2009/0099519 | A1 | 4/2009 | Kaplan |
| 2009/0105671 | A1 | 4/2009 | Daggar et al. |
| 2009/0130186 | A1 | 5/2009 | McCarthy et al. |
| 2009/0177136 | A1 | 7/2009 | Liedtke et al. |
| 2009/0192499 | A1 | 7/2009 | Weston et al. |
| 2009/0221977 | A1 | 9/2009 | Blott et al. |
| 2009/0227969 | A1 | 9/2009 | Jaeb et al. |
| 2009/0234306 | A1 | 9/2009 | Vitaris |
| 2009/0234309 | A1 | 9/2009 | Vitaris et al. |
| 2009/0240185 | A1 | 9/2009 | Jaeb et al. |
| 2009/0275872 | A1 | 11/2009 | Addison et al. |
| 2009/0299251 | A1 | 12/2009 | Buan |
| 2009/0299255 | A1 | 12/2009 | Kazala, Jr. et al. |
| 2009/0299306 | A1 | 12/2009 | Buan |
| 2009/0306580 | A1 | 12/2009 | Blott et al. |
| 2009/0312723 | A1 | 12/2009 | Blott et al. |
| 2010/0022972 | A1 | 1/2010 | Lina et al. |
| 2010/0036367 | A1 | 2/2010 | Krohn |
| 2010/0069829 | A1 | 3/2010 | Hutchinson et al. |
| 2010/0069858 | A1 | 3/2010 | Olson |
| 2010/0069885 | A1 | 3/2010 | Stevenson et al. |
| 2010/0106114 | A1 | 4/2010 | Weston et al. |
| 2010/0106117 | A1 | 4/2010 | Lockwood et al. |
| 2010/0125258 | A1 | 5/2010 | Coulthard et al. |
| 2010/0135915 | A1 | 6/2010 | Greener et al. |
| 2010/0160880 | A1 | 6/2010 | Weston |
| 2010/0211030 | A1 | 8/2010 | Turner et al. |
| 2010/0249733 | A9 | 9/2010 | Blott |
| 2010/0268198 | A1 | 10/2010 | Buan et al. |
| 2010/0305526 | A1 | 12/2010 | Robinson et al. |
| 2010/0324510 | A1 | 12/2010 | Andresen et al. |
| 2011/0004171 | A1 | 1/2011 | Blott et al. |
| 2011/0028918 | A1 | 2/2011 | Hartwell |
| 2011/0054423 | A1 | 3/2011 | Blott et al. |
| 2011/0087178 | A2 | 4/2011 | Weston |
| 2011/0118683 | A1 | 5/2011 | Weston |
| 2011/0172612 | A1 | 7/2011 | Greener |
| 2011/0178451 | A1 | 7/2011 | Robinson et al. |
| 2011/0224631 | A1 | 9/2011 | Simmons et al. |
| 2011/0282309 | A1 | 11/2011 | Adie et al. |
| 2012/0004628 | A1 | 1/2012 | Blott et al. |
| 2012/0041399 | A1 | 2/2012 | Blott et al. |
| 2012/0053538 | A1 | 3/2012 | Blott et al. |
| 2012/0083755 | A1 | 4/2012 | Lina et al. |
| 2012/0123356 | A1 | 5/2012 | Greener |
| 2012/0157942 | A1 | 6/2012 | Weston |
| 2013/0096519 | A1 | 4/2013 | Blott et al. |
| 2013/0116635 | A1 | 5/2013 | Fleischmann |

(56) References Cited

U.S. PATENT DOCUMENTS

2014/0094761 A1 4/2014 Corley
2014/0371691 A1 12/2014 Blott et al.

FOREIGN PATENT DOCUMENTS

| | | |
|---|---|---|
| DE | 847475 | 8/1952 |
| DE | 2 809 828 | 9/1978 |
| DE | 3 032 092 | 8/1980 |
| DE | 3 137 839 | 3/1983 |
| DE | 3 539 533 | 5/1987 |
| DE | 3 935 818 | 5/1991 |
| DE | 4 012 232 | 10/1991 |
| DE | 4 016 034 | 11/1991 |
| DE | 4 102 684 | 8/1992 |
| DE | 2 961 8426 | 2/1997 |
| DE | 198 44 355 | 4/2000 |
| EP | 0 020 662 | 7/1984 |
| EP | 0 099 748 | 5/1987 |
| EP | 0 122 085 | 6/1987 |
| EP | 0 355 186 | 2/1990 |
| EP | 0 355 536 | 2/1990 |
| EP | 0 418 607 | 3/1991 |
| EP | 0 485 657 | 5/1992 |
| EP | 0 521 434 | 7/1993 |
| EP | 0 617 938 | 3/1994 |
| EP | 0 425 164 | 9/1994 |
| EP | 0 619 105 | 10/1994 |
| EP | 0 638 301 | 2/1995 |
| EP | 0 648 122 | 4/1995 |
| EP | 0 392 640 | 6/1995 |
| EP | 0 441 418 | 7/1995 |
| EP | 0 670 705 | 9/1995 |
| EP | 0 690 736 | 1/1996 |
| EP | 0 724 888 | 8/1996 |
| EP | 0 465 601 | 1/1997 |
| EP | 0 754 064 | 1/1997 |
| EP | 0 762 860 | 3/1997 |
| EP | 0 772 464 | 5/1997 |
| EP | 0 537 559 | 1/1998 |
| EP | 0 620 720 | 3/1998 |
| EP | 0 856 318 | 8/1998 |
| EP | 0 858 810 | 8/1998 |
| EP | 0 651 983 | 9/1998 |
| EP | 0 777 504 | 10/1998 |
| EP | 0 876 165 | 11/1998 |
| EP | 0 888 141 | 1/1999 |
| EP | 0 912 251 | 5/1999 |
| EP | 0 782 421 | 7/1999 |
| EP | 1 068 451 | 10/1999 |
| EP | 1 007 015 | 6/2000 |
| EP | 1 013 290 | 6/2000 |
| EP | 1 021 180 | 7/2000 |
| EP | 1 029 585 | 8/2000 |
| EP | 1 030 657 | 8/2000 |
| EP | 0 688 189 | 9/2000 |
| EP | 1 169 071 | 10/2000 |
| EP | 0 690 706 | 11/2000 |
| EP | 1 085 925 | 3/2001 |
| EP | 1 088 569 | 4/2001 |
| EP | 1 105 110 | 6/2001 |
| EP | 1 105 171 | 6/2001 |
| EP | 1 105 180 | 6/2001 |
| EP | 1 107 813 | 6/2001 |
| EP | 0 865 304 | 7/2001 |
| EP | 1 411 874 | 7/2001 |
| EP | 1 138 336 | 10/2001 |
| EP | 1 156 839 | 11/2001 |
| EP | 1 283 702 | 11/2001 |
| EP | 0 921 775 | 12/2001 |
| EP | 0 564 502 | 1/2002 |
| EP | 1 339 366 | 6/2002 |
| EP | 0 875 222 | 7/2002 |
| EP | 1 218 437 | 7/2002 |
| EP | 1 897 569 | 8/2002 |
| EP | 0 853 950 | 10/2002 |
| EP | 1 306 123 | 2/2003 |
| EP | 1 513 478 | 4/2003 |
| EP | 0 708 620 | 5/2003 |
| EP | 1 088 569 | 8/2003 |
| EP | 0 993 317 | 9/2003 |
| EP | 0 880 953 | 10/2003 |
| EP | 1 565 219 | 12/2003 |
| EP | 1 219 311 | 7/2004 |
| EP | 1 440 667 | 7/2004 |
| EP | 1 440 737 | 7/2004 |
| EP | 1 018 967 | 8/2004 |
| EP | 1 488 816 | 12/2004 |
| EP | 1578477 A2 | 9/2005 |
| EP | 1 440 667 | 3/2006 |
| EP | 1 632 252 | 3/2006 |
| EP | 1 284 777 | 4/2006 |
| EP | 1 263 366 | 7/2006 |
| EP | 0 982 015 | 8/2006 |
| EP | 1 620 720 | 11/2006 |
| EP | 1 448 261 | 2/2007 |
| EP | 1 171 065 | 3/2007 |
| EP | 1 772 160 | 4/2007 |
| EP | 1 476 217 | 3/2008 |
| EP | 1 121 163 | 11/2008 |
| EP | 1 772 160 | 6/2009 |
| EP | 2 111 804 | 10/2009 |
| EP | 1 513 478 | 12/2009 |
| EP | 1 637 088 | 1/2010 |
| EP | 2 172 164 | 4/2010 |
| EP | 2 255 837 | 12/2010 |
| EP | 2 462 908 | 6/2012 |
| FR | 1163907 | 10/1958 |
| GB | 114754 | 4/1918 |
| GB | 236350 | 7/1925 |
| GB | 641061 | 8/1950 |
| GB | 1063066 | 3/1967 |
| GB | 1224009 | 3/1971 |
| GB | 1400124 | 7/1975 |
| GB | 1549756 | 8/1979 |
| GB | 2085305 | 1/1985 |
| GB | 2195255 | 4/1988 |
| GB | 2288734 | 11/1995 |
| GB | 2307180 | 5/1997 |
| GB | 2329127 | 3/1999 |
| GB | 2305610 | 7/1999 |
| GB | 2336546 | 10/1999 |
| GB | 2378392 | 2/2003 |
| GB | 2357286 | 11/2003 |
| GB | 2389794 | 12/2003 |
| GB | 2365350 | 8/2004 |
| GB | 2415908 | 1/2006 |
| GB | 2422545 | 8/2006 |
| GB | 2423019 | 8/2006 |
| GB | 2424581 | 10/2006 |
| GB | 2424582 | 10/2006 |
| GB | 2435419 | 2/2007 |
| JP | 59-502014 | 12/1984 |
| JP | 2001-314479 A | 11/2001 |
| JP | 2003-165843 | 6/2003 |
| JP | 2004-121819 | 4/2004 |
| JP | 2005 261376 | 9/2005 |
| SU | 1251912 A1 | 4/1983 |
| WO | WO 84/01904 | 5/1984 |
| WO | WO 87/00759 | 2/1987 |
| WO | WO 90/11795 | 10/1990 |
| WO | WO 91/00718 | 1/1991 |
| WO | WO 92/09651 | 6/1992 |
| WO | WO 92/13713 | 8/1992 |
| WO | WO 92/19313 | 11/1992 |
| WO | WO 92/20299 | 11/1992 |
| WO | WO 93/00056 | 1/1993 |
| WO | WO 93/06802 | 4/1993 |
| WO | WO 93/09176 | 5/1993 |
| WO | WO 93/09727 | 5/1993 |
| WO | WO 94/20041 | 9/1994 |
| WO | WO 94/20133 | 9/1994 |
| WO | WO 95/03838 | 2/1995 |
| WO | WO 96/00760 | 1/1996 |

(56) References Cited

FOREIGN PATENT DOCUMENTS

| | | |
|---|---|---|
| WO | WO 96/05873 | 2/1996 |
| WO | WO 96/24316 | 8/1996 |
| WO | WO 96/40174 | 12/1996 |
| WO | WO 97/03717 | 2/1997 |
| WO | WO 97/13520 | 4/1997 |
| WO | WO 97/33922 | 9/1997 |
| WO | WO 97/42986 | 11/1997 |
| WO | WO 97/43991 | 11/1997 |
| WO | WO 98/06444 | 2/1998 |
| WO | WO 98/13000 | 4/1998 |
| WO | WO 98/38955 | 9/1998 |
| WO | WO 99/01173 | 1/1999 |
| WO | WO 99/15121 | 4/1999 |
| WO | WO 99/17698 | 4/1999 |
| WO | WO 99/23010 | 5/1999 |
| WO | WO 99/30629 | 6/1999 |
| WO | WO 99/47097 | 9/1999 |
| WO | WO 99/64081 | 12/1999 |
| WO | WO 99/65536 | 12/1999 |
| WO | WO 00/07653 | 2/2000 |
| WO | WO 00/09199 | 2/2000 |
| WO | WO 00/38752 | 7/2000 |
| WO | WO 00/50143 | 8/2000 |
| WO | WO 00/59424 | 10/2000 |
| WO | WO 00/61206 | 10/2000 |
| WO | WO 00/62827 | 10/2000 |
| WO | WO 00/64396 | 11/2000 |
| WO | WO 01/05443 | 1/2001 |
| WO | WO 01/19430 | 3/2001 |
| WO | WO 01/34223 | 5/2001 |
| WO | WO 01/35882 | 5/2001 |
| WO | WO 01/37773 | 5/2001 |
| WO | WO 01/41779 | 6/2001 |
| WO | WO 01/49233 | 7/2001 |
| WO | WO 01/62312 | 8/2001 |
| WO | WO 01/66017 | 9/2001 |
| WO | WO 01/85248 | 11/2001 |
| WO | WO 02/00268 | 1/2002 |
| WO | WO 02/02079 | 1/2002 |
| WO | WO 02/05737 | 1/2002 |
| WO | WO 02/09765 | 2/2002 |
| WO | WO 02/20026 | 3/2002 |
| WO | WO 02/26180 | 4/2002 |
| WO | WO 02/34304 | 5/2002 |
| WO | WO 02/39940 | 5/2002 |
| WO | WO 02/41878 | 5/2002 |
| WO | WO 02/45761 | 6/2002 |
| WO | WO 02/064182 | 8/2002 |
| WO | WO 02/083046 | 10/2002 |
| WO | WO 02/091965 | 11/2002 |
| WO | WO 02/092783 | 11/2002 |
| WO | WO 02/094256 | 11/2002 |
| WO | WO 02/102864 | 12/2002 |
| WO | WO 03/020358 | 3/2003 |
| WO | WO 03/041686 | 5/2003 |
| WO | WO 03/063923 | 8/2003 |
| WO | WO 03/071991 | 9/2003 |
| WO | WO 03/086232 | 10/2003 |
| WO | WO 03/092620 | 11/2003 |
| WO | WO 03/101385 | 11/2003 |
| WO | WO 03/074100 | 12/2003 |
| WO | WO 2004/012678 | 2/2004 |
| WO | WO 2004/018020 | 3/2004 |
| WO | WO 2004/024300 | 3/2004 |
| WO | WO 2004/032977 | 4/2004 |
| WO | WO 2004/037334 | 5/2004 |
| WO | WO 2004/045498 | 6/2004 |
| WO | WO 2004/054632 | 7/2004 |
| WO | WO 2004/091370 | 10/2004 |
| WO | WO 2005/009225 | 2/2005 |
| WO | WO 2005/009488 | 2/2005 |
| WO | WO 2005/017000 | 2/2005 |
| WO | WO 2005/018695 | 3/2005 |
| WO | WO 2005/034875 | 4/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/070480 | 8/2005 |
| WO | WO 2005/082435 | 9/2005 |
| WO | WO 2005/105174 | 11/2005 |
| WO | WO 2005/105175 | 11/2005 |
| WO | WO 2005/105176 | 11/2005 |
| WO | WO 2005/123170 | 12/2005 |
| WO | WO 2006/052839 | 5/2006 |
| WO | WO 2006/130594 | 12/2006 |
| WO | WO 2007/019038 | 2/2007 |
| WO | WO 2007/075379 | 7/2007 |
| WO | WO 2008/010094 | 1/2008 |
| WO | WO 2008/039839 | 4/2008 |
| WO | WO 2008/040681 | 4/2008 |
| WO | WO 2008/064503 | 6/2008 |
| WO | WO 2008/104609 | 9/2008 |
| WO | WO 2009/011856 | 1/2009 |
| WO | WO 2009/021523 | 2/2009 |
| WO | WO 2009/066105 | 5/2009 |
| WO | WO 2009/070905 | 6/2009 |
| WO | WO 2009/124100 | 10/2009 |
| WO | WO 2009/158128 | 12/2009 |
| WO | WO 2010/016791 | 2/2010 |
| WO | WO 2010/033271 | 3/2010 |
| WO | WO 2010/033574 | 3/2010 |
| WO | WO 2010/033613 | 3/2010 |
| WO | WO 2010/051068 | 5/2010 |
| WO | WO 2010/051073 | 5/2010 |
| WO | WO 2010/072309 | 7/2010 |
| WO | WO 2010/142959 | 12/2010 |
| WO | WO 2010/147533 | 12/2010 |
| WO | WO 2012/001371 | 1/2012 |
| WO | WO 2012/069793 | 5/2012 |
| WO | WO 2012/069794 | 5/2012 |

OTHER PUBLICATIONS

U.S. Appl. No. 14/535,736, filed Nov. 7, 2014, Blott et al.
U.S. Appl. No. 14/584,274, filed Dec. 29, 2014, Blott et al.
U.S. Appl. No. 14/585,786, filed Dec. 30, 2014, Blott et al.
"Hydrocolloids," J. of Wound Care, vol. 1, No. 2, (Jul.-Aug. 1992), pp. 27-30.
Achterberg, V., Ph.D., Hydroactive dressings and serum proteins: an in vitro study, Journal of Wound Care, February, vol. 5, No. 2, 1996 (pp. 79-82).
Alper, J.C., et al., *An Effective Dressing for a Large, Draining Abdominal wound*, RN, Dec. 1988, 24-25.
Alper, J.C., et al., *Moist Wound Healing under a Vapor Permeable Membrane, Journ. of Amer. Acad. of Derm.*, Mar. 1983, 8(3),347-353.
Ashrafov, A.A. and K.G. Ibishov, An Experimental and Clinical Validation for the Use of a Collagen Sponge for Treating the Suppurative-Inflammatory Complications of Wound Healing in Emergency Abdominal Surgery, Pub Med, Abs. Downloaded from Internet, Apr. 24, 2006.
Aubrey, D.A., et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Barker et al., "Vacuum Pack Technique of Temporary Abdominal Closure"; J. of Traumatic Injury, Infection, and Critical Care, vol. 48, No. 2 (2000).
Barker, D.E., et al., Vacuum Pack Technique of Temporary Abdominal Closure: A 7-Year Experience with 112 Patients, Journ. of Trauma: Injury and Critical Care, Feb. 2000, 4892), 201-207.
Bevan, Damon, et al.: "Diverse and potent activities of HGF/SF in skin wound repair", Journal of Pathology, J Pathol 2004; 203: 831-838.
Bier, A., Hyperemia as a Therapeutic Agent, *Ed. Dr. Gustavus M. Blech, A. Robertson & Co.*, Chicago 1905, (the entire reference has been submitted, but pp. 74-85 may be the most relevant).

(56) References Cited

OTHER PUBLICATIONS

Bier, A., Hyperemia as a Therapeutic Agent, Ed. Dr. Gustavus M. Blech, A. Robertson & Co., Chicago 1905.
Birdsell, D.C., et al., The Theoretically Ideal Donor Site Dressing; Annals of 2 Plastic Surgery, vol. 2, Jun. 1979; Gadgetry, Div. of Plastic Surgery, Foothills, Hospital, Calgarv, Canada, 535-537.
Brock, W.B., et al.: "Temporary closure of open abdominal wounds: the vacuum pack", Am. Surg. Jan. 1995; 61(1)30-5—abstract.
Chariker, M.E., et al, "Effective Management of Incisional and Cutaneous Fistulae with Closed Suction Wound Drainage," Contemporary Surgery. Jun. 1989, pp. 59-63, vol. 34 USA.
Chintamani, et al., "Half versus full vacuum suction drainage after modified radical mastectomy for breast cancer—a prospective randomized clinical trial", Research Article (Jan. 27, 2005), 1-5.
Columbia Electronic Encyclopedia, The: the effect of body temperature on wound healing, (http://encyclopedia2.thefreedictionary.com/body+temperature) (printed Jan. 16, 2009), 3 pages).
Davydov, Y.A., et al., The Bacteriological & Cytological Assessment of Vacuum Therapy of Purulent Wounds, Vestnik Chirurgia 1988, October Edition 48-52 (in Russian with English translation). 1987.
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.
De Lange, M.Y. , et al., "Vacuum-Assisted Closure: Indications and Clinical Experience", Eur J Plast Surg (2000) 2;178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
Eisenbud, D.E., Modern Wound Management, *Anadem Publishing*, Chap. 16, 109-116, 2000.
Finley, John M.,"Practical Wound Management," pp. 45, 127, 143, 149,207, 1981.
Fleischmann, W., et al. "Vacuum Sealing for Treatment of Soft Tissue Injury in Open Fractures," Emergency Surgery (1993) 96:488-492.
Garner et al., "Vacuum-assisted wound closure provides early fascial reapproximation in trauma patients with open abdomens," Am. J. of Surgery 1282 (2001) 630-638.
Gill, P., What is a Counter-Irritant? Name Three and the Method of Applying them, Brit. Journ. Nurs., Jun. 1934, 142.
Harris, "A new technique of skin grafting using Stei-Greffe and a self-adhering foam pad," Brit. J. of Plastic Surg., vol. 34, No. 2, (Apr. 1981), pp. 181-185.
Hartz, R.S., et al., Healing of the Perineal Wound, Arch. Surg., Apr. 1980, 115, 471-474.
Health Technology, Literature R., "Vacuum Assisted Closure Therapy for Wound Care", Health Technology Literature Review (Dec. 2004), 3-59.
Hugh, T.B., Abdominal Wound Drainage, Med. Journ. of Australia, May 4, 1987, 146, p. 505 (Correspondence).
Izmailov, S.G., et al., Device for Treatment of wounds and Abdominal Cavity, Contents, Surg. No. 8 1997, Downloaded from internet http://www.mediasPhera.ru/surqerY/97/8/e8-97ref.htm.
Jahns et al., Poster "Problemwundversorgung mit einem neuen anschmiegsamen Silikonschaumverband mit Anwendung der Vakuumtechnik," 2nd Congress of German Wound Treatment Society 1998.
Deter, K. "Managing Draining Wounds and Fistulae: New and Established Methods" Chronic Wound Care pp. 240-246, 1990.

KCI Licensing, "V.A.C. Abdominal Dressing System Advanced Management of the Open Abdomen," 2004.
KCI Introduces New Vacuum Assisted Closure Product; VAC. Freedom Device Continues Company's Leadership in Advanced Wound Healing Systems, PR Newswire, Oct. 2002.
Khan, et al., "Influence of Chitosan Molecular Weight on its Physical Properties", EIMJM (2003); 2(1); pp. 1-8.
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kordasiewicz, "Abdominal Wound with a Fistula and Large Amount of Drainage," Journal of Wound, Ostomy and Continence Nursing, May/Jun. 2004, pp. 150-153.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Landis, E.M. and J.H. Gibbon, Jr., The Effects of Alternate Suction and Pressure on Blood Flow to the Lower Extremities, Alternate Suction and Pressure, J Clin. Invest. Sep. 1933, 12(5): 925-961.
Lee, J.H. and H.J. Yang, Application of Medifoam B® & Negative Pressure Therapy for the Auxiliary Treatment of Pressure Sore, *Dept. Plastic and Reconstructive Surg.*, College of Medicine, Eulji Univ., Daejeon, Korea, Abs. Sep. 2004, 1 page.
Luchette, F.A., When Should the General Surgeon Leave the Abdomen Open?, Division of 324 Trauma, Surgical Critical Care and Burns, Loyola University Medical Center, Maywood, Illinois. 37 oaces (2004) (Uploaded in 4 parts).
Mayo, C.W., The One-Stage Combined Abdominoperineal Resection for Carcinoma of the Rectum, RectoSigmoid and Sigmoid, *Surgical Clinics of North America*, Aug. 1939, Mayo Clinic No. 1011-1012.
McGuire, S., Drainage after Abdominal Section, *Br. Journ. of Nurs.*, Dec. 15, 1903, 447-449.
Miles, W.E., A Method of Performing Abdominoperineal Excision for Carcinoma of the 341 Rectum and of the Terminal Portion of the Pelvic Colon, The Lancet, Dec. 19, 1908, 1812-1813.
Mitchell, Richard N., et al.: "Role of Stem Cells in Tissue Homeostasis", Pocket Companion to Robbins and Cotran Pathologic Basis of Diseas, 7th Ed., 2006.
Morykwas, M. J., et al., "Vacuum-Assisted Closure: A New Method for Wound Control and Treatment: Animal Studies and Basic Foundation," *Annals of Plastic Surgery* 38 (1997) 553-562.
Morykwas, M. J., et al.: "Nonsurgical Modalities to Enhance Healing and Care of Soft Tissue Wounds", Journal of the Southern Orthopaedic Association, vol. 6, No. 4 Winter 1997 in 12 pages.
Navsaria, et al.: "Temporary closure of open abdominal wounds by the modified sandwich-vacuum pack technique", British Journal of Surgery 2003; 90: 718-722.
Nicholas, J.M., Options for Management of the Open Abdomen, Presentation from Emory University School of Medicine, 66 pgs. Invited Speaker American College of Surgeons 32nd Annual Spring Meeting, General Session 12—Presentation and Panel Discussion on the Open Abdomen in General Surgery—How Do You Close the Abdomen When You Can't—Boston Marriott Copley Place Hotel, Boston, MA Apr. 26, 2004.
Nursing75, Wound Suction: Better Drainage with Fewer Problems, Nursing, vol. 5, No. 10, Oct. 1975, pp. 52-55.
Orgill, D. P., et al., Microdeformational Wound Therapy—A New Era in Wound Healing, Tissue Engin. and Wound Healing Laboratory, Brigham and Women's Hospital, Business Briefing: Global Surgery—Future Direction 2005, 22.
Orgill, D.P., et al., Guidelines for Treatment of Complex Chest Wounds with Negative Pressure Wound Therapy, *Wounds, A Compendium of Clinical Research and Practice*, Suppl. B, Dec. 2004, 1-23.
Schein et al., "The 'Sandwich Technique' in the Management of the Open Abdomen," British Journal of Surger, 1986, vol. 73, May, pp. 369-370.
Smith, et al.; Vacuum Pack Technique of Temporary Abdominal Closure: A Four-Year Experience; The American Surgeon; Dec. 1997; p. 1102-1108; vol. 63, No. 12.

(56) References Cited

OTHER PUBLICATIONS

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

Solovev, V.A. "Treatment and Prevention of Suture Failures after Gastric Resection" (Dissertation Abstract) (S.M. Kirov Gorky State Medical Institute, Gorky USSR 1988).

Stewart, Joanne, Ph.D., World Wide Wounds—Next generation of products for wound management—2002 (13 pages).

Svedman, P., "Irrigation Treatment in Split-Thickness Skin Grafting of Intractable Leg Ulcers," Scand J. Plast. Reconst. Surg., 19:211-213, 1985.

Svedman, P., "Irrigation Treatment of Leg Ulcers," The Lancet, Sep. 1983, 532-34.

Svedman, P., A Dressing Allowing Continuous Treatment of a Biosurface, IRCS Med. Science: Biomed. Tech.; Clinic. Med.; Surg. and Transplantation, 1979, 7, p. 221.

Svedman, P., et al., "A Dressing System Providing Fluid Supply and Suction Drainage Used for Continuous or Intermittent Irrigation," Annals of Plastic Surgery, vol. 17, No. 2, Aug. 1986, pp. 125-133.

Swift, et al, "Quorum Sensing in *Aeromonas hydrophila* and *Aeromonas salmoncida*: Identification of LuxRI Homologs AhyRI and AsaRI and Their Cognate N-Acylhomoserine Lactone Signal Molecules," J. Bacteriol., 179(17):5271-5281 (1997).

Teder and Svedman et al., "Continuous Wound Irrigation in the Pig," Journal of Investigative Surgery, 1990, vol. 3, pp. 399-407.

Tribble, David E. M.D., An Improved Sump Drain-Irrigation Device of Simple Construction, Archives of Surgery New York, pp. 511-513, 1972 vol. 105.

Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.

Vijanto, J. and J. Raekallio, Local Hyperalimentation of Open Wounds, Br. J. surg., 1976, 63, 427-430.

Webb, New Techniques in Wound Management: Vacuum-Assisted Wound Closure, Journal of the American Academy of Orthopadic Surgeons, v. 10, No. 5, pp. 303-311, Sep. 2002.

Westaby, S., et al., "A Wound Irrigation Device", The Lancet, Sep. 2, 1978, pp. 503-504.

Wooding-Scott, Margaret, et al., "No Wound is Too Big for Resourceful Nurses," RN Dec. 1988, pp. 22-25 USA.

Wound Suction, Nursing, Oct. 1975, USA pp. 52-53.

US 6,216,701, 04/2001, Heaton et al. (withdrawn)

US 6,306,115, 10/2001, Kelly et al. (withdrawn)

\* cited by examiner

Section Through X-X

Section Through X -X

Section Through X -X

Section Through X -X

Section Through X-X

Section View on X-X

APPARATUS FOR ASPIRATING, IRRIGATING AND CLEANSING WOUNDS

CROSS-REFERENCE TO RELATED APPLICATIONS

This application is a continuation of U.S. application Ser. No. 13/363,320, filed Jan. 31, 2012, which is a divisional of U.S. application Ser. No. 12/416,829, filed Apr. 1, 2009 and issued as U.S. Pat. No. 8,398,614, which is a continuation of U.S. application Ser. No. 10/533,275, filed Nov. 9, 2005 and issued as U.S. Pat. No. 7,524,315, which is the national stage application of PCT/GB03/004647, filed Oct. 28, 2003, which claims priority to GB 0224986.0, filed Oct. 28, 2002. The disclosure of each of these prior applications is incorporated by reference in its entirety and should be considered a part of this specification.

BACKGROUND OF THE INVENTION

1. Field of the Invention

The present invention relates to apparatus and a medical wound dressing for aspirating, irrigating and/or cleansing wounds, and a method of treating wounds using such apparatus for aspirating, irrigating and/or cleansing wounds. It relates in particular to such an apparatus, wound dressing and method that can be easily applied to a wide variety of, but in particular chronic, wounds, to cleanse them of materials that are deleterious to wound healing, whilst retaining materials that are beneficial in some therapeutic aspect, in particular to wound healing.

2. Description of the Related Art

Before the present invention, aspirating and/or irrigating apparatus therefor were known, and tended to be used to remove wound exudate during wound therapy. In known forms of such wound therapy, the offtake from the wound, especially when in a highly exuding state, is voided to waste, e.g. to a collection bag, as illustrated in DE-A-4 012 232.

Materials deleterious to wound healing are removed in this way.

However, materials that are beneficial in promoting wound healing, such as growth factors, cell matrix components, and other physiologically active components of the exudate from a wound are lost to the site where they can be potentially of most benefit, i.e. the wound bed, when such therapy is applied.

Such known forms of wound dressing and aspiration and/or irrigation therapy systems often create a wound environment under the dressing that thus may result in the loss of optimum performance of the body's own tissue healing processes, and slow healing and/or in weak new tissue growth that does not have a strong three-dimensional structure adhering well to and growing from the wound bed. This is a significant disadvantage, in particular in chronic wounds.

It thus would be desirable to provide a system of therapy which can remove materials deleterious to wound healing from wound exudate, whilst retaining materials that are beneficial in promoting wound healing in contact with the wound bed.

Dialysis is a known method of treating bodily fluids such as blood ex vivo, to cleanse them of materials that are deleterious to the body systemically. Removal of such materials by contact with the dialysate is the prime purpose of dialysis, whilst also retaining materials such as blood, cells and proteins. Other materials that may have an additional positive therapeutic action are potentially lost to the system through the dialysis membrane, which is also permeable to them. The balance of such materials in the bodily fluid in recirculation may thus be further depleted.

It would be desirable to provide a system of therapy which can remove materials deleterious to wound healing from wound exudate, without substantially diluting materials that are beneficial in promoting wound healing in contact with the wound bed, and which can continuously supply and recirculate such materials to the wound simultaneously.

Dialysis for treating bodily fluids is also a systemic therapy, since the treated fluid is returned to within the body. This is in contrast to a topical therapy in which the treated fluid is recycled outside the body, e.g. to a wound. Most dialysis also requires large amounts of bodily fluids such as blood, and consequently the relevant devices tend not to be portable. Even when in a highly exuding state, chronic wounds produce relatively little fluid to be treated compared with internal bodily systems and relatively little materials that are beneficial in some therapeutic aspect to be retained in the wound and/or its environment.

SUMMARY OF THE INVENTION

It is therefore desirable
a) to obviate at least some of the abovementioned disadvantages of known aspiration and/or irrigation therapy systems, and
b) to provide a system of therapy which can remove materials deleterious to wound healing from wound exudate, whilst retaining materials that are beneficial in promoting wound healing in contact with the wound bed.

It is also desirable
a) to obviate at least some of the abovementioned disadvantages of known dialysis systems, and
b) to provide a system of therapy which can remove materials deleterious to wound healing from wound exudate, whilst retaining materials that are beneficial in promoting wound healing in contact with the wound bed,
c) without affecting the body systemically.

It is also desirable
a) to obviate at least some of the abovementioned disadvantages of known dialysis systems, and
b) to provide a system of therapy which can remove materials deleterious to wound healing from wound exudate, whilst retaining materials that are beneficial in promoting wound healing in contact with the wound bed, and
c) is portable.

Vascular supply to, and circulation in, tissue underlying and surrounding the wound is often compromised. It is therefore desirable to provide a system of therapy that retains and supplies therapeutically active amounts of materials that are beneficial in reversing this effect whilst removing deleterious materials, thereby promoting wound healing.

Thus, according to a first aspect of the present invention there is provided an apparatus for aspirating, irrigating and/or cleansing wounds, characterized in that it comprises
 a) a fluid flow path, comprising
  i) a conformable wound dressing, having
   a backing layer which is capable of forming a relatively fluid-tight seal or closure over a wound and
   at least one inlet pipe for-connection to a fluid supply tube, which passes through and/or under the wound-facing face, and
   and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure over the wound,
  at least one inlet pipe being connected to a fluid recirculation tube, and at least one outlet pipe being connected to a fluid offtake tube: and
ii) a means for fluid cleansing having at least one inlet port connected to a fluid offtake tube and at least one outlet port connected to a fluid recirculation tube;
b) a fluid reservoir connected by a second fluid supply tube to an integer of the flow path (optionally or as necessary via means for flow switching between supply and recirculation);
c) a device for moving fluid through the wound dressing and means for fluid cleansing, and optionally or as necessary the fluid supply tube; and
d) optionally means for bleeding the flowpath, such that fluid may be supplied to fill the flowpath from the fluid reservoir via the fluid supply tube (optionally or as necessary via the means for flow switching) and recirculated by the device through the flow path.

The means for flow switching between supply and recirculation may take any form that enables the wound simultaneously to be
  a) put into communication with the fluid reservoir but
  b) closed to the fluid recirculation tube, and
  c) vice versa.

Thus, if there is only one inlet pipe that passes through and/or under the wound-facing face of the wound dressing, the fluid reservoir is connected by the fluid supply tube to the flow path via means for flow switching as desired the into a fluid recirculation tube or a fluid offtake tube.

In this case, the means for flow switching between supply and recirculation may be a regulator, such as a T-valve. This is connected in turn to two parts of a fluid recirculation tube or a fluid offtake tube and the fluid supply tube, such that the desired flow switching between supply and recirculation is achieved.

If there are two or more inlet pipes, these may be connected respectively to a fluid supply tube or fluid recirculation tube, respectively having a first regulator and a second regulator, such as a valve or other control device for admitting fluids into the wound.

The desired flow switching between supply and recirculation is achieved by respectively having the first regulator open when the second regulator is shut, and vice versa.

The means for bleeding the flowpath may be situated in any appropriate part of the apparatus that is in contact with the irrigant and/or wound exudate, but is usually within the offtake and/or recirculation tubes. However, it is often as far downstream of and away from the reservoir and the fluid supply tube as possible, so that it may be used to prime the whole of the flowpath from the fluid reservoir via the fluid supply tube.

It may be a regulator, such as a valve or other control device, e.g. a T-valve that is turned to switch between bleed and recirculation, for bleeding fluids from the apparatus, e.g. to a waste reservoir, such as a collection bag.

Alternatively, flow switching between supply and recirculation may not be desired, but rather concomitant bleeding and/or recirculation is desired. The latter may occur when the volume of irrigant and/or wound exudate in recirculation is increased by continuing addition to it of a) wound exudate, and/or
b) fluid passing from a cleansing fluid through a selectively permeable integer, for example in a system such as a dialysis unit.

The means for bleeding the offtake and/or recirculation tubes may then be provided in the form of a regulator, such as a simple valve or other control device for admitting or blocking the passage of irrigant and/or exudate through a bleed line branching from the recirculation path.

The means for fluid cleansing may as desired be a 'single-phase system.'

In this, the circulating fluid from the wound and the fluid reservoir passes through a self-contained system in which materials deleterious to wound healing are removed and the cleansed fluid, still containing materials that are beneficial in promoting wound healing, is returned via the recirculation tube to the Wound bed. Such systems are described in further detail hereinafter in connection with the means for fluid cleansing.

Alternatively, where appropriate it may be provided in the form of a two-phase system, such as a dialysis unit, or a biphasic liquid extraction unit.

In this, the circulating fluid from the wound and the fluid reservoir passes through a system in which the fluid recirculates in indirect or (less usually, direct) contact with a second fluid (dialysate) phase, more usually a liquid, in which materials deleterious to wound healing are removed and the cleansed fluid, still containing materials that are beneficial in promoting wound healing, is returned via the recirculation tube to the wound bed. Such systems are described in further detail hereinafter in connection with the means for fluid cleansing.

In use, typically, the means for flow switching between supply and recirculation tubes is set to admit fluid into the wound from the fluid reservoir but to close the wound to the fluid recirculation tube.

Then, any means for bleeding the offtake and/or recirculation tubes are is opened and the device for moving fluid through the wound and means for fluid cleansing is started.

The capacity of the apparatus flow path and the flow rate of irrigant and/or wound exudate from the wound will largely determine whether it is appropriate to run the device to prime the apparatus throughout the whole length of the apparatus flow path, i.e. to displace any existing fluid reservoir (often air) from the fluid recirculation path, and for how long it should be run. Typically, there is a preponderance of irrigant from the fluid reservoir over wound exudate in recirculation, so that use of the device for moving fluid through the wound is appropriate for this purpose.

It is allowed to run until the apparatus is primed throughout the whole length of the apparatus flow path.

Then, typically the means for bleeding the offtake and/or recirculation tubes is closed, and the means for flow switching between supply and recirculation tubes is set to close the wound to the fluid reservoir but to admit fluid into the wound from the fluid recirculation tube.

If the means for fluid cleansing is a two-phase system, such as a dialysis unit, or a biphasic extraction unit, the cleansing fluid is typically set in motion in contact with the surface of the selectively permeable integer, for example the polymer film, sheet or membrane. Of course, the cleansing fluid may less usually be static, and then this step is omitted.

As noted below in more detail, the volume of irrigant and/or wound exudate from the wound in recirculation may be increased by continuing addition to it of a) wound exudate, and/or b) fluid passing from a cleansing fluid through a selectively permeable integer, for example the polymer film, sheet or membrane of a two-phase system, such as an dialysis unit.

Additionally or alternatively, it may be desired to apply a negative pressure to the wound by means of a device for moving fluid through the wound and means for fluid cleansing applied to the fluid in recirculation in the fluid recirculation tube downstream of and away from the wound dressing.

In such case, it may be desirable to provide a system in which concomitant bleeding and/or recirculation is possible, and to make the necessary adjustments to maintain the desired balance of fluid in recirculation by means of the means for bleeding the offtake and/or recirculation tubes.

The volume of irrigant and/or wound exudate from the wound in recirculation may be decreased by continuing loss from it of fluid passing from a cleansing fluid through a selectively permeable integer, for example in a system such as a dialysis unit.

Additionally or alternatively, it may be desired to apply a positive pressure to the wound by means of a device for moving fluid through the wound and means for fluid cleansing applied to the fluid in recirculation in the fluid recirculation tube upstream of and towards the wound dressing.

The means for flow switching between supply and recirculation may be similarly provided in a form in which concomitant supply and/or recirculation is possible, and to make the necessary adjustments to maintain the desired balance of fluid in recirculation by means of the means for flow switching.

It will be appreciated that where a positive or negative pressure is to be applied to the wound, at least one hollow body in the recirculation flow path to and from the wound bed should have sufficient resilience against the pressure to allow any significant compression or decompression of the irrigant fluid to occur.

In all embodiments of the apparatus, the type and material of such bodies (which are defined by a film, sheet or membrane) that are described by way of example herein to be suitable for use in the present invention will be largely capable of this function.

Thus, examples of suitable materials for bodies defined by a film, sheet or membrane, such as inlet or offtake and/or recirculation tubes and structures such as bags, chambers and pouches, filled with irrigant fluid, e.g. the backing layer of the wound dressing are suitably elastically resilient thermoplastic materials that are potentially capable of this function when pressure is applied in this way.

The present invention in this aspect provides several advantages.

One is that application of a positive pressure to the wound under the backing layer may make it possible to flood the tissue underlying the wound with one or more physiologically active components.

This may be effected in therapeutically active amounts, to promote greater wound healing than by treatment with the fluid physiologically active component(s) alone.

Such physiologically active components of the exudate that are beneficial to wound healing may be e.g. be enzymes or other species and may be supplied from the dialysate of a dialytic means for fluid cleansing.

It is believed that using the apparatus for aspirating, irrigating and/or cleansing wounds of the present invention cyclically the effects may be further enhanced.

Circulating wound fluid aids in movement of biological signalling molecules involved in wound healing to locations in the wound bed that are favourable to the wound healing process and/or to cells that would otherwise not be exposed to them, e.g. in a highly exuding wound.

This is especially the case in those embodiments of the apparatus of this first aspect of the present invention for aspirating, irrigating and/or cleansing wounds where there is an inlet or outlet manifold from which tubules radiate and run to the wound bed to end in openings that deliver and collect the fluid directly from the wound bed over an extended area.

Such materials include cytokines, enzymes, nutrients for wound cells to aid proliferation, oxygen, and other molecules that are beneficially involved in wound healing, such as growth factors, and others having beneficial effects (which may be further enhanced) in causing chemotaxis.

In all embodiments of the apparatus of this first aspect of the present invention for aspirating, irrigating and/or cleansing wounds, a particular advantage is the tendency of the wound dressing to conform to the shape of the bodily part to which it is applied.

The wound dressing comprises a backing layer with a wound-facing face which is capable of forming a relatively fluid-tight seal or closure over a wound and at least one inlet pipe for connection to a fluid supply tube or recirculation tube, which passes through and/or under the wound-facing face, and and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure.

The term 'relatively fluid-tight seal or closure' is used herein to indicate one which is fluid- and microbe-impermeable and permits a positive or negative pressure of up to 50% atm., more usually up to 15% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating and/or cleansing the wound across the area of the wound.

Examples of such include a substantially flat film, sheet or membrane, or a bag, chamber, pouch or other structure of the backing layer, e.g. of polymer film, which can contain the fluid.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound.

Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof; polysiloxanes; polyesters, such as polycarbonates; polyamides, e.g. 6-6 and 6-10, and hydrophobic polyurethanes.

They may be hydrophilic, and thus also include hydrophilic polyurethanes.

They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Preferred materials for the present wound dressing include thermoplastic elastomers and curable systems.

The backing layer is capable of forming a relatively fluid-tight seal or closure over the wound and/or around the inlet and outlet pipe(s).

However, in particular around the periphery of the wound dressing, outside the relatively fluid-tight seal, it is preferably of a material that has a high moisture vapour permeability, to prevent maceration of the skin around the wound. It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound.

This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage. (A light switchable adhesive is one the adhesion of which is reduced by photocuring. Its use can be beneficial in reducing the trauma of removal of the dressing.)

Thus, the backing layer may have a flange or lip extending around the proximal face of the backing layer, of a transparent or translucent material (for which it will be understood that materials that are listed above are amongst those that are suitable).

This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the proximal wound is removed prior to application of radiation of an appropriate wavelength to the flange or lip.

If the periphery of the wound dressing, outside the relatively fluid-tight seal, that bears an adhesive film to attach it to the skin around the wound, is of a material that has a high moisture vapour permeability or is a switchable material, then the adhesive film, if continuous, should also have a high or switchable moisture vapour permeability, e.g. be an adhesive such as used in Smith & Nephew's Allevyn™, IV3000™ and OpSite™ dressings.

Where a vacuum, is applied to hold the wound dressing in place in a fluid-tight seal around the periphery of the wound-facing face of the wound dressing, the wound dressing may be provided with a silicone flange or lip to seal the dressing around the wound; This removes the need for adhesives and associated trauma to the patient's skin.

Where the interior of, and the flow of irrigant and/or wound exudate to and through, the dressing is under any significant positive pressure, which will tend to act at peripheral points to lift and remove the dressing off the skin around the wound.

In such use of the apparatus, it may thus be necessary to provide means for forming and maintaining such a seal or closure over the wound against such positive pressure on the wound, to act at peripheral points for this purpose.

Examples of such means include light switchable adhesives, as above, to secure the dressing in place to prevent leakage.

Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheaths, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheaths, wraps, stockings and hose that are a compressive fit over a limb wound to apply suitable pressure to it when the therapy is applied in this way.

Such means may each be laid out over the wound dressing to extend beyond the periphery of the backing layer of the wound dressing, and as appropriate will be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound, Such means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The means and the dressing may be separate structures, permanently unattached to each other.

In a more suitable layout for higher positive pressures on the wound, a stiff flange or lip extends around the periphery of the proximal face of the backing layer of the wound dressing as hereinbefore defined.

The flange or lip is concave on its proximal face to define a peripheral channel or conduit.

It has a suction outlet that passes through the flange or lip to communicate with the channel or conduit and may be connected to a device for applying a vacuum, such as a pump or a piped supply of vacuum.

The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound.

The device then applies a vacuum to the interior of the flange or lip, thus forming and maintaining a seal or closure acting at peripheral points around the wound against the positive pressure on the wound.

With all the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

To form the relatively fluid-tight seal or closure over a wound and around the inlet pipe(s) and outlet pipe(s) at the point at which they pass through and/or under the wound-facing face, the backing layer may be integral with these other components.

The components may alternatively just be a push, snap or twist-lock fit with each other, or adhered or heat-sealed together.

The or each inlet pipe or outlet pipe may be in the form of an aperture, such as a funnel, hole, opening, orifice, luer, slot or port for connection as a female member respectively to a mating end of
- a fluid recirculation tube and/or fluid supply tube (optionally or as necessary via means for forming a tube, pipe or hose, or nozzle, hole, opening, orifice, luer, slot or port for connection as a male member respectively to a mating end of
- a fluid recirculation tube and/or fluid supply tube (optionally or as necessary via means for flow switching between supply and recirculation) or a fluid offtake tube.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components.

The or each pipe will generally pass through, rather than under the backing layer. In such case, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of a fluid recirculation tube and/or fluid supply tube or fluid offtake tube.

Alternatively or additionally, where appropriate the backing layer may have a stiff flange or lip extending around the proximal face of the backing layer to stiffen, reinforce or otherwise strengthen the backing layer.

The wound dressing may not comprise any integer under the backing layer in the wound in use.

However, this may not provide a system to distribute irrigant over a sufficient functional surface area to irrigate the wound at a practical rate. To be suitable for use, in particular in chronic wound dialysis, with relatively high concentrations of materials that are deleterious to wound healing, it may be advantageous to provide a system where wound irrigant and/or wound exudate may be distributed more evenly, or pass in a more convoluted path under the dressing over the wound bed.

Accordingly, one form of the dressing is provided with a 'tree' form of pipes, tubes or tubules that radiate from an inlet manifold to the wound bed to end in apertures and deliver the circulating fluid directly to the wound bed via the apertures. Similarly, there is an outlet manifold from which tubules radiate and run to the wound bed to end in openings and collect the fluid directly from the wound bed.

The pipes, etc. may radiate regularly or irregularly through the wound in use, respectively from the inlet or outlet manifold, although regularly may be preferred. A more suitable layout for deeper wounds is one in which the pipes, etc. radiate hemispherically and concentrically, to the wound bed.

For shallower wounds, examples of suitable forms of such layout of the pipes, etc. include ones in which the pipes, etc. radiate in a flattened hemiellipsoid and concentrically, to the wound bed.

Other suitable forms of layout of the pipes, etc. include one which have pipes, tubes or tubules extending from the inlet pipe(s) and/or outlet pipe(s) at the point at which they pass through and/or under the wound-facing face of the backing layer to run over the wound bed. These may have a blind bore with perforations, apertures, holes, openings, orifices, slits or slots along the pipes, etc.

These pipes, etc. then effectively form an inlet pipe manifold that delivers the circulating fluid directly to the wound bed or outlet pipe or collects the fluid directly from the wound respectively.

It does so via the holes, openings, orifices, slits or slots in the tubes, pipes, tubules, etc. over most of the wound bed under the backing layer.

It may be desirable that the tubes, pipes or tubules are resiliently flexible, e.g. elastomeric, and preferably soft, structures with good conformability in the wound and the interior of the wound dressing.

When the therapy is applied in this way, the layout of the tubes, pipes, tubules, etc. may depend on the depth and/or capacity of the wound.

Thus, for shallower wounds, examples of suitable forms of such layout of the tubes, pipes, tubules, etc. include ones that consist essentially of one or more of the tubes, etc in a spiral.

A more suitable layout for deeper wounds when the therapy is applied in this way may be one which comprises one or more of the tubes, etc in a helix or spiral helix.

Other suitable layouts for shallower wounds include one which have blind-bore, perforated inlet pipe or outlet pipe manifolds that circulate fluid in the wound when the dressing is in use.

One or both of these may be such a form, the other may be, e.g. one or more straight blind-bore, perforated radial tubes, pipes or nozzles.

Another suitable layout is one in which
- an inlet pipe and/or outlet pipe manifold that delivers the circulating fluid directly to the wound bed or collects the fluid directly from the wound respectively
- via inlet and/or outlet tubes, pipes or tubules,
- and the inlet manifold and/or outlet manifold is formed by slots in layers permanently attached to each other in a stack, and
- the inlet and/or outlet tubes, pipes or tubules are formed by apertures through layers permanently attached to each other in a stack. (In FIG. 10a there is shown an exploded isometric view of such a stack, which is non-limiting.)

As also mentioned herein, the backing layer that is applied may be any that is appropriate to the present system of therapy and permits a positive or negative pressure of up to 50% atm., more usually up to 25% atm. to be applied to the wound.

It is thus often a microbe-impermeable film, sheet or membrane, which is substantially flat, depending on any pressure differential on it, and often with a (generally uniform) thickness similar to such films or sheets used in conventional wound dressings, i.e. up to 100 micron, preferably up to 50 micron, more preferably up to 25 micron, and of 10 micron minimum thickness.

The backing layer may often have a rigid and/or resiliently inflexible or stiff area to resist any substantial play between other components that are not mutually integral, and may be stiffened, reinforced or otherwise strengthened, e.g. by a projecting boss.

Such a form of dressing would not be very conformable to the wound bed, and may effectively form a chamber, hollow or cavity defined by a backing layer and the wound bed under the backing layer.

It may be desirable that the interior of the wound dressing conform to the wound bed, even for a wound in a highly exuding state. Accordingly, one form of the dressing is provided with a wound filler under the backing layer.

This is favourably a resiliently flexible, e.g. elastomeric, and preferably soft, structure with good conformability to wound shape.

It is urged by its own resilience against the backing layer to apply gentle pressure on the wound bed.

The wound filler may be integral with the other components of the dressing, in particular the backing layer.

Alternatively, it may be permanently attached to them/it, with an adhesive film, for example, or by heat-sealing, e.g. to a flange or lip extending from the proximal face, so a not to disrupt the relatively fluid-tight seal or closure over the wound that is needed.

Less usually, the wound filler is releasably attached to the backing layer, with an adhesive film, for example, or these components may be a push, snap or twist-lock fit with each other.

The wound filler and the backing layer may be separate structures, permanently unattached to each other.

The wound filler may be or comprise a solid integer, favourably a resiliently flexible, e.g. elastomeric, and preferably soft, structure with good conformability to wound shape.

Examples of suitable forms of such wound fillers are foams formed of a suitable material, e.g. a resilient thermoplastic. Preferred materials for the present wound dressing include reticulated filtration polyurethane foams with small apertures or pores.

Alternatively or additionally, it may be in the form of, or comprise one or more conformable hollow bodies defined by a film, sheet or membrane, such as a bag, chamber, pouch or other structure, filled with a fluid or solid that urges it to the wound shape.

The film, sheet or membrane, often has a (generally uniform) thickness similar to that of films or sheets used in conventional wound dressing backing layers.

That is, up to 100 micron, preferably up-to 50 micron, more preferably up to 25 micron, and of 10 micron minimum thickness, and is often resiliently flexible, e.g. elastomeric, and preferably soft.

Such a filler is often integral with the other components of the dressing, in particular the backing layer, or permanently attached to them/it, with an adhesive film, for example, or by heat-sealing, e.g. to a flange Examples of suitable fluids contained in the hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials. Examples also include aerosol foams, where the gaseous phase of the aerosol system is air or an inert gas, such as nitrogen or argon, more usually air, at a small positive pressure above atmospheric; and solid particulates, such as plastics crumbs.

Of course, if the backing layer is a sufficiently conformable and/or e.g. an upwardly dished sheet, the backing layer may lie under the wound filler, rather than vice versa.

In this type of layout, in order for the wound filler to urge the wound dressing towards the wound bed, it will usually have to be firmly adhered or otherwise releasably attached to the skin around the wound. This is especially the case in those embodiments where the wound filler and the backing layer are separate structures, permanently unattached to each other.

In such a layout for deeper wounds when the therapy is applied in this way, the means for such attachment may also form and maintain a seal or closure over the wound.

Where the filler is over the backing layer, and the fluid inlet pipe(s) and outlet pipe(s) pass through the wound-facing face of the backing layer, they may run through or around the wound filler over the backing layer.

One form of the dressing is provided with a wound filler under the backing layer that is or comprises a resiliently flexible, e.g. elastomeric, and preferably soft, hollow body defined by a film, sheet or membrane, such as a bag, chamber, pouch or other structure, with apertures, holes, openings, orifices, slits or slots, or tubes, pipes, tubules or nozzles. It communicates with at least one inlet or outlet pipe through at least one aperture, hole, opening, orifice, slit or slot.

The fluid contained in the hollow body may then be the circulating fluid in the apparatus.

The hollow body or each of the hollow bodies then effectively forms an inlet pipe or outlet pipe manifold that delivers the circulating fluid directly to the wound bed or collects the fluid directly from the wound respectively via the holes, openings, orifices, slits or slots, or the tubes, pipes or hoses, etc. in the film, sheet or membrane.

When the therapy is applied in this way, the type of the filler may also be largely determined by the depth and/or capacity of the wound.

Thus, for shallower wounds, examples of suitable wound fillers as a component of a wound dressing include ones that consist essentially of one or more conformable hollow bodies defining an inlet pipe and/or outlet pipe manifold that delivers the circulating fluid directly to the wound bed or collects the fluid directly from the wound.

A more suitable wound filler for deeper wounds when the therapy is applied in this way may be one which comprises one or more conformable hollow bodies defined by, for example a polymer film, sheet or membrane, that at least partly surround(s) a solid integer. This may provide a system with better rigidity for convenient handling.

Unless the wound filler under the backing layer effectively forms an inlet pipe or outlet pipe manifold with a direct connection between the inlet pipe(s) and outlet pipe(s) at the point at which they pass through and/or under the wound-facing face and the wound bed is present, in order for aspiration and/or irrigation of the wound bed to occur, it is appropriate for one or more bores, channels, conduits, passages, pipes, tubes, tubules and/or spaces, etc. to run from the point at which the fluid inlet pipe(s) and outlet pipe(s) pass through and/or under the wound-facing face of the backing layer through or around the wound filter filler under the backing layer.

Less usually, the wound filler is an open-cell foam with pores that may form such bores, channels, conduits, passages and/or spaces through the wound filler under the backing layer.

Where the filler is or comprises one or more conformable hollow bodies defined by, for example a polymer film, sheet or membrane, it may be provided with means for admitting fluids to the wound bed under the wound dressing.

These may be in the form of pipes, tubes, tubules or nozzles running from the point at which the fluid inlet pipe(s) and outlet pipe(s) pass through and/or under the wound-facing face of the backing layer through or around the wound filler under the backing layer.

All of the suitable layouts for shallower wounds that comprise blind-bore, perforated inlet pipe or outlet pipe manifolds that circulate fluid in the wound when the dressing is in use, that are described hereinbefore, may be used under a wound filler under the backing layer.

In brief, suitable layouts include ones where one or both manifolds are annular or toroidal (regular, e.g. elliptical or circular, or irregular), optionally with blind-bore, perforated radial tubes, pipes or nozzles, branching from the annulus or torus; and/or in a meandering, tortuous, winding, zigzag, serpentine or boustrophedic (i.e. in the manner of a ploughed furrow) pattern, or defined by slots in and apertures through layers attached to each other in a stack.

The inlet and/or outlet tubes, the fluid recirculation tube and the fluid supply tube, etc. may be of conventional type, e.g. of elliptical or circular cross-section, and may suitably have a uniform cylindrical bore, channel, conduit or passage throughout their length.

Depending on the desired fluid volume flow rate of irrigant and/or wound exudate from the wound, and the desired amount in recirculation, suitably the largest cross-dimension of the bore may be up to 10 mm for large torso wounds, and up to 2 mm for limb wounds.

The tube walls should suitably thick enough to withstand any positive or negative pressure on them, in particular if the volume of irrigant and/or wound exudate from the wound in recirculation is increased by continuing addition to it of wound exudate, and/or fluid passing from a cleansing fluid through a selectively permeable integer, for example the polymer film, sheet or membrane of a two-phase system, such as an dialysis unit. However, as noted below with regard to pumps, the prime purpose of such tubes is to convey fluid irrigant and exudate through the length of the apparatus flow path, rather than to act as pressure vessels. The tube walls may suitably be at least 25 micron thick.

The bore or any perforations, apertures, holes, openings, orifices, slits or slots along the pipes, etc. or in the hollow body or each of the hollow bodies may be of small cross-dimension.

They may then effectively form a macroscopic and/or microscopic filter for particulates including cell debris and micro-organisms, whilst allowing proteins and nutrients to pass through.

Such tubes, pipes or hoses, etc. through and/or around the filler, whether the latter is a solid integer and/or one or more resiliently flexible or conformable hollow bodies, are described in further detail hereinbefore in connection with the inlet pipe(s) and outlet pipe(s).

The whole length of the apparatus for aspirating, irrigating and/or cleansing wounds should be microbe-impermeable once the wound dressing is over the wound in use.

It is desirable that the wound dressing and the interior of the apparatus for aspirating, irrigating and/or cleansing wounds of the present invention is sterile.

The fluid may be sterilised in the fluid reservoir and/or the rest of the system in which the fluid recirculates, including the means for fluid cleansing, by ultraviolet, gamma or electron beam irradiation. This way, in particular reduces or eliminates contact of internal surfaces and the fluid with any sterilising agent.

Examples of other methods of sterilisation of the fluid also include e.g. the use of ultrafiltration through microapertures or micropores, e.g. of 0.22 to 0.45 micron maximum cross-dimension, to be selectively impermeable to microbes; and fluid antiseptics, such as solutions of chemicals, such as chlorhexidine and povidone iodine; metal ion sources, such as silver salts, e.g. silver nitrate; and hydrogen peroxide;

although the latter involve contact of internal surfaces and the fluid with the sterilising agent.

It may be desirable that the interior of the wound dressing, the rest of the system in which the fluid recirculates, and/or the wound bed, even for a wound in a highly exuding state, are kept sterile after the fluid is sterilised in the fluid reservoir, or that at least naturally occurring microbial growth is inhibited.

Thus, materials that are potentially or actually beneficial in this respect may be added to the irrigant initially, and as desired the amount in recirculation increased by continuing addition.

Examples of such materials include antibacterial agents (some of which are listed above), and antifungal agents.

Amongst those that are suitable are, for example triclosan, iodine, metronidazole, cetrimide, chlorhexidine acetate, sodium undecylenate, chlorhexidine and iodine.

Buffering agents, such as potassium dihydrogen phosphate/disodium hydrogen phosphate may be added to adjust the pH, as may local analgesics/anaesthetics, such as lidocaine/lignocaine hydrochloride, xylocaine (adrenaline, lidocaine) and/or anti-inflammatories, to reduce wound pain or inflammation or pain associated with the dressing.

It is also desirable to provide a system in which physiologically active components of the exudate that are beneficial to wound healing are not removed before or after the application of fluid cleansing.

This may occur, e.g. by the passive deposition of materials that are beneficial in promoting wound healing, such as proteins, e.g. growth factors.

This may occur at any point in the flow path, e.g. in at least one inlet or outlet pipe.

The deposition of materials that are beneficial in promoting wound healing may be combated as follows:

a) extra materials may be added to the irrigant initially, and as desired the amount in recirculation increased by continuing addition, or b) a repellent coating may be used at any point or on any integer in the recirculation path in direct contact with the fluid, e.g. on the means for fluid cleansing or any desired tube or pipe.

Examples of coating materials for surfaces over which the circulating fluid passes include anticoagulants, such as heparin, and high surface tension materials, such as PTFE, and polyamides, which are useful for growth factors, enzymes and other proteins and derivatives.

The apparatus of the invention for aspirating, irrigating and/or cleansing wounds is provided with means for admitting fluids directly or indirectly to the wound under the wound dressing in the form of a fluid supply tube to a fluid reservoir.

The fluid reservoir may be of any conventional type, e.g. a tube, bag (such as a bag typically used for blood or blood products, e.g. plasma, or for infusion feeds, e.g. of nutrients), chamber, pouch or other structure, e.g. of polymer film, which can contain the irrigant fluid.

The reservoir may be made of a film, sheet or membrane, often with a (generally uniform) thickness similar to that of films or sheets used in conventional wound dressing backing layers, i.e. up to 100 micron, preferably up to 50 micron, more preferably up to 25 micron, and of 10 micron minimum thickness, and is often a resiliently flexible, e.g. elastomeric, and preferably soft, hollow body.

In all embodiments of the apparatus the type and material of the tubes throughout the apparatus of the invention for aspirating, irrigating and/or cleansing wounds and the fluid reservoir will be largely determined by their function.

To be suitable for use, in particular on chronic timescales, the material should be non-toxic and biocompatible, inert to any active components, as appropriate of the irrigant from the fluid reservoir and/or wound exudate in the apparatus flow path, and, in any use of a two-phase system dialysis unit, of the dialysate that moves into the circulating fluid in the apparatus.

When in contact with irrigant fluid, it should not allow any significant amounts of extractables to diffuse freely out of it in use of the apparatus.

It should be sterilisable by ultraviolet, gamma or electron beam irradiation and/or with fluid antiseptics, such as solutions of chemicals, fluid- and microbe-impermeable once in use, and flexible.

Examples of suitable materials for the fluid reservoir include synthetic polymeric materials, such as polyolefins, such as polyethylene, e.g. high-density polyethylene and polypropylene.

Suitable materials for the present purpose also include copolymers thereof, for example with vinyl acetate and mixtures thereof. Suitable materials for the present purpose further include medical grade poly(vinyl chloride).

Notwithstanding such polymeric materials, the fluid reservoir will often have a stiff area to resist any substantial play between it and components that are not mutually integral, such as the fluid supply tube towards the wound dressing, and may be stiffened, reinforced or otherwise strengthened, e.g. by a projecting boss.

The device for moving fluid through the wound and means for fluid cleansing may be any appropriate for this purpose, and may act at any appropriate point for this purpose.

It may apply a positive or negative pressure to the wound, although its prime purpose is to move fluid (irrigant from the fluid reservoir and/or wound exudate through the length of the apparatus flow path, rather than to apply a positive or negative pressure to the wound.

If applied to the fluid in recirculation in the fluid recirculation tube upstream of and towards the wound dressing and/or the fluid in the fluid supply tube towards the wound dressing (optionally or as necessary via means for flow switching between supply and recirculation), it will usually apply positive pressure (i.e. above-atmospheric pressure) to the wound bed.

Often the means for fluid cleansing is (most appropriately for its purpose) downstream of the wound dressing, and provides the highest resistance in the flow path. This is especially the case where the means for fluid cleansing is a single-phase system, e.g. with ultrafiltration through microapertures or micropores, thus enhancing applied positive pressure to the wound.

Where the device is applied to the fluid in recirculation in the fluid recirculation tube and/or the fluid in the fluid offtake tube downstream of and away from the wound dressing, it will usually apply negative pressure (i.e. below-atmospheric pressure or vacuum) to the wound bed.

Again, often the means for fluid cleansing is (most appropriately for its purpose) downstream of the wound dressing, and provides the highest resistance in the flow path, thus enhancing applied negative pressure to the wound.

The following types of pump may be used as desired:
reciprocating pumps, such as:
    shuttle pumps—with an oscillating shuttle mechanism to move fluids at rates from 2 to 50 ml per minute;
    diaphragm pumps—where pulsations of one or two flexible diaphragms displace liquid while check valves control the direction of the fluid flow.
    piston pumps—where pistons pump fluids through check valves, in particular for positive and/or negative pressure on the wound bed; rotary pumps, such as:
    centrifugal pumps
    flexible impeller
    pumps—where elastomeric impeller traps fluid between impeller blades and a moulded housing that sweeps fluid through the pump housing.
progressing cavity
    pumps—with a cooperating screw rotor and stator, in particular for higher-viscosity and particulate-filled exudate;
    rotary vane pumps—with rotating vaned disk attached to a drive shaft moving fluid without pulsation as it spins. The outlet can be restricted without damaging the pump.
    peristaltic pumps—with peripheral rollers on rotor arms acting on a flexible fluid circulation tube to urge fluid current flow in the tube in the direction of the rotor.
    vacuum pumps—with pressure regulators.

The type and/or capacity of the device will be largely determined by
a) the appropriate or desired fluid volume flow rate of irrigant and/or wound exudate from the wound, and
b) whether it is appropriate or desired to apply a positive or negative pressure to the wound bed, and the level of such pressure to the wound bed for optimum performance of the wound healing process, and by factors such as portability, power consumption and isolation from contamination.

Such a device may also suitably be one that is capable of pulsed, continuous, variable, reversible and/or automated and/or programmable fluid movement. It may in particular be a pump of any of these types.

In practice, even from a wound in a highly exuding state, such a rate of exudate flow is only of the order of up to 75 microliters/$cm^2$/hr (where $cm^2$ refers to the wound area), and the fluid can be highly mobile (owing to the proteases present). Exudate levels drop and consistency changes as the wound heals, e.g. to a level for the same wound that equates to 12.5-25 microliters/$cm^2$/hr.

Where materials deleterious to wound healing are removed by a two-phase system (see below.), such as a dialysis unit, fluid is also potentially lost to the system through the means for fluid cleansing.

This may occur, e.g. through a dialysis polymer film, sheet or membrane which is also permeable to water, in addition to materials deleterious to wound healing.

The balance of fluid in recirculation may thus further decrease, but may be adjusted to minimise this undesired loss in a routine manner as described hereinbefore.

Hence, it will be seen that the circulating fluid from the wound will typically contain a preponderance of irrigant over wound exudate in recirculation from the fluid reservoir.

The type and/or capacity of the device will thus be largely determined in this respect by the appropriate or desired fluid volume flow rate of irrigant, rather than that of exudate, from the wound.

In practice, such a rate of flow of total irrigant and/or wound exudate will be of the order of 1 to 1000, e.g. 3 to 300, and less preferably 1 to 10 ml/cm$^2$/24 hour, where the cm$^2$ refers to the wound area.

The volume of irrigant and/or wound exudate in recirculation may vary over a wide range, but will typically be e.g. 1 to 8 l. (for example for large torso wounds), 200 to 1500 ml (for example for axillary and inguinal wounds), and 0.3 to 300 ml for limb wounds when the therapy is applied in this way.

In practice, suitable pressures are of the order of up to 25% atm such as up to 10% atm. positive or negative pressure on the wound bed, the apparatus being operated as a closed recirculating system.

The higher end of these ranges are potentially more suitable for hospital use, where relatively high % pressures and/or vacua may be used safely under professional supervision.

The lower end is potentially more suitable for home use, where relatively high % pressures and/or vacua cannot be used safely without professional supervision, or for field hospital use.

The device may be a peristaltic pump or diaphragm pump, e.g. preferably a small portable diaphragm or peristaltic pump. These are preferred types of pump, in order in particular to reduce or eliminate contact of internal surfaces and moving parts of the pump with (chronic) wound exudate, and for ease of cleaning.

It may suitably be one that applies positive pressure to the wound and/or the means for fluid cleansing. A preferred pump when the applied pressure is positive is a peristaltic pump, e.g. a small, portable peristaltic pump, mounted upstream of the means for fluid cleansing.

Where the pump is a peristaltic pump, this may be e.g. an Instech Model P720 miniature peristaltic pump, with a flow rate: of 0.2-180 ml/hr and a weight of <0.5 k. This is potentially useful for home and field hospital use.

The pump may suitably be one that applies negative pressure to the wound and/or the means for fluid cleansing.

A preferred pump when the applied pressure is negative is a diaphragm pump, e.g. a small, portable diaphragm pump, mounted downstream of the dressing or the means for fluid cleansing.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as a piezoelectric transducer, a core of a solenoid or a ferromagnetic integer and coil in which the direction of current flow alternates, a rotary cam and follower, and so on.

The outlet from the dressing passes to the means for fluid cleansing for removal of materials deleterious to wound healing from wound exudate, and in turn to the fluid recirculation tube(s).

The apparatus of the invention for aspirating, irrigating and/or cleansing wounds is provided with means for fluid cleansing, which may be a) a single-phase system, such as an ultrafiltration unit, or a chemical absorption and/or adsorption unit; or b) a two-phase system, such as a dialysis unit, or a biphasic extraction unit.

In the former, circulating fluid from the wound and the fluid reservoir passes through a self-contained system in which materials deleterious to wound healing are removed and the cleansed fluid, still containing materials that are beneficial in promoting wound healing are returned to the wound.

The single-phase system may be of any conventional type.

Examples of the means for fluid cleansing in such a system include a macro- or microfiltration unit, which appropriately comprises one or more macroscopic and/or microscopic filters.

These are to retain particulates, e.g. cell debris and microorganisms, allowing proteins and nutrients to pass through.

Alternatively, they also include an ultrafiltration unit, such as a one in which the cleansing integer is a filter for materials deleterious to wound healing, for example a high throughput, low protein-binding polymer film, sheet or membrane which is selectively impermeable to materials deleterious to wound healing, which are removed and the cleansed fluid, still containing materials that are beneficial in promoting wound healing is passed by it.

The membrane may preferably be of a hydrophilic polymeric material, such as a cellulose acetate-nitrate mixture, polyvinylidene chloride, and, for example hydrophilic polyurethane.

Examples of less preferred materials include hydrophobic materials also including polyesters, such as polycarbonates, PTFE, and polyamides, e.g. 6-6 and 6-10, and hydrophobic polyurethanes, and quartz and glass fibre.

It has microapertures or micropores, the maximum cross-dimension of which will largely depend on the species that are to be selectively removed in this way and those to which it is to be permeable.

The former may be removed with microapertures or micropores, e.g. typically with a maximum cross-dimension in the range of 20 to 700 micron, e.g. 20 to 50 nm (for example for undesired proteins), 50 to 100 nm, 100 to 250 nm, 250 to 500 nm and 500 to 700 nm.

The filter integer may be a flat sheet or a membrane of a polymeric material in a more convoluted form, e.g. in the form of elongate structure, such as pipes, tubules, etc.

The system may be a chemical adsorption unit, for example one in which a particulate, such as a zeolite, or a layer, e.g. of a functionalised polymer has sites on its surface that are capable of removing materials deleterious to wound healing on passing the circulating fluid from the wound and the fluid reservoir over them.

The materials may be removed, e.g. by destroying or binding the materials that are deleterious to wound healing, by, for example chelators and/or ion exchangers, degraders, which may be enzymes.

Examples of such also include less specific chemical absorption and/or adsorption units, for example one in which a physical absorbent, such as activated carbon or a zeolite, has non-specific sites on its surface that are capable of removing materials deleterious to wound healing on passing the circulating fluid from the wound and the fluid reservoir over them.

The cleansing integer, for example the polymer film, sheet or other chemical absorption and/or adsorption means, etc should of course be capable of removing materials deleterious to wound healing at a practical rate for a given capacity of the apparatus flow path and the flow rate of irrigant.

In the two-phase system, circulating fluid from the wound and the fluid reservoir in indirect or (less usually, direct) contact with a second fluid (dialysate) phase, more usually a liquid.

Thus, in one form, a biphasic liquid extraction unit, the second fluid phase is (usually) a liquid that is immiscible with the circulating fluid from the dressing, over a surface of which the circulating fluid passes in direct contact with the cleansing fluid. Materials deleterious to wound healing are removed into the dialysate, and the cleansed fluid, still containing materials that are beneficial in promoting wound healing, is returned via the recirculation tube to the wound bed.

Examples of such means for fluid cleansing include those wherein the second fluid (dialysate) phase is perfluorodecalin and like materials Alternatively, where appropriate it may be provided in a form in which the two fluids (recirculation fluid and dialysate) are separated by a significantly two-dimensional integer, for example a polymer film, sheet or membrane or hollow fibre or filament that is permeable to materials in the circulating fluid in the apparatus.

Again, materials deleterious to wound healing are removed into the dialysate, and the cleansed fluid, still containing materials that are beneficial in promoting wound healing, is returned via the recirculation tube to the wound bed.

In either form in which the two-phase system, such as a dialysis unit, is provided, in use typically the dialysate moves past the circulating fluid in the apparatus in a co- or preferably counter-current direction.

Pumps, such as peristaltic pumps, and/or valves control the direction of the two fluid flows.

However, the cleansing fluid may less usually be static, although this may not provide a system with sufficient (dynamic) surface area to remove materials deleterious to wound healing from wound exudate at a practical rate.

Typical dialysate flow rates in a dialytic means for fluid cleansing in the present apparatus for aspirating, irrigating and/or cleansing wounds are those used in the conventional type of two-phase system, such as a dialysis unit for systemic therapy.

The integer may be a film, sheet or membrane, often of the same type, and of the same (generally uniform) thickness, as those used in conventional two-phase system, such as a dialysis unit for systemic therapy.

The film, sheet or membrane may be substantially flat, and depending on any pressure differential across it may require other materials on or in it to stiffen, reinforce or otherwise strengthen it.

However, this may not provide a system with sufficient functional surface area to remove materials deleterious to wound healing from wound exudate at a practical rate.

To be suitable for use, in particular in chronic wound dialysis, with relatively high concentrations of materials that are deleterious to wound healing, it may be advantageous to provide a system in which the film, sheet or membrane of a polymeric material is in the more convoluted form.

This may be in the form of elongate structures, such as pipes, tubes hollow fibres or filaments or tubules of a round cross-section, e.g. elliptical or circular, e.g. in a parallel array with spaces therebetween.

The wound irrigant and/or wound exudate may recirculate through the inside and the cleansing fluid may pass into the spaces between adjacent pipes, tubes or tubules in a co- or preferably counter-current direction, or vice versa.

Again, materials deleterious to wound healing are removed into the dialysate, and the cleansed fluid, still containing materials that are beneficial in promoting wound healing, is returned via the recirculation tube to the wound.

Where the means for fluid cleansing is a two-phase system, e.g. in the form of a dialysis unit, or a biphasic extraction unit, the circulating fluid from the wound and the fluid reservoir passes across one surfaces of a significantly two-dimensional integer, for example a polymer film, sheet or membrane which is selectively permeable to materials deleterious to wound healing.

These are removed by passing a cleansing fluid across the other surface of the integer. The integer may be a film,سheet or membrane that is selectively permeable to the foregoing materials deleterious to wound healing.

Examples of these as above include
oxidants, such as free radicals, e.g. peroxide and superoxide;
iron II and iron III;
all involved in oxidative stress on the wound bed;
proteases, such as serine proteases, e.g. elastase and thrombin; cysteine proteases; matrix metalloproteases, e.g. collagenase; and carboxyl (acid) proteases;
endotoxins, such as lipopolysaccharides;
autoinducer signalling molecules, such as homoserine lactone derivatives, e.g. oxo-alkyl derivatives;
inhibitors of angiogenesis such as thrombospondin-1 (TSP-1), Plasminogen activator inhibitor, or angiostatin (plasminogen fragment)
pro-inflammatory cytokines such as tumour necrosis factor alpha (TNFα.) and interleukin 1 beta (IL-1β), and
inflammatories, such as lipopolysaccharides, and e.g. histamine.

Examples of suitable materials for the film, sheet or membrane (typically in the form of conformable hollow bodies defined by the film, sheet or membrane, such as the structures described hereinbefore) include natural and synthetic polymeric materials.

The membrane may be of one or more hydrophilic polymeric materials, such as a cellulose derivative, e.g. regenerated cellulose, a cellulose mono-, di- or tri-esters, such as cellulose mono-, di- or tri-acetate, benzyl cellulose and Hemophan, and mixtures thereof.

Examples of other materials include hydrophobic materials, such as aromatic polysulphones, polyethersulphones, polyetherether-sulphones, polyketones, polyetherketones and polyetherether-ketones, and sulphonated derivatives thereof, and mixtures thereof.

Examples of other materials include hydrophobic materials, such as polyesters, such as polycarbonates and polyamides, e.g. 6-6 and 6-10; polyacrylates, including, e.g. poly (methyl methacrylate), polyacrylonitrile and copolymers thereof, for example acrylonitrile-sodium metallosulphonate copolymers; and poly(vinylidene chloride).

Suitable materials for the present membranes include thermoplastic polyolefins, such as polyethylene e.g. high-density polyethylene, polypropylene, copolymers thereof, for example with vinyl acetate and polyvinyl alcohol, and mixtures thereof.

The dialysis membrane should have a molecular weight cut off (MWCO) chosen to allow selective perfusion of species deleterious to wound healing that have been targeted for removal from the wound. For example, perfusion of the serine protease elastase (molecular weight 25900 Dalton) would require a membrane with MWCO>25900 Dalton. The MWCO threshold can be varied to suit each application between 1 and 3000000 Dalton.

Preferably, the MWCO should be as close as possible to this weight to exclude interference by larger competitor species.

For example, such a membrane with MWCO>25900 Dalton does not allow any significant amounts of the antagonist to elastase, alpha-1-antitrypsin (AAT) (molecular weight 54000 Dalton), which occurs naturally in wounds, to diffuse freely out of the wound fluid into the dialysate. The inhibitor, which is beneficial in promoting chronic wound healing, remains in contact with the wound bed, and can act beneficially on it, whilst the elastase that is deleterious to wound healing is removed.

Such use of the present apparatus is, e.g. favourable to the wound healing process in chronic wounds, such as diabetic foot ulcers, and especially decubitus pressure ulcers.

As noted hereinafter, antagonists, for example degrading enzymes, or sequestrating agents for elastase on the dialysate side of the membrane, may be used to enhance the removal of this protease from wound exudate.

Where it is desired to remove several different materials that are deleterious to wound healing, it may be advantageous to provide a system of modules in series, each of which removes a different material. This allows incompatible cleansing materials to be used on the same fluid and/or wound exudates.

Preferably any such system is a conventional automated, programmable system which can cleanse the wound irrigant and/or wound exudate with minimal supervision.

As noted above in more detail, fluid passes from a cleansing fluid through a selectively permeable integer.

This may be the typical permeable polymer film, sheet or membrane of a two-phase system, such as a dialysis unit.

Additionally, solutes or disperse phase species will pass from the dialysate into the irrigant and/or wound exudate through the dialysis polymer film, sheet or membrane.

This property may be used to perfuse materials beneficial to wound healing into the irrigant and/or exudate from a dialysate.

In this less conventional type of infusion feed, a broad spectrum of species will usually pass into the exudate and/or irrigant fluid from the dialysate.

These include ionic species, such as bicarbonate;

vitamins, such as ascorbic acid (vitamin C) and vitamin E, and stable derivatives thereof, and mixtures thereof; to relieve oxidative stress on the wound bed;

pH buffering agents, such as potassium dihydrogen phosphate/disodium hydrogen phosphate, local analgesics/anaesthetics, such as lidocainealignocaine hydrochloride and xylocaine (adrenoline lidocaine) and/or anti-inflammatories, to reduce wound pain or inflammation or pain associated with the dressing nutrients to aid proliferation of wound cells, such as amino acids, sugars, low molecular weight tissue building blocks and trace elements; and other cell culture medium species; and gases, such as air, nitrogen, oxygen and/or nitric oxide.

For the purposes of fluid cleansing in the apparatus of the present invention, both the single-phase system, such as an ultrafiltration unit, and two-phase system, such as a dialysis unit, may have captive (non-labile, insoluble and/or immobilised) species such as the following, bound to an insoluble and/or immobilised) substrate over and/or through which the irrigant and/or wound exudate from, the wound dressing passes in turn to the fluid recirculation tube(s):

antioxidants and free radical scavengers, such as 3-hydroxytyramine (dopamine), ascorbic acid (vitamin C), vitamin E and glutathione, and stable derivatives thereof, and mixtures thereof; to relieve oxidative stress on the wound bed;

metal ion chelators and/or ion exchangers, such as transition metal ion chelators, such as iron III chelators (Fe III is involved in oxidative stress on the wound bed.), such as desferrioxamine (DFO), 3-hydroxytyramine (dopamine);

iron III reductants;

protease inhibitors, such as TIMPs and alpha 1-antitrypsin (AAT); serine protease inhibitors, such as 4-(2-aminoethyl)-benzene sulphonyl fluoride (AEBSF, PefaBloc) and Nα-p-tosyl-L-lysine chloro-methyl ketone (TLCK) and ε-aminocaproyl-p-chlorobenzylamide; cysteine protease inhibitors; matrix metalloprotease inhibitors; and carboxyl (acid) protease inhibitors;

sacrificial redox materials that are potentially or actually beneficial in promoting wound healing, by the removal of materials that trigger the expression into wound exudate of redox-sensitive genes that are deleterious to wound healing;

autoinducer signalling molecule degraders, which may be enzymes; and anti-inflammatory materials to bind or destroy lipopolysaccharides, e.g. peptidomimetics Other physiologically active components of the exudate that are deleterious to wound healing may be removed in this way.

These may be removed with suitable chelators and/or ion exchangers, degraders, which may be enzymes, or other species.

The following types of functionalised substrate has sites on its surface that are capable of removing materials deleterious to wound healing on passing the circulating fluid from the wound and the fluid reservoir over them:

heterogeneous resins, for example silica-supported reagents such as:

metal scavengers, 3-(diethylenetriamino)propyl-functionalised silica gel 2-(4-(ethylenediamino)benzene)ethyl-functionalised silica gel 3-(mercapto)propyl-functionalised silica gel 3-(1-thioureido)propyl-functionalised silica gel triamine tetraacetate-functionalised silica gel or electrophilic scavengers, 4-carboxybutyl-functionalised silica gel 4-ethyl benzenesulfonyl chloride-functionalised silica gel propionyl chloride-functionalised silica gel 3-(isocyano)propyl-functionalised silica gel 3-(thiocyano)propyl-functionalised silica gel 3-(2-succinic anhydride)propyl-functionalised silica gel 3-(maleimido)propyl-functionalised silica gel or nucleophilic scavengers, 3-aminopropyl-functionalised silica gel 3-(ethylenediamino)-functionalised silica gel 2-(4-(ethylenediamino)propyl-functionalised silica gel 3-(diethylenetriamino)propyl-functionalised silica gel 4-ethyl-benzenesulfonamide-functionalised silica gel 2-(4-toluenesulfonyl hydrazino)ethyl-functionalised silica gel 3-(mercapto)propyl-functionalised silica gel dimethylsiloxy-functionalised silica gel or base or acid scavengers, 3-(dimethylamino)propyl-functionalised silica gel 3-(1,3,4,6,7,8-hexahydro-2H-pyrimido-[1,2-α]pyrimidino)propyl-functionalised silica gel 3-(1-imidazol-1-yl)propyl-functionalised silica gel 3-(1-morpholino)propyl-functionalised silica gel 3-(1-piperazino)propyl-functionalised silica gel 3-(1-piperidino)propyl-functionalised silica gel 3-(4,4'-trimethyidipiperidino)propyl-functionalised silica gel 2-(2-pyridyl)ethyl-functionalised silica gel 3-(trimethylammonium)propyl-functionalised silica gel or the reagents, 3-(1-cyclohexylcarbodiimido)propyl-functionalised silica gel TEMPO-functionalised silica gel 2-(diphenylphosphino)ethyl-functionalised silica gel 2-(3,4-cyclohexyidiol)propyl-functionalised silica gel 3-(glycidoxy)propyl-functionalised silica gel 2-(3,4-epoxycyclohexyl)propyl-functionalised silica gel
1-(allyl)methyl-functionalised silica gel
4-bromopropyl-functionalised silica gel
4-bromophenyl-functionalised silica gel
3-chloropropyl-functionalised silica gel
4-benzyl chloride-functionalised silica gel
2-(carbomethoxy)propyl-functionalised silica gel
3-(4-nitrobenzamido)propyl-functionalised silica gel
3-(ureido)propyl-functionalised silica gel
or any combinations of the above.

The use of such captive (non-labile, insoluble and/or immobilised) species, such as the foregoing, bound to an insoluble and immobilised) substrate over and/or through which the irrigant and/or wound exudate from, the wound dressing passes has been described hereinbefore as suitable for the means for fluid cleansing.

However, they may additionally, where appropriate, be used in any part of the apparatus that is in contact with the irrigant and/or wound exudate, but often within the dressing, for removal of materials deleterious to wound healing from wound.

The means for fluid cleansing may additionally, where appropriate, comprise one or more macroscopic and/or microscopic filters.

These are to retain particulates, e.g. cell debris and microorganisms, allowing proteins and nutrients to pass through.

Alternatively, a less conventional type of two-phase system (see above), such as a dialysis unit, may be used as the means for fluid cleansing. In this type, the dialysis polymer film, sheet or membrane is not an integer selectively permeable to materials deleterious to wound healing, such as proteases, such as serine proteases, e.g. elastase and thrombin; cysteine protease; matrix metalloproteases, e.g. collagenase; and carboxyl (acid) proteases;

endotoxins, such as lipopolysaccharides;
inhibitors of angiogenesis such as thrombospondin-1 (TSP-1), plasminogen activator inhibitor, or angiostatin (plasminogen fragment);
pro-inflammatory cytokines such as tumour necrosis factor alpha (TNF$\alpha$) and interleukin 1 beta (IL-1$\beta$),
oxidants, such as free radicals, e.g., e.g. peroxide and superoxide; and metal ions, e.g. iron II and iron III, all involved in oxidative stress on the wound bed.

It will however also permit components of the exudate from a wound and/or irrigant fluid that may be larger or smaller molecules, but are beneficially involved in wound healing to pass into and through it.

In the dialysate, or preferably in one or more solid structural integers with at least one surface in contact with the dialysate, in the means for fluid cleansing, there are one or more materials that can remove materials deleterious to wound healing from wound exudate, by being antagonists to such species, for example enzymes or others, such as protease inhibitors, such as serine protease inhibitors, such as 4-(2-aminoethyl)-benzene sulphonyl fluoride (AEBSF, PefaBloc) and N$\alpha$-$\rho$-tosyl-L-lysine chloromethyl ketone (TLCK) and $\epsilon$-aminocaproyl-$\rho$-chlorobenzylamide; cysteine protease inhibitors; matrix metalloprotease inhibitors; and carboxyl (acid) protease inhibitors;

binders and/or degraders, such as anti-inflammatory materials to bind or destroy lipopolysaccharides, e.g. peptidomimetics;
anti-oxidants, such as 3-hydroxytyramine (dopamine), ascorbic acid (vitamin C), vitamin E and glutathione, and stable derivatives thereof, and mixtures thereof; to relieve oxidative stress on the wound bed; and
chelators and/or ion exchanges, such as desferrioxamine (DFO), 3-hydroxytyramine (dopamine), They further include peptides (including cytokines, e.g. bacterial cytokines, such as $\alpha$-amino-$\gamma$-butyrolactone and L-homocarnosine); and sacrificial redox materials that are potentially or actually beneficial in promoting wound healing, such as iron III reductants; and/or regeneratable materials of this type, such as glutathione redox systems; and other physiologically active components.

In use of the two-phase system dialysis unit, of this less conventional type, a broad spectrum of species will usually pass into the dialysate from the exudate.

Some (mainly ionic) species will pass from the dialysate into the irrigant and/or wound exudate through the dialysis polymer film, sheet or membrane that is not very selectively permeable to materials deleterious to wound healing.

The components of the exudate from a wound and/or irrigant fluid will diffuse freely to and fro through it.

If (preferably) none of the dialysate is voided to waste, e.g. to a collection bag, a steady state concentration equilibrium is eventually set up between the dialysate and the irrigant and/or wound exudate, which is 'topped up' from the wound dressing.

Circulating wound fluid aids in the quicker attainment of this equilibrium of materials beneficial in promoting wound healing.

It also returns them to the site where they can be potentially of most benefit, i.e. the wound bed.

The target materials deleterious to wound healing also pass into the dialysate from the exudate through the dialysis polymer film, sheet or membrane that is not very selectively permeable to materials deleterious to wound healing.

Unlike the other components of the exudate from a wound and/or irrigant fluid, the target materials deleterious to wound healing come into contact with the dialysate, or preferably with one or more solid structural integers with at least one surface in the dialysate, and are removed by the appropriate antagonists, binders and/or degraders, chelators and/or ion exchangers and redox agents, etc. The cleansed fluid, still containing some materials that are beneficial in promoting wound healing, is returned to the recirculation tube.

Unlike the other components of the exudate from a wound and/or irrigant fluid the target materials are constantly removed from the dialysate, very little of these species will pass from the dialysate into the irrigant and/or wound exudate, and a steady state concentration equilibrium is not set up, even if the species are constantly 'topped up' from the wound dressing.

It is believed that circulating wound fluid aids in removal from recirculation of the materials deleterious to wound healing from wound exudate, whilst retaining materials that are beneficial in promoting wound healing in contact with the wound.

A particular advantage of this form of the two-phase system, is that where a material that can remove materials deleterious to wound healing from wound exudate is (cyto)toxic or bioincompatible, or not inert to any components that are beneficial in promoting wound healing, the system does not allow any significant amounts of antagonist to diffuse freely out of the dialysate into the irrigant fluid. The active material can act beneficially on the fluid however.

The film sheet or membrane is preferably a dialysis membrane of molecular weight cut off (MWCO) (as conventionally defined) chosen to allow perfusion of species targeted for sequestration or destruction.

For example, sequestration of the serine protease elastase (molecular weight 25900 Dalton) would require a membrane with MWCO>25900 Dalton.

The MWCO threshold can be varied to suit each application between 1 and 3000000 Dalton. Preferably, the MWCO should be as close as possible to this weight to exclude sequestering interference by larger competitor species.

Both the single-phase system, such as an ultrafiltration unit, and two-phase system, such as a dialysis unit, may be in modular form that is relatively easily demountable from the apparatus of the invention. The system may suitably comprise one or more such modules.

The conduits through which respectively
  a) the irrigant and/or wound exudate passes from the wound dressing and
  b) the cleansed fluid, still containing materials that are beneficial in promoting wound healing, is returned to the recirculation tube, and
  c) (in the case where the means is provided in the form of a two-phase system, such as an dialysis unit) through which the cleansing fluid enters and exits the means preferably have means for, on module disconnection and withdrawal,
    i) switching off the flow and
    ii) providing an immediate fluid-tight seal or closure over the ends of the conduits and the cooperating tubes in the rest of the apparatus of the invention so exposed,
to prevent continuing passage of irrigant and/or exudate and cleansed fluid, and cleansing fluid.

The apparatus of the invention for aspirating, irrigating and/or cleansing wounds is provided with means for bleeding the offtake and/or recirculation tubes, such as a regulator, such as a valve or other control device for bleeding fluids from the wound.

The device for moving fluid through the wound and means for fluid cleansing is used to move irrigant to the wound dressing and apply the desired positive or negative pressure on the wound bed.

The desired balance of fluid in recirculation tube will typically be regulated by means of
  a) the means for bleeding the offtake and/or recirculation tubes,
  b) the means for flow switching between supply and recirculation, and/or
  c) the means for moving fluid over the wound bed and through the means for fluid cleansing,
as appropriate.

Thus, e.g. if
  a) the apparatus for aspirating, irrigating and/or cleansing wounds is a single-phase system, such as an ultrafiltration unit,
  b) the wound is not in a highly exuding state and
  c) it is not appropriate or desired to admit fluid into the wound from the fluid reservoir,
there is no or negligible change in the balance of fluid in recirculation.

Once it has been primed throughout, e.g. to the desired positive or negative pressure on the wound bed, the apparatus may be operated as a closed recirculating system.

The means for flow switching between supply and recirculation tubes is set to close the wound to the fluid reservoir via the fluid supply tube, and the means for bleeding the offtake and/or recirculation tubes are also closed.

If
  a) the apparatus for aspirating, irrigating and/or cleansing wounds is a single-phase system, such as an ultrafiltration unit,
  b) the wound is in a highly exuding state and/or
  c) it is appropriate or desired to admit fluid into the wound from the fluid reservoir,
there is a positive change in the balance of fluid in recirculation.

Once it has been primed throughout, e.g. to the desired positive or negative pressure on the wound bed, the apparatus cannot be operated as a closed recirculating system, without the pressure to the wound bed increasing, possibly undesirably.

The means for bleeding the offtake and/or recirculation tubes must be opened to some extent to relieve positive pressure on the wound bed. The bleed-off may be voided to waste, e.g. to a collection bag.

Materials that are beneficial in promoting wound healing may be lost to the site where they can be potentially of most benefit, i.e. the wound bed, when the therapy is applied in this way.

However, the balance of fluid in recirculation may be routinely adjusted to minimise this undesired loss.

The factors that determine the balance of fluid in recirculation in an apparatus with a two-phase system means for fluid cleansing in the form of a dialysis unit, or a biphasic extraction unit have been described hereinbefore in detail hereinbefore in connection with the operation of the apparatus. It is sufficient to note here that at some point after steady state recirculation established through the length of the apparatus flow path, it may be necessary that any bleed valve is opened, if overall the fluid level is increasing by transfer from the dialysate to an undesirable extent.

Other combinations, and the necessary adjustments to maintain the desired balance of fluid in recirculation tube by means of
  a) the means for bleeding the offtake and/or recirculation tubes,
  b) the means for flow switching between supply and recirculation, and/or
  c) the means for moving fluid
will be apparent to the skilled person.

The outlet from the means for bleeding the offtake and/or recirculation tubes may be collected and monitored and used to diagnose the status of the wound and/or its exudate.

The waste reservoir may be of any conventional type, e.g. a tube, bag (such as a bag typically used as an ostomy bag), chamber, pouch or other structure, e.g. of polymer film, which can contain the irrigant fluid that has been bled off. In all embodiments of the apparatus, the type and material of the waste reservoir will be largely determined by its function. To be suitable for use, the material need only be fluid-impermeable once in use, and flexible.

Examples of suitable materials for the fluid reservoir include synthetic polymeric materials, such as polyolefins, such as poly (vinylidene chloride).

Suitable materials for the present purpose also include polyethylene, e.g. high-density polyethylene, polypropylene, copolymers thereof, for example with vinyl acetate and mixtures thereof.

In a second aspect of the present invention there is provided a conformable wound dressing, characterised in that it comprises a backing layer with a wound-facing face which is capable of forming a relatively fluid-tight seal or closure over a wound and has
  at least one inlet pipe for connection to a fluid supply tube, which passes through and/or under the wound-facing face, and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure over the wound.

The dressing is advantageously provided for use in a bacteria-proof pouch.

Examples of suitable forms of such wound dressings are as described by way of example hereinbefore.

It is desirable a) to obviate at least some of the disadvantages of known aspiration and/or irrigation therapies, and b) to provide a system of therapy which i) can remove materials deleterious to wound healing from wound exudate, whilst retaining materials that are beneficial in promoting wound healing in contact with the wound bed, and/or ii) which allows fluids containing active amounts of materials that are beneficial in promoting wound healing to pass into and/or through the wound in contact with the wound bed.

Thus, in a third aspect of the present invention there is provided a method of treating wounds to promote wound healing using the apparatus for aspirating, irrigating and/or cleansing wounds of the present invention.

BRIEF DESCRIPTION OF THE DRAWINGS

The present invention will now be described by way of example only with reference to the accompanying drawings in which.

It has a single-phase system means for fluid cleansing in the form of an ultrafiltration unit.

Figure 2:
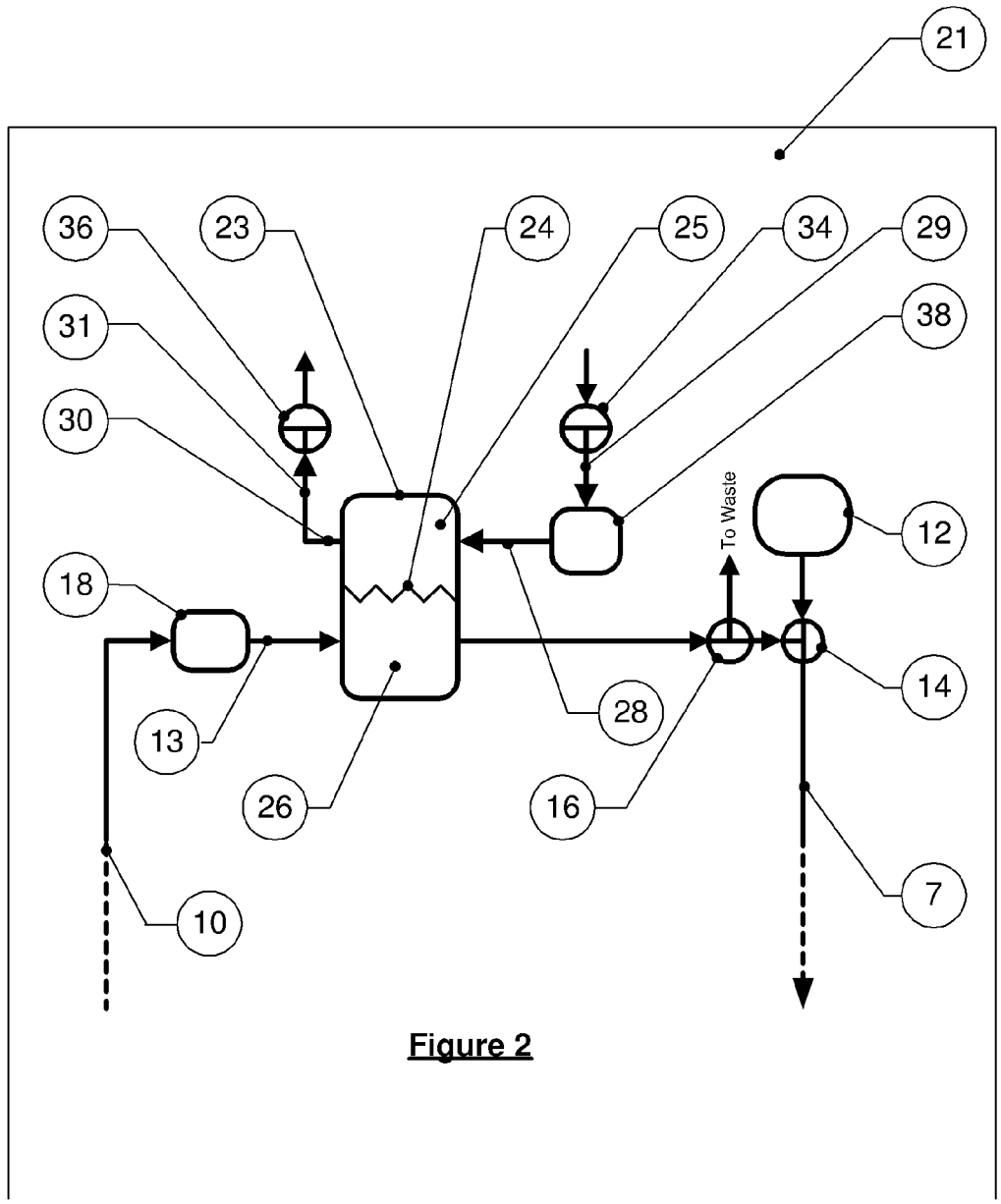

FIG. 2 is a schematic view of an apparatus for aspirating, irrigating and/or cleansing a wound according to the first aspect of the present invention.

It has a two-phase system means for fluid cleansing in the form of a dialysis unit, or a biphasic extraction unit.

FIGS. 3 to 7 are cross-sectional views of conformable wound dressings, of the second aspect of the present invention for aspirating and/or irrigating wounds.

Figure 3A:
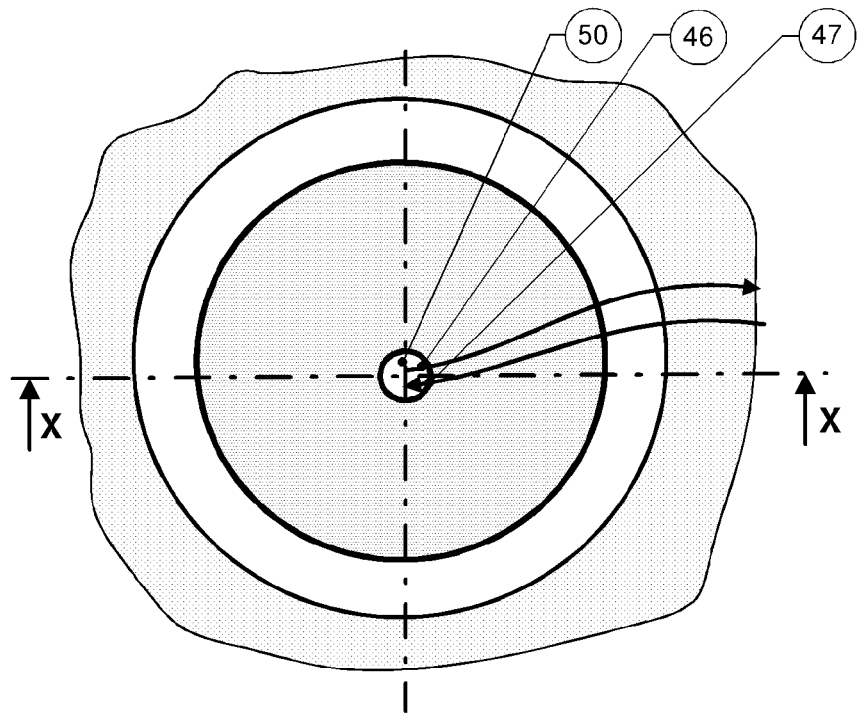
Figure 3B:
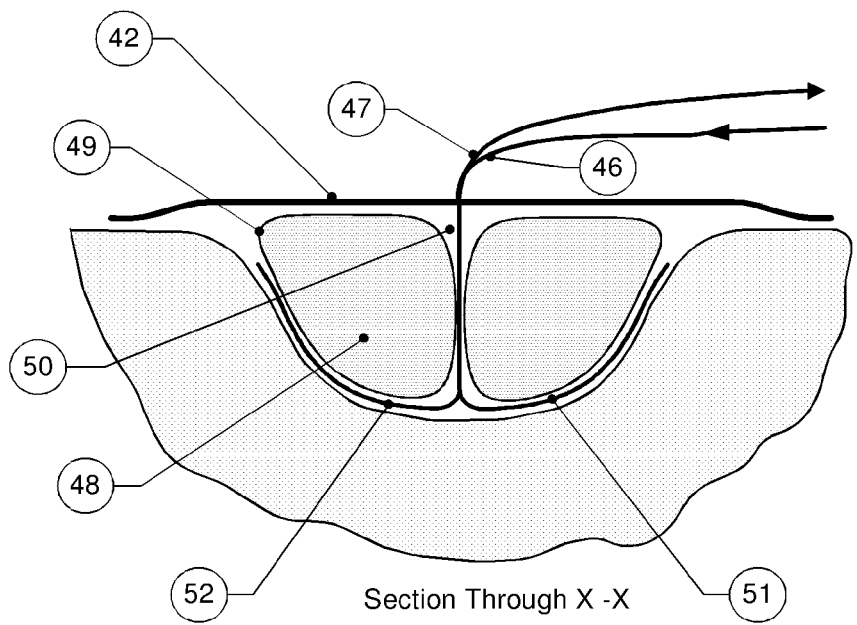

FIG. 3 includes two views illustrated in FIGS. 3a and 3b.

Figure 4A:
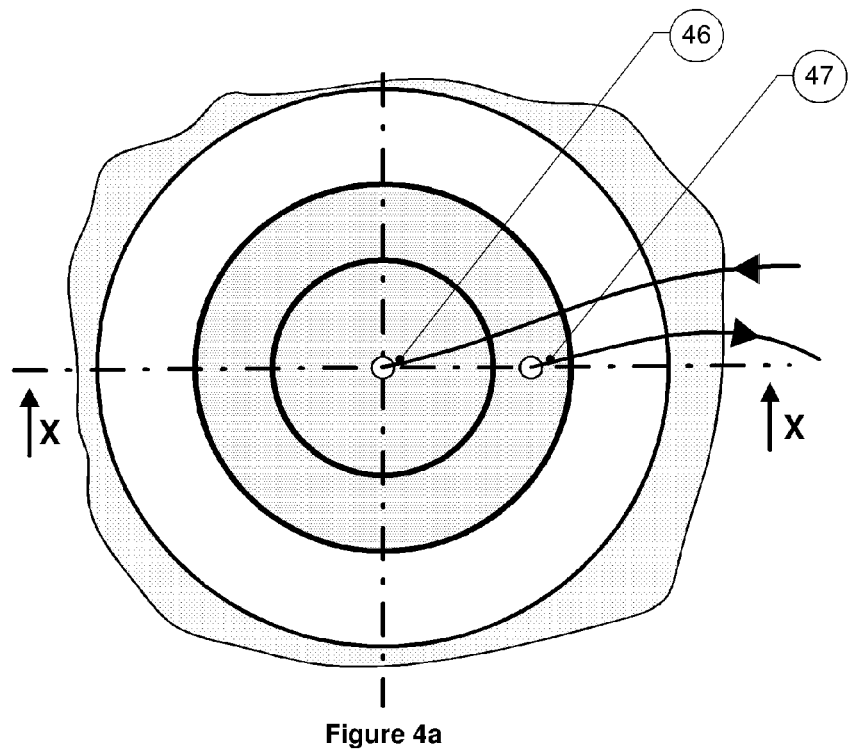
Figure 4B:
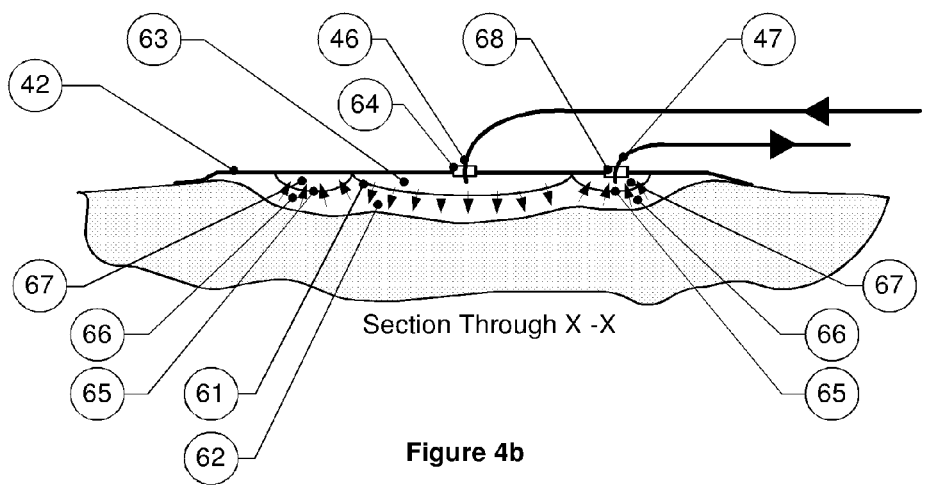

FIG. 4 includes two views illustrated in FIGS. 4a and 4b.

Figure 5A:
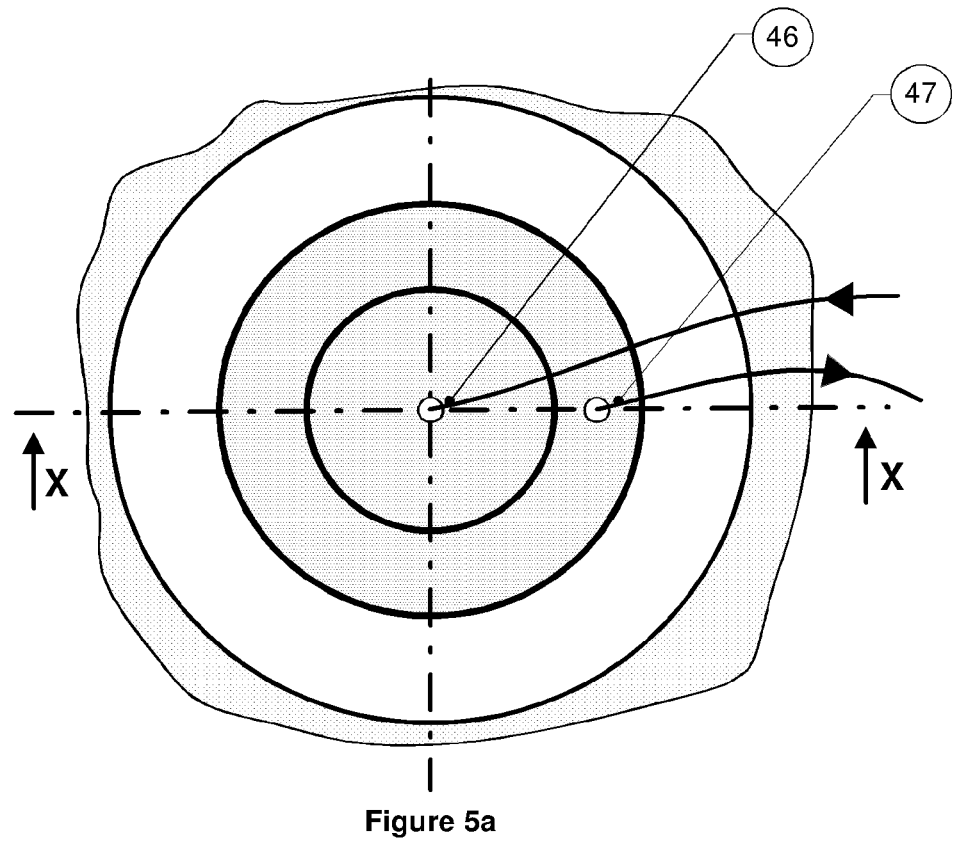
Figure 5B:
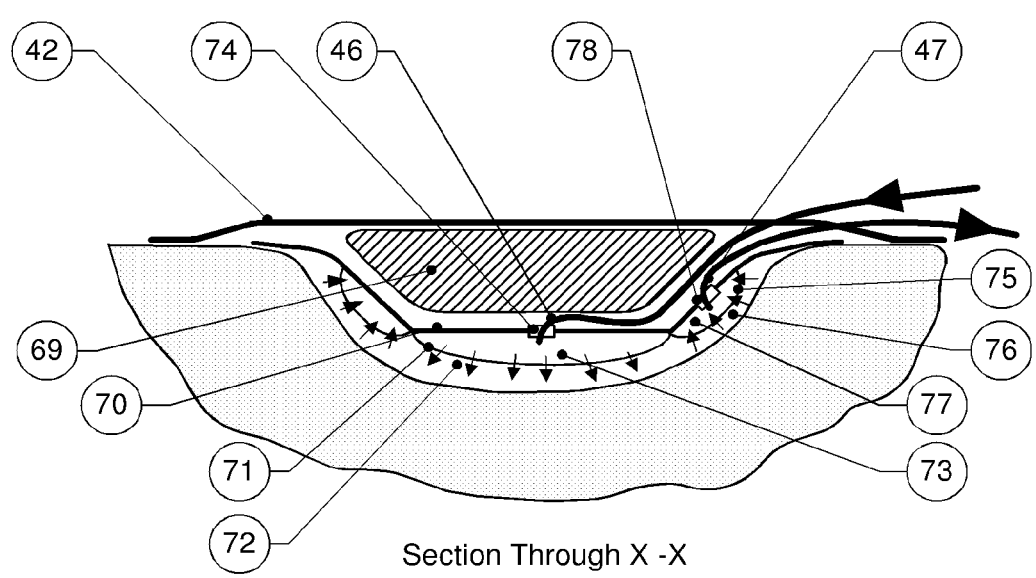

FIG. 5 includes two views illustrated in FIGS. 5a and 5b.

Figure 6A:
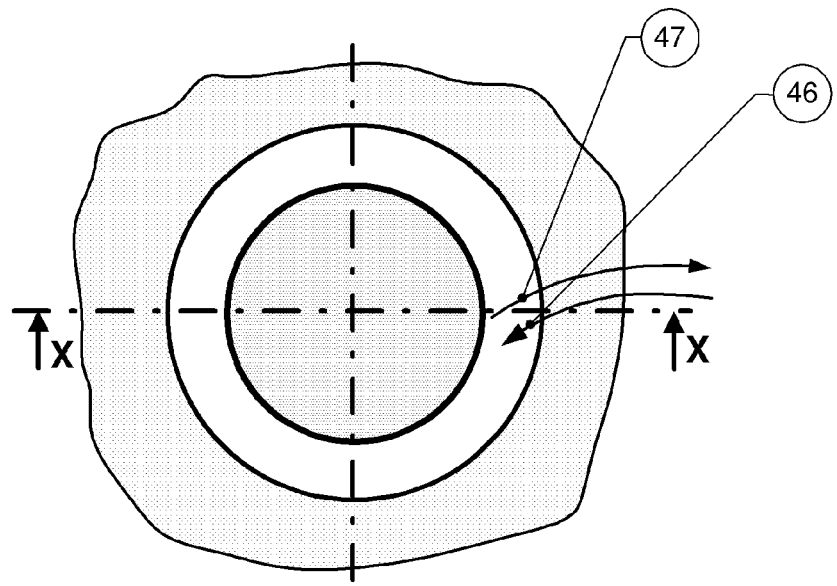
Figure 6B:
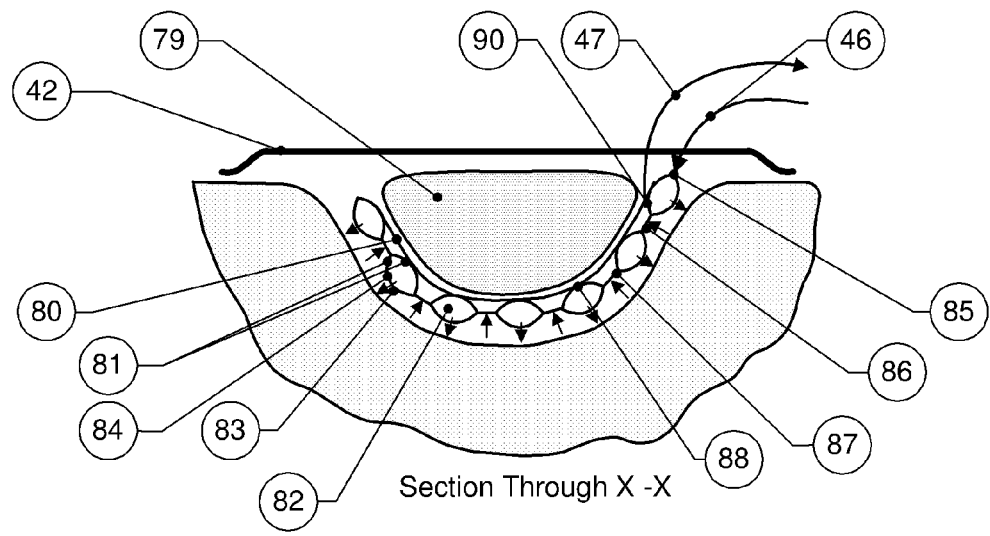

FIG. 6 includes two views illustrated in FIGS. 6a and 6b.

Figure 7A:
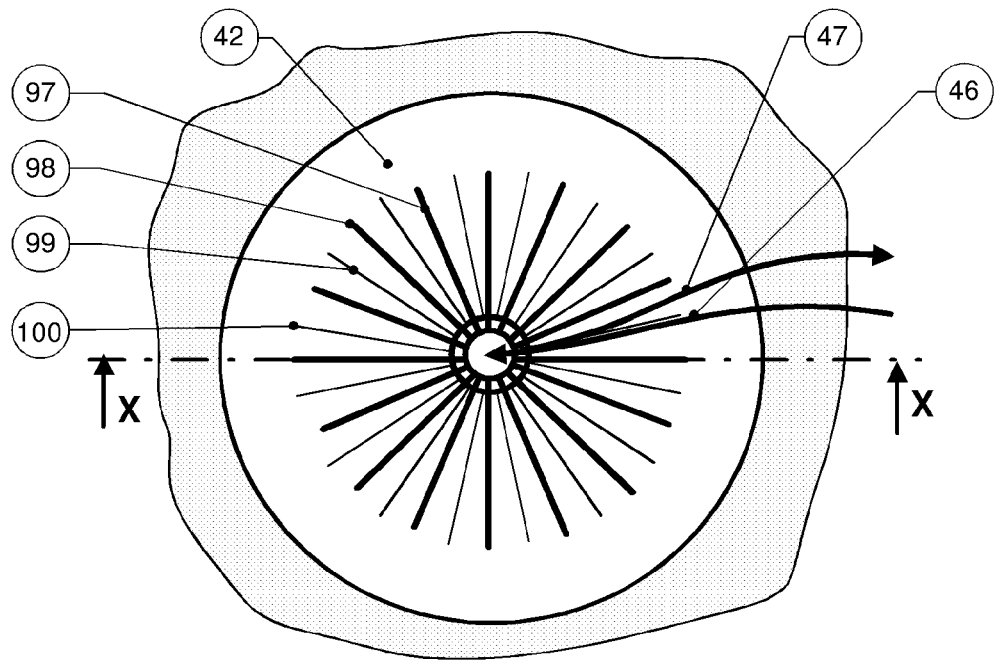
Figure 7B:
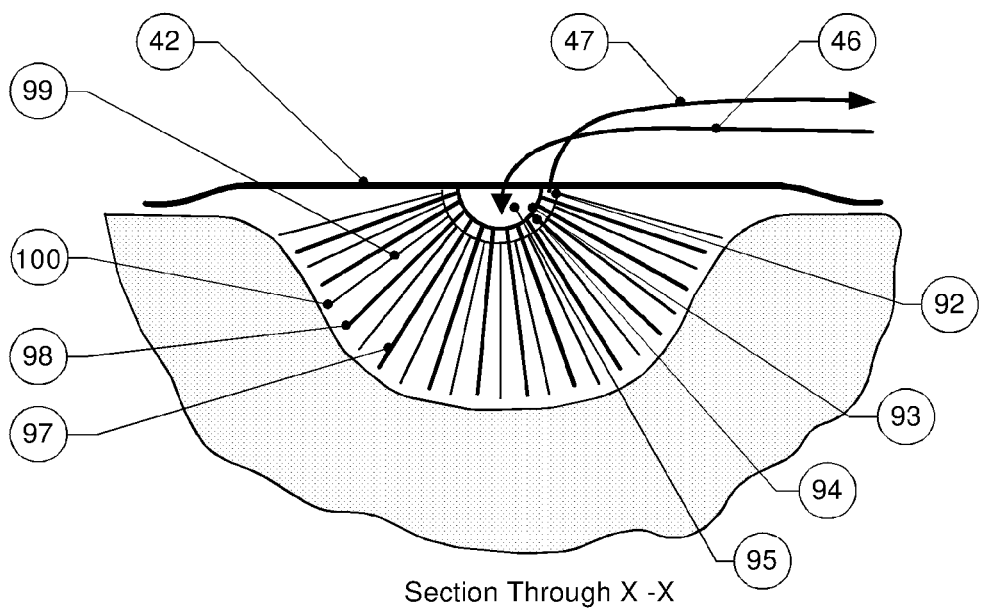

FIG. 7 includes two views illustrated in FIGS. 7a and 7b.

In these, FIGS. 3a to 7a are cross-sectional plan views of the wound dressings, and FIGS. 3b to 7b are cross-sectional side views of the wound dressings.

FIGS. 8 to 10 are various views of inlet and outlet manifold layouts for the wound dressings of the second aspect of the present invention for respectively delivering fluid to, and collecting fluid from, the wound.

FIG. 8 includes four views illustrated in FIGS. 8a, 8b, 8c, and 8d.

Figure 9A:
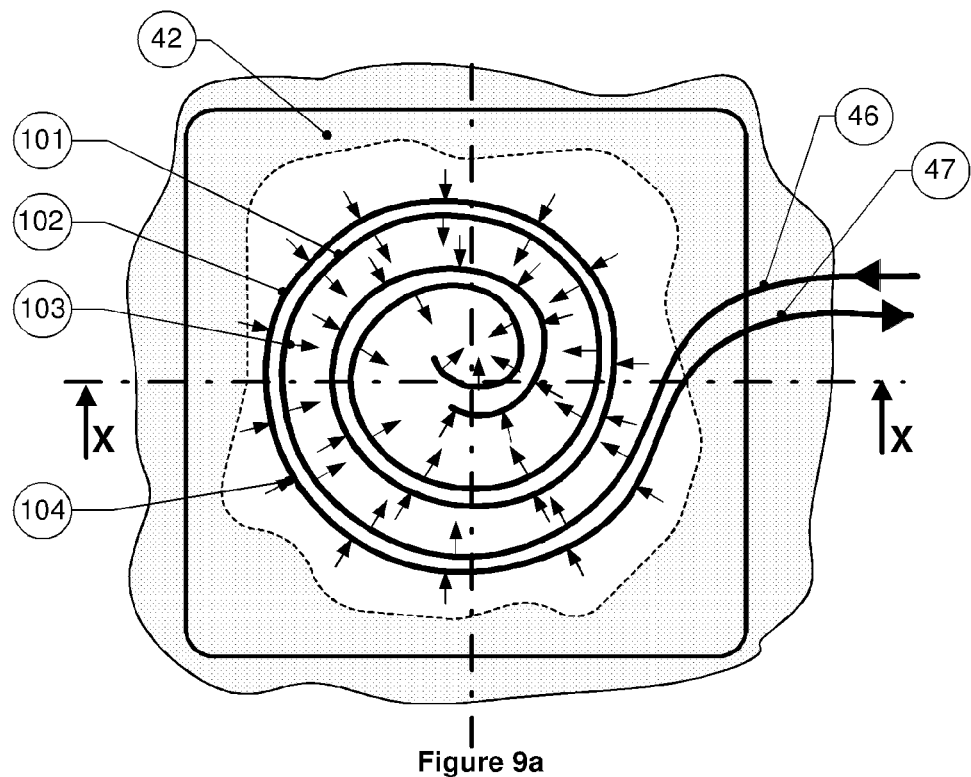
Figure 9B:
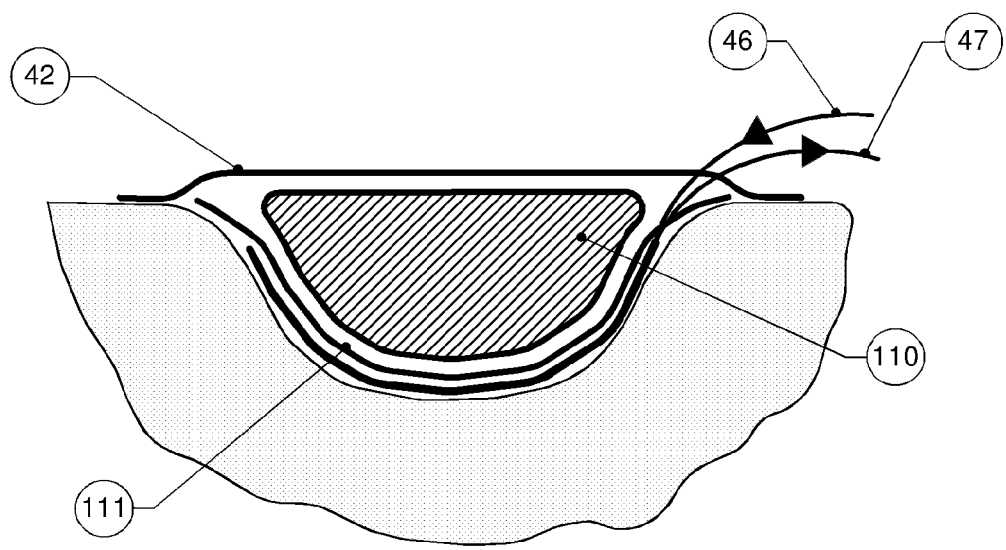

FIG. 9 includes two views illustrated in FIGS. 9a and 9b.

Figures 10A, 10B, 10C:
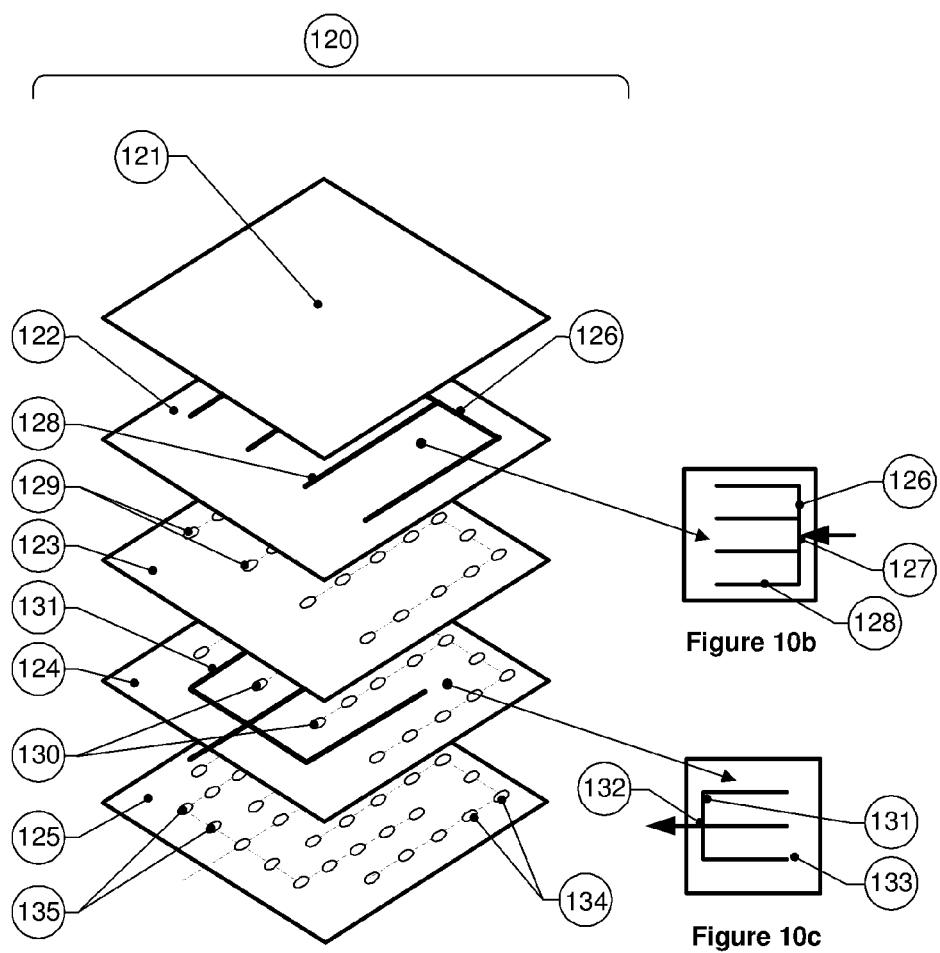

FIG. 10 includes three views illustrated in FIGS. 10a, 10b, and 10c.

Figure 11:
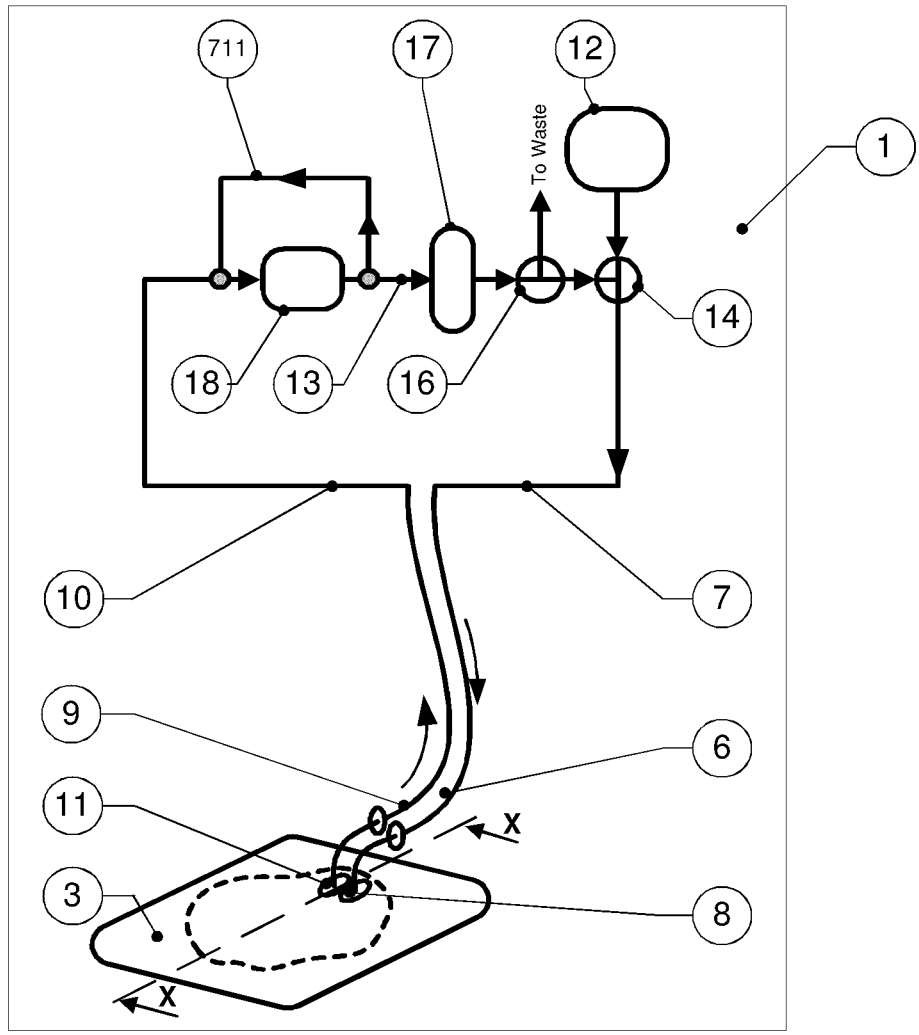

FIG. 11 is a schematic view of an apparatus for aspirating, irrigating and/or cleansing a wound according to the first aspect of the present invention.

It has a single-phase system means for fluid cleansing in the form of an ultrafiltration unit.

Figure 12:
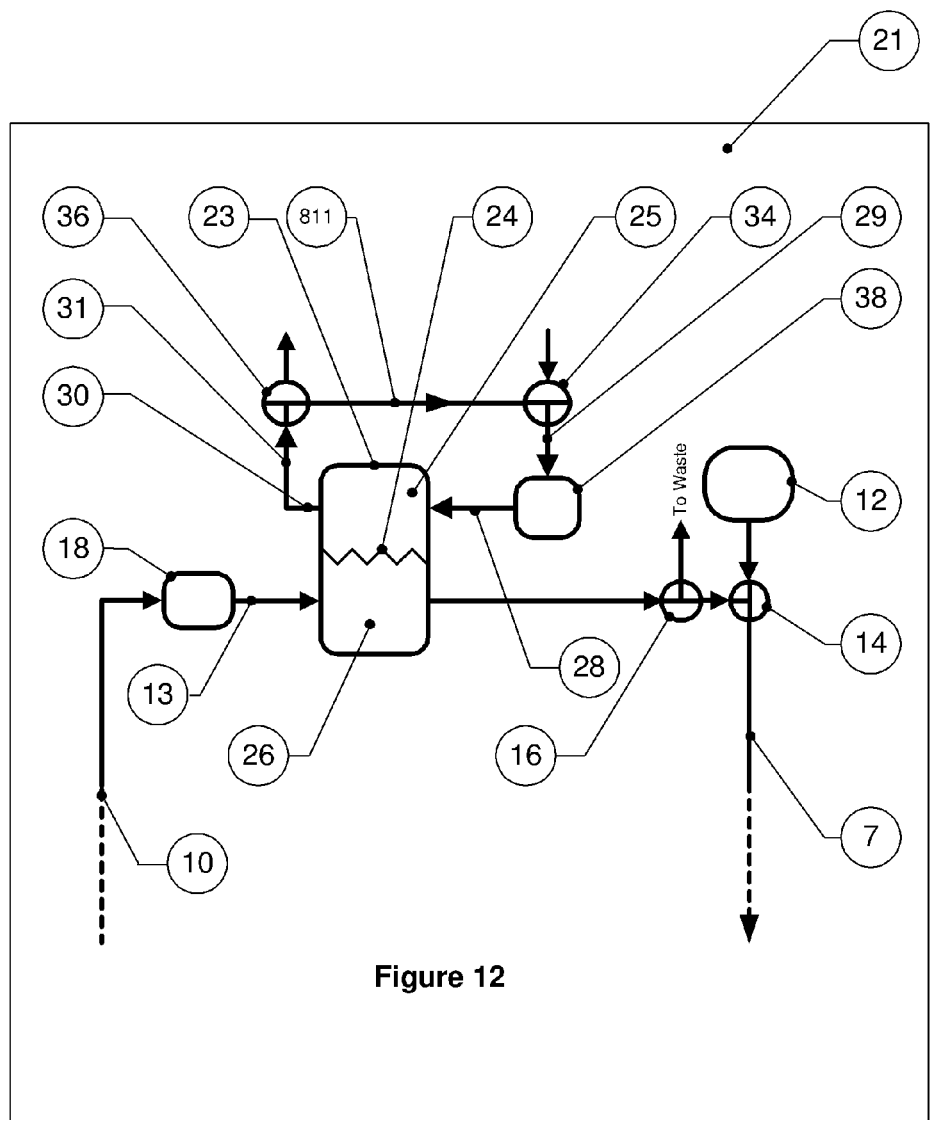

FIG. 12 is a schematic view of an apparatus for aspirating, irrigating and/or cleansing a wound according to the first aspect of the present invention.

It has a two-phase system means for fluid cleansing in the form of a dialysis unit, or a biphasic extraction unit.

FIGS. 13 to 26 are cross-sectional views of conformable wound dressings, of the second aspect of the present invention for aspirating and/or irrigating wounds.

Figure 13A:
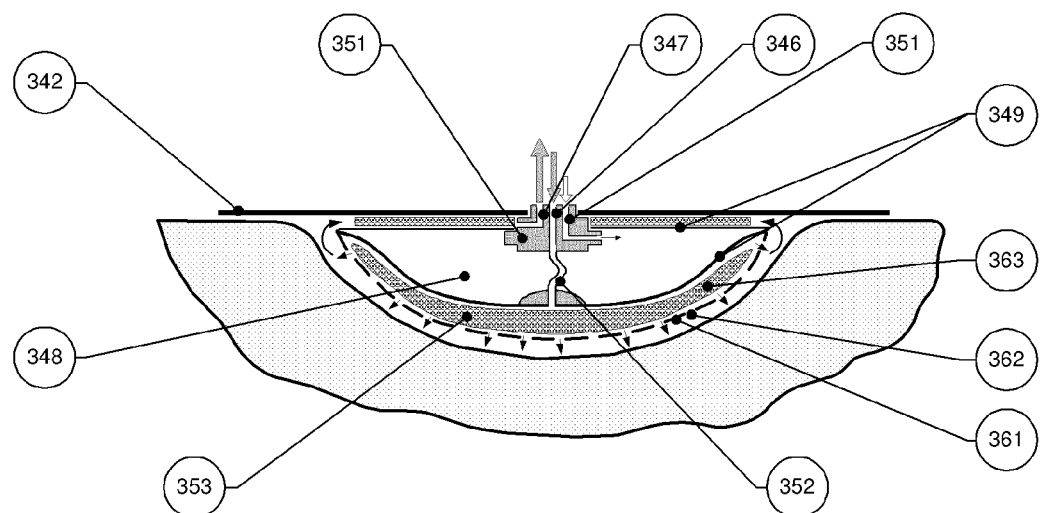
Figure 13B:
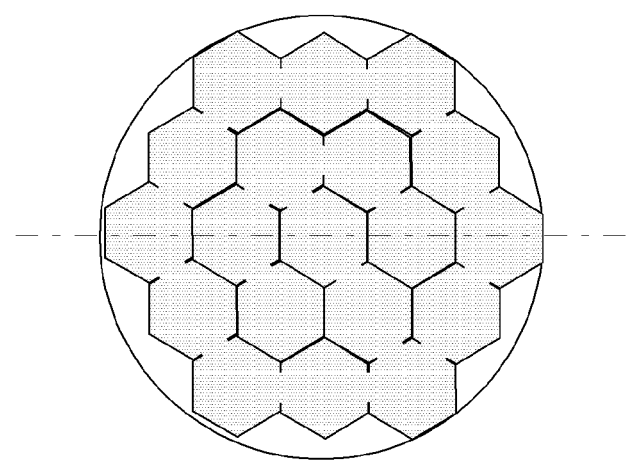

FIG. 13 includes two views illustrated in FIGS. 13a and 13b.

Figure 16A:
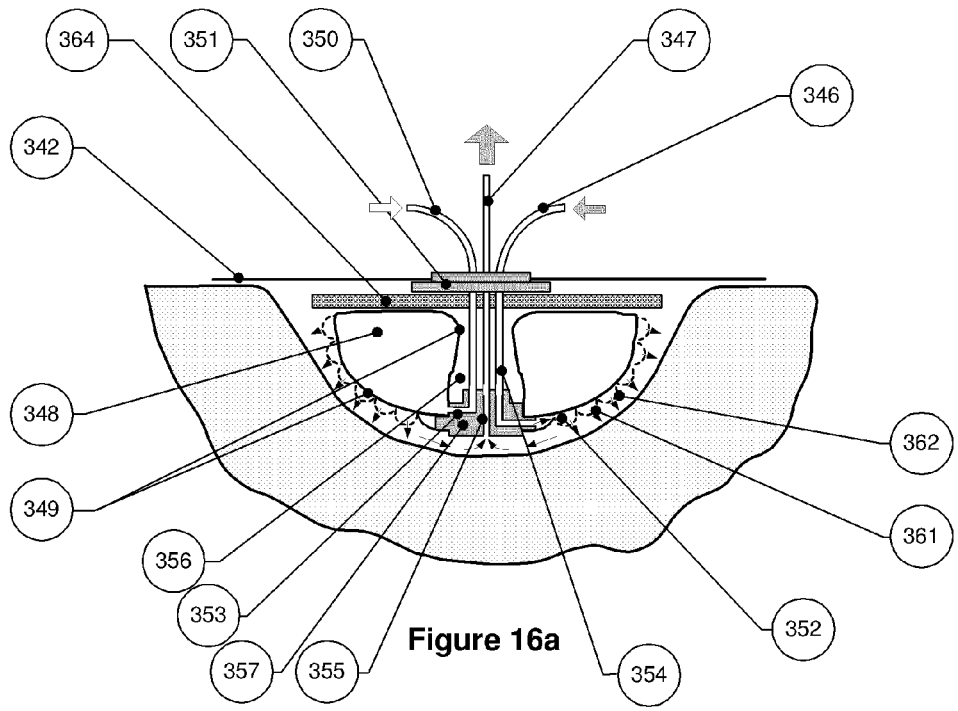
Figure 16B:
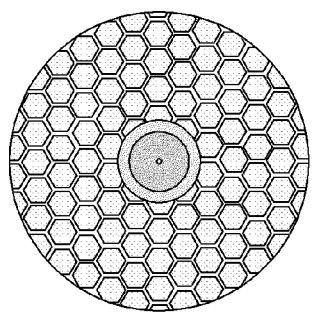

FIG. 16 includes two views illustrated in FIGS. 16a and 16b.

Figure 18A:
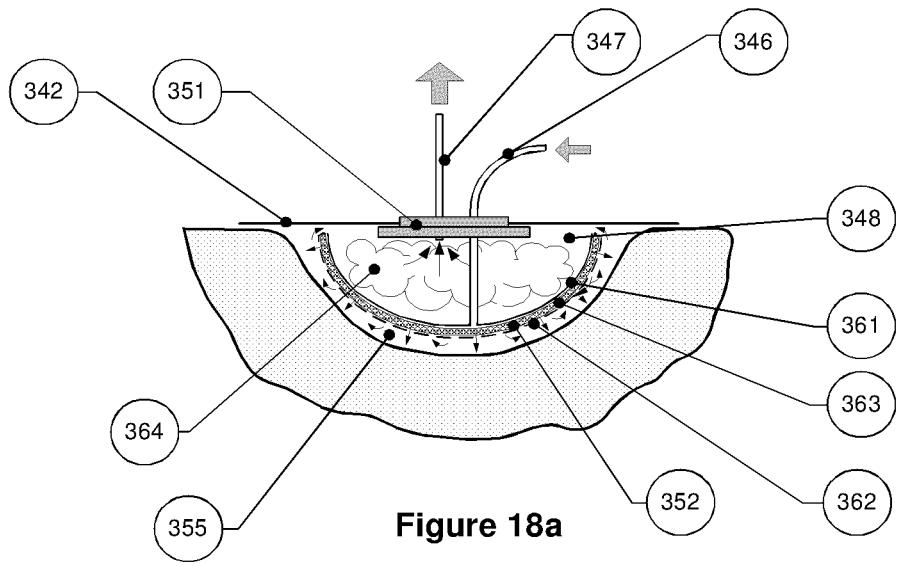
Figure 18B:
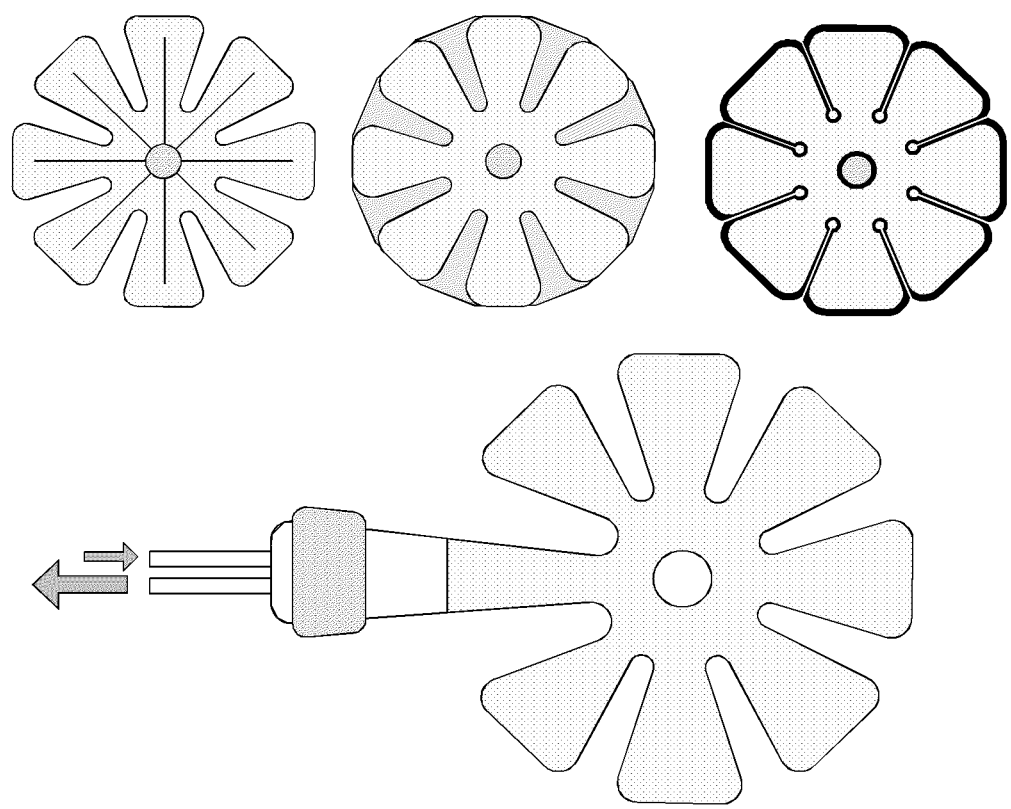

FIG. 18 includes two views illustrated in FIGS. 18a and 18b.

Figure 27:
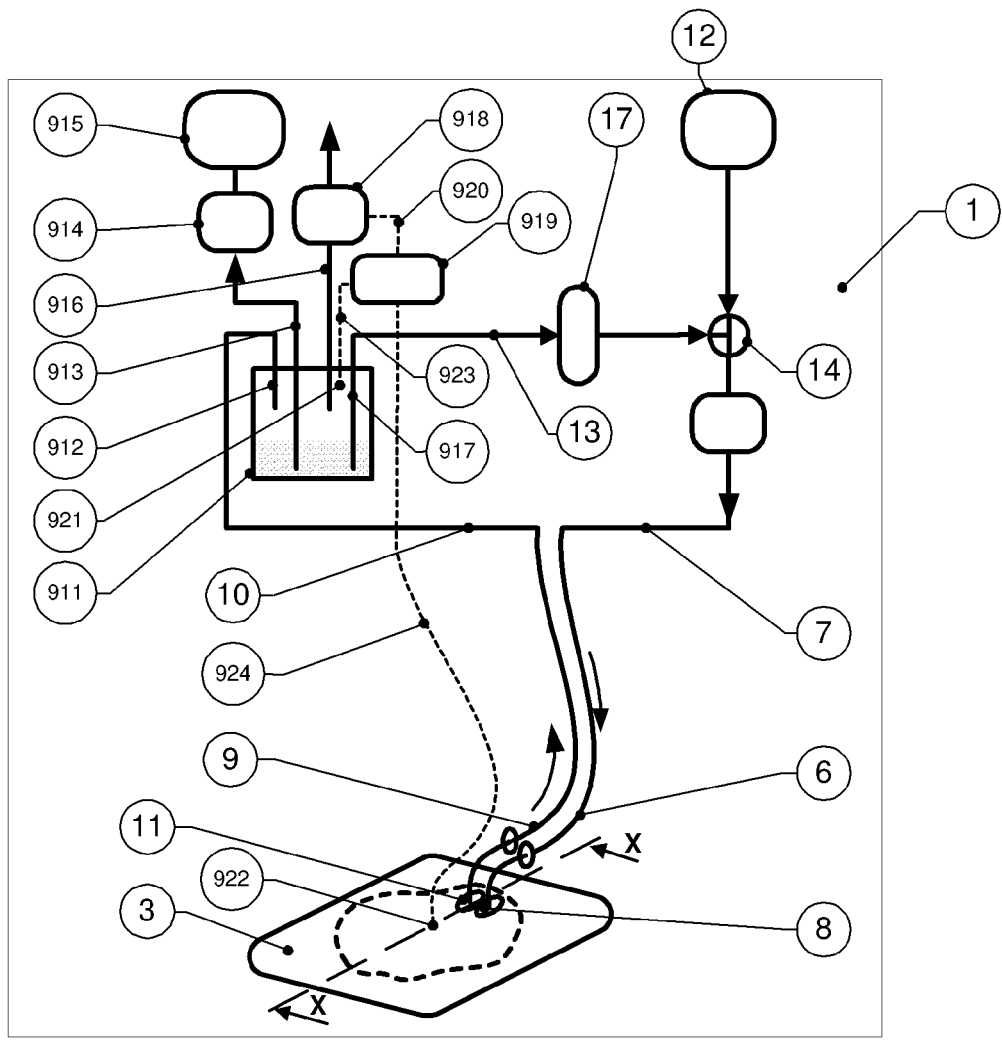
Figure 27:
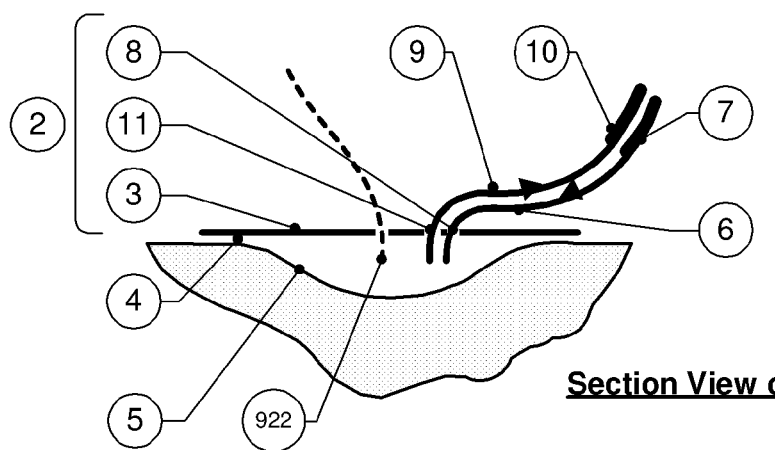

FIG. 27 is a schematic view of another apparatus for aspirating, irrigating and/or cleansing a wound according to the first aspect of the present invention.

It has a single-phase system means for fluid cleansing in the form of an ultrafiltration unit.

DETAILED DESCRIPTION OF THE PREFERRED EMBODIMENT

Figure 1:
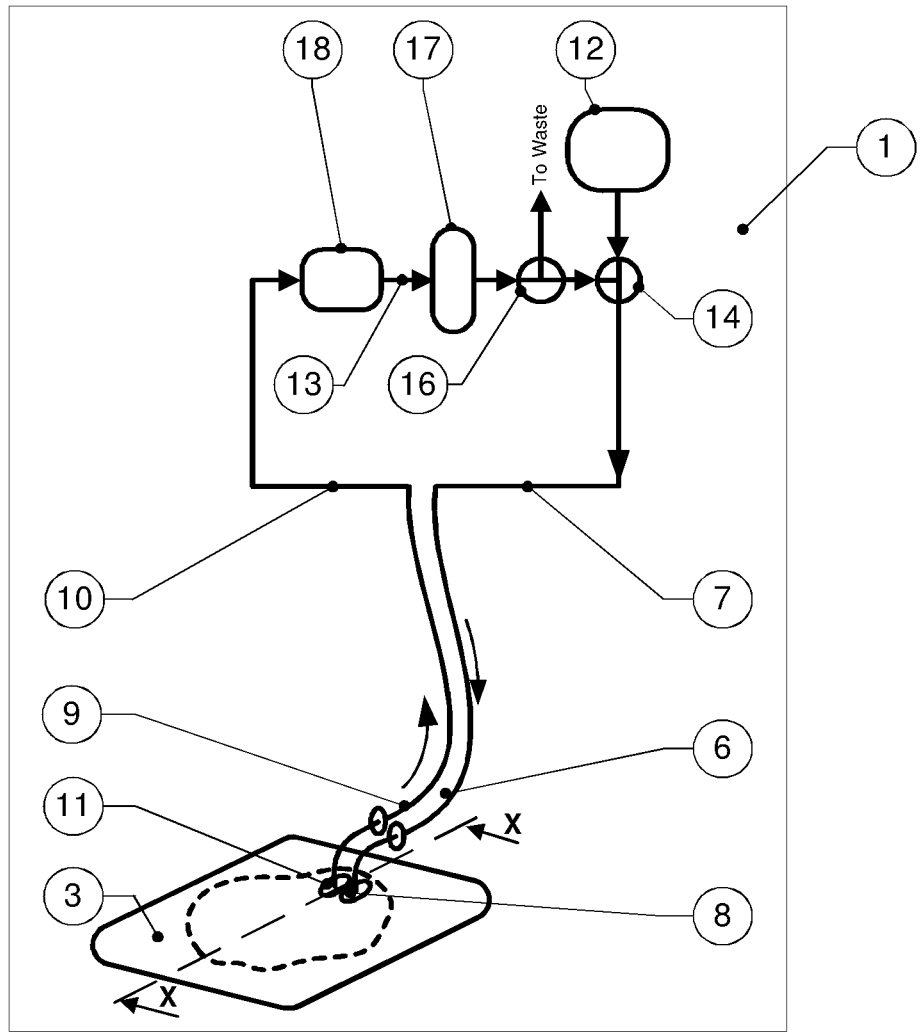
FIG. 1 is a schematic view of an apparatus for aspirating, irrigating and/or cleansing a wound according to the first aspect of the present invention.
Figure 1:
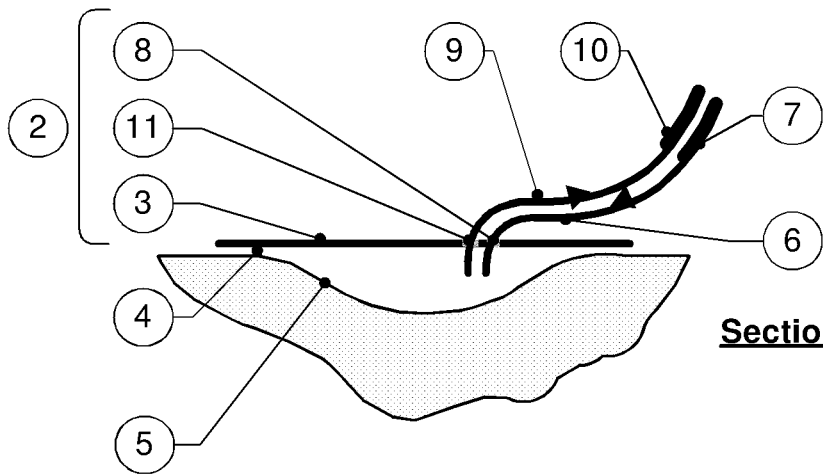

Referring to FIG. 1, the apparatus (1) for aspirating, irrigating and/or cleansing wounds comprises a conformable wound dressing (2), having a backing layer (3) which is capable of forming a relatively fluid-tight seal or closure (4) over a wound (5) and one inlet pipe (6) for connection to a fluid supply tube (7), which passes through the wound-facing face of the backing layer (5) at (8), and one outlet pipe (9) for connection to a fluid offtake tube (10), which passes through the wound-facing face at (11), the points (8), (11) at which the inlet pipe and the outlet pipe passes through and/or under the wound-facing face forming a relatively fluid-tight seal or closure over the wound, the inlet pipe being connected via means for flow switching between supply and recirculation, here a T-valve (14), by the fluid supply tube (7) to a fluid reservoir (12) and to a fluid recirculation tube (13) having a means for bleeding the tube, here a bleed T-valve (16) to waste, e.g. to a collection bag (not shown), the outlet pipe (9) being connected to a fluid offtake tube (10), connected in turn to means for fluid cleansing (17), here in the form of an ultrafiltration unit, connected to the inlet pipe (6) via the fluid recirculation tube (13) and T-valve (14), and a device for moving fluid through the wound and means for fluid cleansing (17), here a peristaltic pump (18), e.g. preferably a small portable peristaltic pump, acting on the fluid circulation tube (13) with the peripheral rollers on its rotor (not shown) to apply a low negative pressure on the wound.

The ultrafiltration unit (17) is a single-phase system. In this the circulating fluid from the wound and the fluid reservoir passes through a self-contained system in which materials deleterious to wound healing are removed and the cleansed fluid, still containing materials that are beneficial in promoting wound healing, is returned via the recirculation tube to the wound bed.

(In a variant of this apparatus, there are two inlet pipes (6), which are connected respectively to a fluid supply tube (7) and fluid recirculation tube (13), respectively having a first valve (19) for admitting fluid into the wound from the fluid reservoir (12) and a second valve (20) for admitting fluid into the wound from the recirculation tube.

Usually in use of the apparatus, when the first valve (19) is open, the second valve (20) is shut, and vice versa.)

In use of the apparatus (1), the valve (16) is opened to a collection bag (not shown), and the T-valve (14) is turned to admit fluid from the fluid reservoir to the wound dressing through the fluid supply tube (7) and inlet pipe (6). (In the variant of this apparatus having two inlet pipes (6), which are connected respectively to a fluid supply tube (7) and fluid recirculation tube (13), the first valve (19) for admitting fluid into the wound from the fluid reservoir (12) is opened and the second valve (20) is shut, and vice versa.)

The pump (18) is started to nip the fluid recirculation tube (13) with the peripheral rollers on its rotor (not shown) to apply a low positive pressure on the wound. It is allowed to run until the apparatus is primed throughout the whole length of the apparatus flow path and excess fluid is voided to waste via the bleed T-valve (16) into the collection bag (not shown).

The T-valve (14) is then turned to switch from supply and recirculation, i.e. is set to close the wound to the fluid reservoir (12) but to admit fluid into the wound from the fluid recirculation tube (13), and the bleed T-valve (16) is simultaneously closed.

(In the variant of this apparatus, where there are two inlet pipes (6), which are connected respectively to a fluid supply tube (7) and fluid recirculation tube (13), the first valve (19) is closed and a recirculating system set up by opening the second valve (20) for admitting fluid into the wound from the recirculation tube (13).

The circulating fluid from the wound and the fluid reservoir (12) passes through the ultrafiltration unit (17). Materials deleterious to wound healing are removed and the cleansed fluid, still containing materials that are beneficial in promoting wound healing, is returned via the recirculation tube (13) to the wound bed.

The recirculation of fluid may be continued as long as desired.

Switching between supply and recirculation is then reversed, by turning the T-valve (14) to admit fluid from the fluid reservoir to the wound dressing through the fluid supply tube (7) and inlet pipe (6).

(In the variant of this apparatus having two inlet pipes (6), which are connected respectively to a fluid supply tube (7) and fluid recirculation tube (13), the first valve (19) for admitting fluid into the wound from the fluid reservoir (12) is opened and the second valve (20) is shut, and vice versa.)

The bleed valve (16) is simultaneously opened, so that fresh fluid flushes the recirculating system.

The running of the pump (18) may be continued until the apparatus is flushed, when it and the fluid recirculation is stopped.

If, e.g. the wound is in a highly exuding state, there is a positive change in the balance of fluid in recirculation. It may be necessary to bleed fluid from recirculation, by opening the bleed T-valve (16) to bleed fluid from the recirculation tube (13).

Referring to FIG. 2, the apparatus (21) is a variant of that of FIG. 1, with identical, and identically numbered, components, except for the means for fluid cleansing, which is in the form of a two-phase system, here a dialysis unit (23).

In this, there is one system through which the circulating fluid from the wound and the fluid reservoir passes and from which deleterious materials are removed by selectively permeable contact with a second system, through which passes a cleansing fluid.

The dialysis unit (23) thus has an internal polymer film, sheet or membrane (24), selectively permeable to materials deleterious to wound healing, which divides it into
 a) a first chamber (25), through which passes a cleansing fluid across one surface of the polymer film, sheet or membrane, and
 b) a second chamber (26), through which passes the circulating fluid from the wound and the fluid reservoir (12), and from which deleterious materials are removed The dialysis unit (23) thus has a dialysate inlet pipe (28) connecting to a dialysate supply tube (29) which passes to a peristaltic pump (38), e.g. preferably a small portable peristaltic pump, acting on the dialysate supply tube (29) with the peripheral rollers on its rotor (not shown) to supply cleansing fluid across the surface of the polymer film, sheet or membrane (28) in the first chamber (25) from a dialysate reservoir (not shown) via a valve (34).

The dialysis unit (23) also has a dialysate outlet pipe (30) connecting to a dialysate outlet tube (31) which passes to waste via a second bleed T-valve (36) into, e.g. a collection bag (not shown).

Operation of this apparatus is similar to that of FIG. 1, except for the dialysis unit (23), in that at some point after the irrigation system is primed and steady state recirculation established through the length of the apparatus flow path, the valve (34) and second bleed valve (36) are opened.

The pump (38) is started to nip fluid dialysate tube (29) with the peripheral rollers on its rotor (not shown) to pump cleansing fluid to the first chamber from a dialysate reservoir (not shown) and out to waste via the bleed valve (36) into the collection bag (not shown).

The dialysis unit (23) is a module (or scrubbing cartridge) with a substrate that changes colour to indicate the presence of detrimental factors in the cleansed fluid, and that the scrubbing cartridge is exhausted and should be renewed.

Referring to FIGS. 3 to 6, each dressing (41) is in the form of a conformable body defined by a microbe-impermeable film backing layer (42) with a uniform thickness of 25 micron, with a wound-facing face (43) which is capable of forming a relatively fluid-tight seal or closure over a wound. FIG. 3 includes two views illustrated in FIGS. 3a and 3b. FIG. 4 includes two views illustrated in FIGS. 4a and 4b. FIG. 5 includes two views illustrated in FIGS. 5a and 5b. FIG. 6 includes two views illustrated in FIGS. 6a and 6b. FIG. 7 includes two views illustrated in FIGS. 7a and 7b.

The backing layer (42) extends in use on a wound over the skin around the wound. On the proximal face of the backing layer (43) on the overlap (44), it bears an adhesive film (45), to attach it to the skin sufficiently to hold the wound dressing in place in a fluid-tight seal around the periphery of the wound-facing face (43) of the wound dressing.

There is one inlet pipe (46) for connection to a fluid supply tube (not shown), which passes through and/or under the wound-facing face (43), and one outlet pipe (47) for connection to a fluid offtake tube (not shown), which passes through and/or under the wound-facing face (43).

Referring to FIGS. 3a and 3b, one form of the dressing is provided with a wound filler (48) under a circular backing layer (42).

This comprises a generally frustroconical, toroidal conformable hollow body, defined by a membrane (49) which is filled with a fluid, here air or nitrogen, that urges it to the wound shape.

The filler (48) may be permanently attached to the backing layer with an adhesive film (not shown) or by heat-sealing.

The inlet pipe (46) and outlet pipe (47) are mounted centrally in the backing layer (42) above the central tunnel (50) of the toroidal hollow body (48) and each passes through the backing layer (42), and each extends in pipes (51) and (52) respectively through the tunnel (50) of the toroidal hollow body (48) and then radially in diametrically opposite directions under the body (48).

This form of the dressing is a more suitable layout for deeper wounds.

Referring to FIGS. 4a and 4b, a more suitable form for shallower wounds is shown. This comprises a circular backing layer (42) and a circular upwardly dished first membrane (61) with apertures (62) that is permanently attached to the backing layer (42) by heat-sealing to form a circular pouch (63).

The pouch (63) communicates with the inlet pipe (46) through a hole (64), and thus effectively forms an inlet pipe manifold that delivers the circulating fluid directly to the wound when the dressing is in use.

An annular second membrane (65) with openings (66) is permanently attached to the backing layer (42) by heat-sealing to form an annular chamber (67) with the layer (42).

The chamber (67) communicates with the outlet pipe (47) through an orifice (68), and thus effectively forms an outlet pipe manifold that collects the fluid directly from the wound when the dressing is in use.

Referring to FIGS. 5a and 5b, a variant of the dressing of FIGS. 4a and 4b that is a more suitable form for deeper wounds is shown.

This comprises a circular backing layer (42) and a filler (69), in the form of an inverted frustroconical, solid integer, here a resilient elastomeric foam, formed of a thermoplastic, or preferably a cross-linked plastics foam.

It may be permanently attached to the backing layer (42), with an adhesive film (not shown) or by heat-sealing.

A circular upwardly dished sheet (70) lies under and conforms to, but is a separate structure, permanently unattached to, the backing layer (42) and the solid integer (69).

A circular upwardly dished first membrane (71) with apertures (72) is permanently attached to the sheet (70) by heat-sealing to form a circular pouch (73) with the sheet (70).

The pouch (73) communicates with the inlet pipe (46) through a hole (74), and thus effectively forms an inlet pipe manifold that delivers the circulating fluid directly to the wound when the dressing is in use.

An annular second membrane (75) with openings (76) is permanently attached to the sheet (70) by heat-sealing to form an annular chamber (77) with the sheet (70).

The chamber (77) communicates with the outlet pipe (47) through an orifice (78), and thus effectively forms an outlet pipe manifold that collects the fluid directly from the wound when the dressing is in use.

Alternatively, where appropriate the dressing may be provided in a form in which the circular upwardly dished sheet (70) functions as the backing layer and the solid filler (69) sits on the sheet (70) as the backing layer, rather than under it. The filler (69) is held in place with an adhesive film or tape, instead of the backing layer (42).

Referring to FIGS. 6a and 6b, a dressing that is a more suitable form for deeper wounds is shown.

This comprises a circular backing layer (42) and a filler (79), in the form of an inverted generally hemispherical integer, here a resilient elastomeric foam or a hollow body filled with a fluid, here a gel that urges it to the wound shape, and permanently attached to the backing layer with an adhesive film (not shown) or by heat-sealing.

The inlet pipe (46) and outlet pipe (47) are mounted peripherally in the backing layer (42).

A circular upwardly dished sheet (80) lies under and conforms to, but is a separate structure, permanently unattached to, the backing layer (42) and the filler (79).

A circular upwardly dished bilaminate membrane (81) has a closed channel (82) between its laminar components, with
perforations (83) along its length on the outer surface (84) of the dish formed by the membrane (81) and
an opening (85) at the outer end of its spiral helix, through which the channel (82) communicates with the inlet pipe (46),
and thus effectively forms an inlet pipe manifold that delivers the circulating fluid directly to the wound when the dressing is in use.

The membrane (81) also has apertures (86) between and along the length of the turns of the channel (82).

The inner surface (87) of the dish formed by the membrane (81) is permanently attached at its innermost points (88) with an adhesive film (not shown) or by heat-sealing to the sheet (80). This defines a mating closed spirohelical conduit (89).

At the outermost end of its spiral helix, the conduit (89) communicates through an opening (90) with the outlet pipe (47) and is thus effectively an outlet manifold to collect the fluid directly from the wound via the apertures (86).

Referring to FIGS. 7a and 7b, one form of the dressing is provided with a circular backing layer (42). A first (larger) inverted hemispherical membrane (92) is permanently attached centrally to the layer (42) by heat-sealing to form a hemispherical chamber (94) with the layer (42). A second (smaller) concentric hemispherical membrane (93) within the first is permanently attached to the layer (42) by heat-sealing to form a hemispherical pouch (95). The pouch (95) communicates with the inlet pipe (46) and is thus effectively an inlet manifold, from which pipes (97) radiate hemispherically and run to the wound bed to end in apertures (98). The pipes (97) deliver the circulating fluid directly to the wound bed via the apertures (98).

The chamber (94) communicates with the outlet pipe (47) and is thus effectively an outlet manifold from which tubules (99) radiate hemispherically and run to the wound bed to end in openings (100). The tubules (99) collect the fluid directly from the wound via the openings (100).

Referring to FIGS. 8a to 8d, one form of the dressing is provided with a square backing layer (42) and
first tube (101) extending from the inlet pipe (46), and
second tube (102) extending from the outlet pipe (47)
at the points at which they pass through the backing layer, to run over the wound bed.

These pipes (101), (102) have a blind bore with orifices (103), (104) along the pipes (101), (102). These pipes (101), (102) respectively form an inlet pipe or outlet pipe manifold that delivers the circulating fluid directly to the wound bed or collects the fluid directly from the wound respectively via the orifices. FIG. 8 includes four views illustrated in FIGS. 8a, 8b, 8c, and 8d.

Figure 8A:
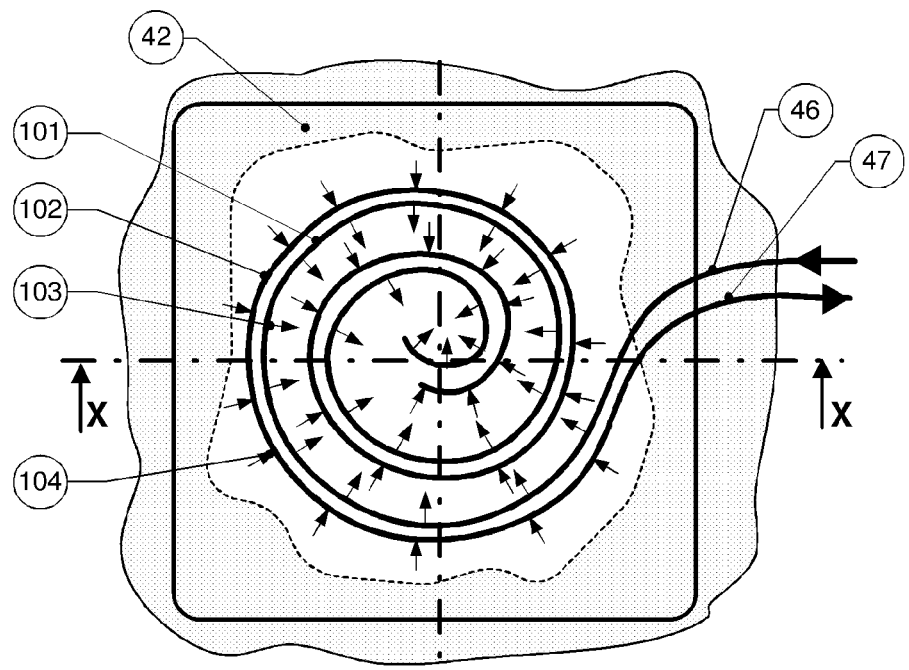
Figure 8B:
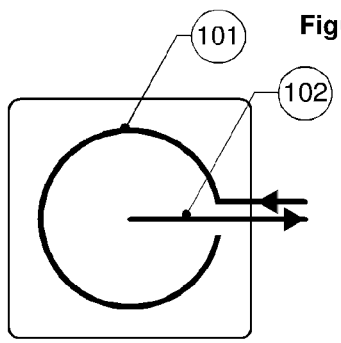
Figure 8C:
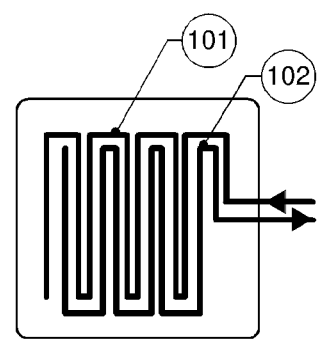
Figure 8D:
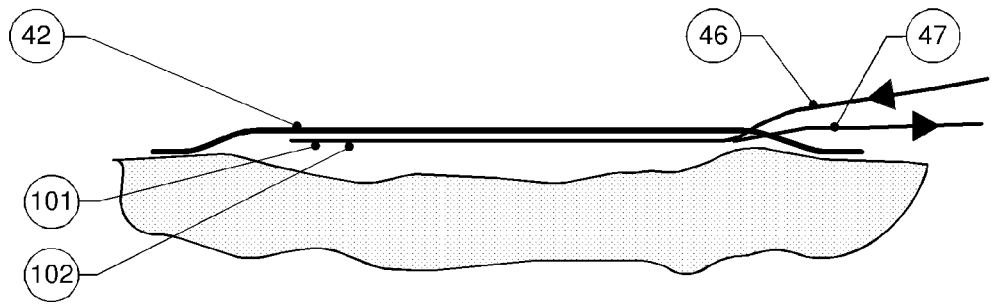

In FIGS. 8a and 8d, one layout of each of the pipes (101), (102) as inlet pipe and outlet pipe manifolds is a spiral.

In FIG. 8b, the layout is a variant of that of FIGS. 8a and 8b, with the layout of the inlet manifold (101) being a full or partial torus, and the outlet manifold (102) being a radial pipe.

Referring to FIG. 8c, there is shown another suitable layout in which the inlet manifold (101) and the outlet manifold (102) run alongside each other over the wound bed in a boustrophedic pattern, i.e. in the manner of ploughed furrows.

Referring to FIGS. 9a to 9d, there are shown other suitable layouts for deeper wounds, which are the same as shown in FIGS. 8a to 8d. FIG. 9 includes two views illustrated in FIGS. 9a and 9b. The square backing layer (42) however has a wound filler (110) under, and may be permanently attached to, the backing layer (42), with an adhesive film (not shown) or by heat-sealing, which is an inverted hemispherical solid integer, here a resilient elastomeric foam, formed of a thermoplastic, preferably a cross-linked plastics foam.

Under the latter is a circular upwardly dished sheet (111) which conforms to, but is a separate structure, permanently unattached to, the solid filler (110). Through the sheet (111) pass the inlet pipe (46) and the outlet pipe (47), to run over the wound bed. These pipes (101), (102) again have a blind bore with orifices (103), (104) along the pipes (101), (102).

Alternatively (as in FIGS. 5a and 5b), where appropriate the dressing may be provided in a form in which the circular upwardly dished sheet (111) functions as the backing layer and the solid filler (110) sits on the sheet (42) as the backing layer, rather than under it. The filler (110) is held in place with an adhesive film or tape, instead of the backing layer (42).

In FIGS. 10a to 10c, inlet and outlet manifolds for the wound dressings for respectively delivering fluid to, and collecting fluid from, the wound, are formed by slots in and apertures through layers permanently attached to each other in a stack. FIG. 10 includes three views illustrated in FIGS. 10a, 10b, and 10c.

Thus, in FIG. 10a there is shown an exploded isometric view of an inlet manifold and outlet manifold stack (120) of five square coterminous thermoplastic polymer layers, being first to fifth layers (121) to (125), each attached with an adhesive film (not shown) or by heat-sealing to the adjacent layer in the stack (120).

The topmost (first) layer (121) (which is the most distal in the dressing in use) is a blank square capping layer.

The next (second) layer (122), shown in FIG. 10b out of the manifold stack (120), is a square layer, with an inlet manifold slot (126) through it. The slot (126) runs to one edge (127) of the layer (122) for connection to a mating end of a fluid inlet tube ((not shown), and spreads into four adjacent branches (128) in a parallel array with spaces therebetween.

The next (third) layer (123) is another square layer, with inlet manifold apertures (129) through the layer (123) in an array such that the apertures (129) are in register with the inlet manifold slot (126) through the second layer (122) (shown in FIG. 10b).

The next (fourth) layer (124), shown in FIG. 10c out of the manifold stack (120), is another square layer, with inlet manifold apertures (130) through the layer (124) in an array such that the apertures (130) are in register with the apertures (129) through the third layer (123).

It also has an outlet manifold slot (131) through it.

The slot (131) runs to one edge (132) of the layer (124) on the opposite side of the manifold stack (120) from the edge (127) of the layer (122), for connection to a mating end of a fluid outlet tube (not shown).

It spreads into three adjacent branches (133) in a parallel array in the spaces between the apertures (130) in the layer (124) and in register with the spaces between the apertures (129) in the layer (122).

The final (fifth) layer (125) is another square layer, with inlet manifold apertures (134) through the layer (125) in an array such that the apertures (134) are in register with the inlet manifold apertures (130) through the fourth layer (124) (in turn in register with the apertures (129) through the third layer (123). It also has outlet manifold apertures (135) in the layer (125) in an array such that the apertures (135) are in register with the outlet manifold slot (131) in the fourth layer (124).

It will be seen that, when the layers (121) to (125) are attached together to form the stack (120), the topmost (first) layer (121), the inlet manifold slot (126) through the second layer (122), and the third layer (123) cooperate to form an inlet manifold in the second layer (122), which is in use is connected to a mating end of a fluid inlet tube (not shown).

The inlet manifold slot (126) through the second layer (122), and the inlet manifold apertures (129), (130) and (134) through the layers (123), (124) and (125), all being mutually in register, cooperate to form inlet manifold conduits though the third to fifth layers (123), (124) and (125) between the inlet manifold in the second layer (122) and the proximal face (136) of the stack (120).

The third layer (121), the outlet manifold slot (131) through the fourth layer (124), and the fifth layer (125) cooperate to form an outlet manifold in the fourth layer (124), which is in use is connected to a mating end of a fluid outlet tube (not shown).

The outlet manifold slot (131) through the fourth layer (124), and the outlet manifold apertures (135) through the fifth layer (125), being mutually in register, cooperate to form outlet manifold conduits though the fifth layer (125) between the outlet manifold in the fourth layer (124) and the proximal face (136) of the stack (120).

Referring to FIG. 11, the apparatus (1) for aspirating, irrigating and/or cleansing wounds is a variant of the apparatus (1) of FIG. 1.

It has bypass (711) around the pump (17), as a protection of the pump against any blockage in the system.

It is activated automatically by appropriate means, e.g. it is normally blocked by a bursting disc (not shown), or a pressure-activated motorised valve. An alternative to the by-pass (711) is a pressure sensor in the system that will detect excessive load or pressure, and shut down the pump. Referring to FIG. 12, the apparatus (1) for aspirating, irrigating and/or cleansing wounds is a variant of the apparatus (1) of FIG. 2.

The latter is a two-phase system with a dialysis unit (21), but is one in which dialytic fluid passes only once across the surface of the dialytic membrane (28) in the first chamber (25) from a dialysate reservoir (not shown) to waste via a second bleed T-valve (36) into, e.g. a collection bag (not shown).

This variant has a dialysate recirculation tube (811) running between a first T-valve (816) on the inlet side of the dialysate pump (23) and a second T-valve (817) to permit the pump (23) to recirculate the dialysate once the circuit is primed in multiple passes through the dialysis unit (21).

Figure 14:
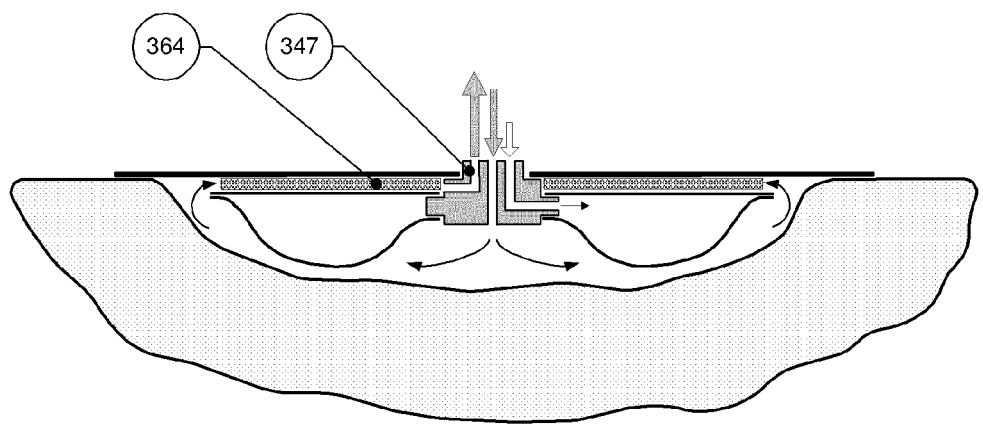
Figure 15:
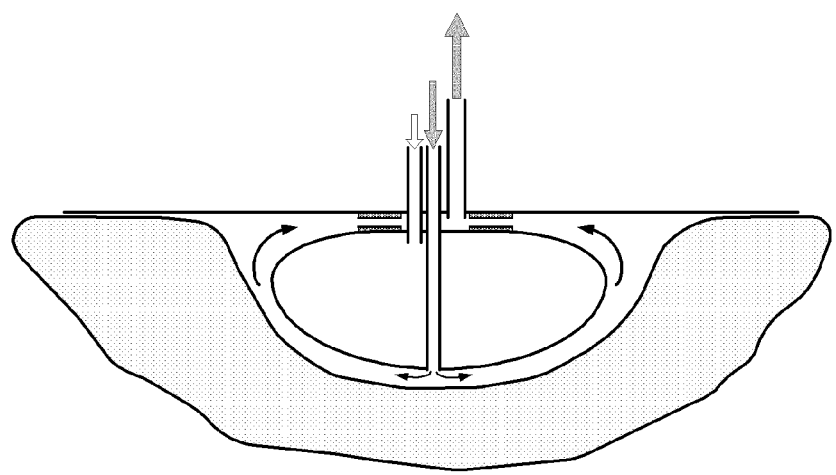

The operation of the system will be apparent to the skilled person. Referring to FIGS. 13 to 15, these forms of the dressing are provided with a wound filler (348) under a circular backing layer (342).

This comprises respectively a generally downwardly domed or toroidal, or oblately spheroidal conformable hollow body, defined by a membrane (349) which is filled with a fluid, here air or nitrogen, that urges it to the wound shape.

The filler (348) is permanently attached to the backing layer via a boss (351), which is e.g. heat-sealed to the backing layer (342).

An inflation inlet pipe (350), inlet pipe (346) and outlet pipe (347) are mounted centrally in the boss (351) in the backing layer (342) above the hollow body (348). The inflation inlet pipe (350) communicates with the interior of the hollow body (348), to permit inflation of the body (348). The inlet pipe (346) extends in a pipe (352) effectively through the hollow body (348). The outlet pipe (347) extends radially immediately under the backing layer (342).

In FIG. 13, the pipe (352) communicates with an inlet manifold (353), formed by a membrane (361) with apertures (362) that is permanently attached to the filler (348) by heat-sealing. It is filled with foam (363) formed of a suitable material, e.g. a resilient thermoplastic. Preferred materials include reticulated filtration polyurethane foams with small apertures or pores. FIG. 13 includes two views illustrated in FIGS. 13a and 13b.

In FIG. 14, the outlet pipe (347) communicates with a layer of foam (364) formed of a suitable material, e.g. a resilient thermoplastic. Again, preferred materials include reticulated filtration polyurethane foams with small apertures or pores.

In all of FIGS. 13, 14 and 15, in use, the pipe (346) ends in one or more openings that deliver the irrigant fluid directly from the wound bed over an extended area.

Similarly, the outlet pipe (347) effectively collects the fluid radially from the wound periphery when the dressing is in use.

Referring to FIG. 16, the dressing is also provided with a wound filler (348) under a circular backing layer (342). FIG. 16 includes two views illustrated in FIGS. 16a and 16b.

This also comprises a generally toroidal conformable hollow body, defined by a membrane (349) which is filled with a fluid, here air or nitrogen, that urges it to the wound shape.

The filler (348) may be permanently attached to the backing layer (342) via a first boss (351) and a layer of foam (364) formed of a suitable material, e.g. a resilient thermoplastic. Again, preferred materials include reticulated filtration polyurethane foams with small apertures or pores.

The first boss (351) and foam layer (364) are respectively heat-sealed to the backing layer (342) and the boss (351).

An inflation inlet pipe (350), inlet pipe (346) and outlet pipe (347) are mounted centrally in the first boss (351) in the backing layer (342) above the toroidal hollow body (348).

The inflation inlet pipe (350), inlet pipe (346) and outlet pipe (347) respectively each extend in a pipe (353), (354) and (355) through a central tunnel (356) in the hollow body (348) to a second boss (357) attached to the toroidal hollow body (348).

The pipe (353) communicates with the interior of the hollow body (348), to permit inflation of the body (348). The pipe (354) extends radially through the second boss (357) to communicate with an inlet manifold (352), formed by a membrane (361) that is permanently attached to the filler (348) by heat-sealing in the form of a reticulated honeycomb with openings (362) that deliver the irrigant fluid directly to the wound bed over an extended area. The pipe (355) collects the fluid flowing radially from the wound centre when the dressing is in use.

This form of the dressing is a more suitable layout for deeper wounds

Figure 17:
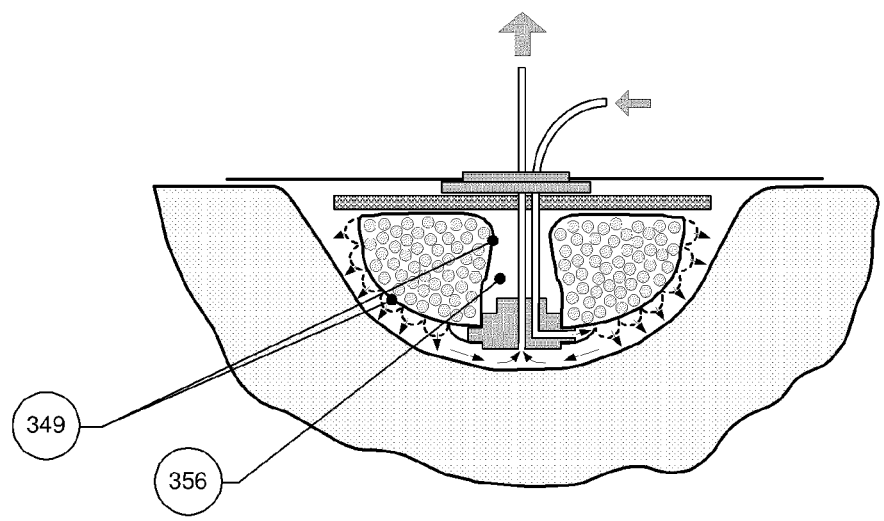

In FIG. 17, the dressing is similar to that of FIG. 16, except that the toroidal conformable hollow body, defined by a membrane (349), is filled with a fluid, here a solid particulates, such as plastics crumbs or beads, rather than a gas, such as air or an inert gas, such as nitrogen or argon, and the inflation inlet pipe (350) and pipe (353) are omitted from the central tunnel (356).

Examples of contents for the body (348) also include gels, such as silicone gels or preferably cellulosic gels, for example hydrophilic cross-linked cellulosic gels, such as Intrasite™ cross-linked materials. Examples also include aerosol foams, and set aerosol foams, e.g. CaviCarer™ foam.

Figure 19:
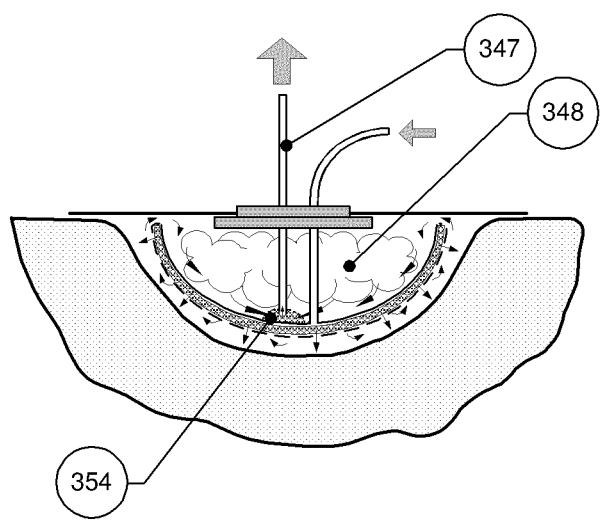

Referring to FIGS. 18 and 19, another form for deeper wounds is shown. FIG. 18 includes two views illustrated in FIGS. 18a and 18b. This comprises a circular backing layer (342) and a chamber (363) in the form of a deeply indented disc much like a multiple Maltese cross or a stylised rose.

This is defined by an upper impervious membrane (361) and a lower porous film (362) with apertures (364) that deliver the irrigant fluid directly from the wound bed over an extended area. A number of configurations of the chamber (363) are shown, all of which are able to conform well to the wound bed by the arms closing in and possibly overlapping in insertion into the wound.

In a particular design of the chamber (363), shown lowermost, on of the arms extended and provided with an inlet port at the end of the extended arm. This provides the opportunity for coupling and decoupling the irrigant supply remote from the dressing and the wound in use.

An inlet pipe (346) and outlet pipe (347) are mounted centrally in a boss (351) in the backing layer (342) above the chamber (363). The inlet pipe (346) is permanently attached to, and communicate with the interior of, the chamber (363), which thus effectively forms an inlet manifold. The space above the chamber (363) is filled with a loose gauze packing (364).

In FIG. 18, the outlet pipe (347) collects the fluid from the interior of the dressing from just under the wound-facing face (343) of the backing layer (342).

A variant of the dressing of FIG. 18 is shown in FIG. 19. The outlet pipe (347) is mounted to open at the lowest point of the space above the chamber (363) into a piece of foam (374).

Figure 20:
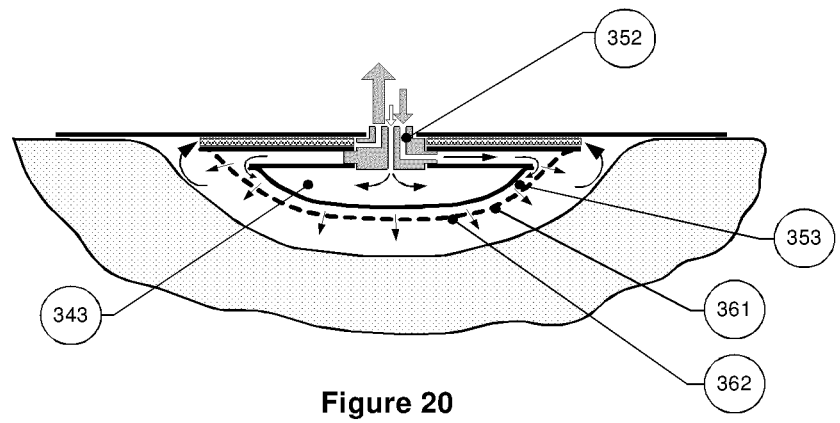

In FIG. 20, the dressing is similar to that of FIG. 13, except that the inlet pipe (352) communicates with an inlet manifold (353), formed by a membrane (361) with apertures (362), over the upper surface of the generally downwardly domed wound hollow filler (348), rather than through it.

Figure 22:
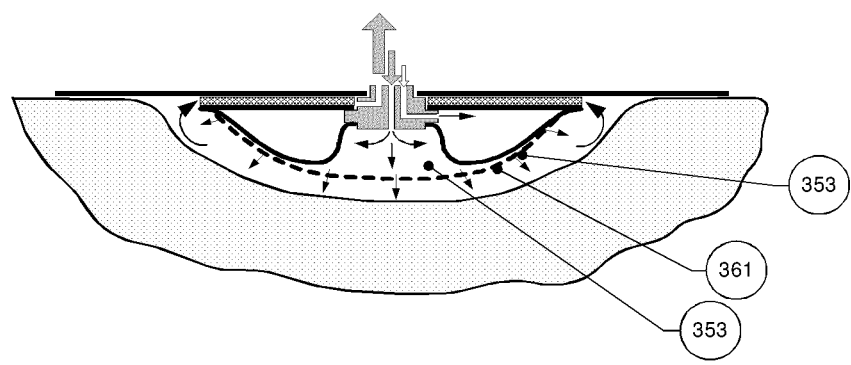

In FIG. 22, the dressing is similar to that of FIG. 14, with the addition of an inlet manifold (353), formed by a membrane (361) with apertures (362), over the lower surface of the generally downwardly domed annular wound hollow filler.

Figure 21:
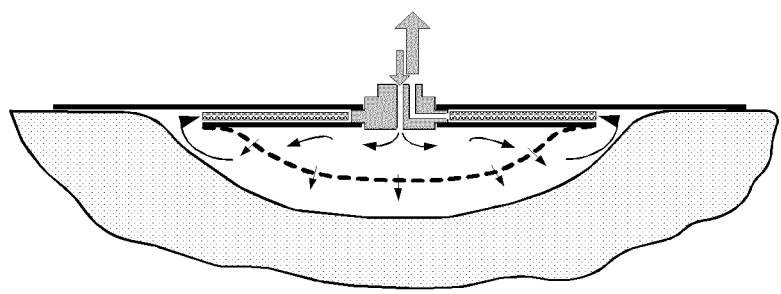

In FIG. 21, the generally downwardly domed annular wound hollow filler is omitted.

Figure 23:
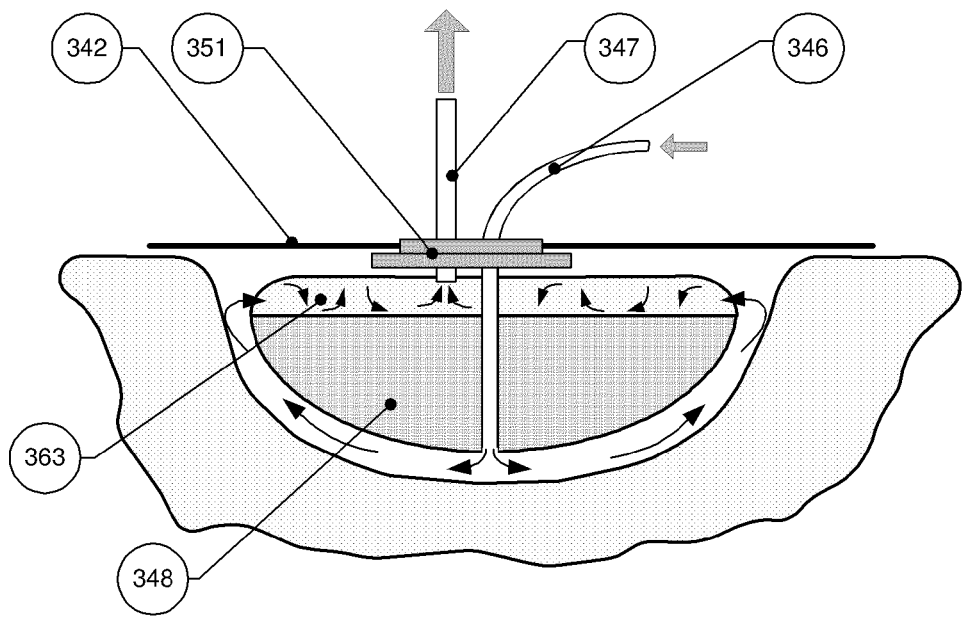

Referring to FIG. 23, another form for deeper wounds is shown. An inlet pipe (346) and outlet pipe (347) are mounted centrally in a boss (351) in the backing layer (342) above a sealed-off foam filler (348). The inlet pipe (346) is permanently attached to and passes through the filler (348) to the wound bed. The outlet pipe (347) is attached to and communicates with the interior of, a chamber (363) defined by a porous foam attached to the upper periphery of the filler (348). The chamber (363) thus effectively forms an outlet manifold.

Figure 24:
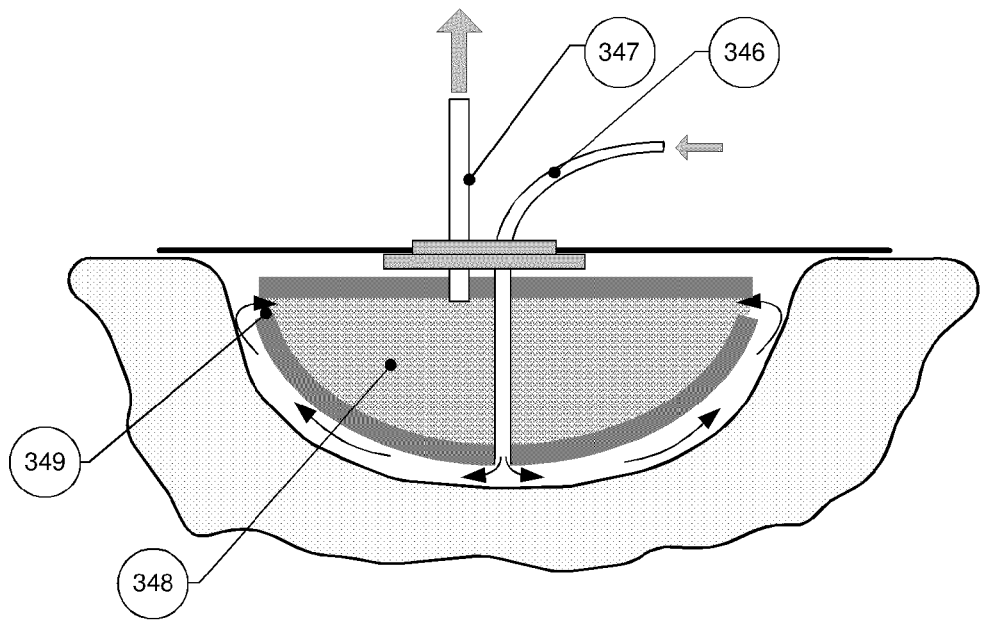

In FIG. 24, the foam filler (348) is only partially sealed-off. The inlet pipe (346) is permanently attached to and passes through the filler (348) to the wound bed. The outlet pipe (347) is attached to and communicates with the interior of the foam of the filler (348). Fluid passes into an annular gap (349) near the upper periphery of the filler (348) into the foam, which thus effectively forms an outlet manifold.

Figure 25:
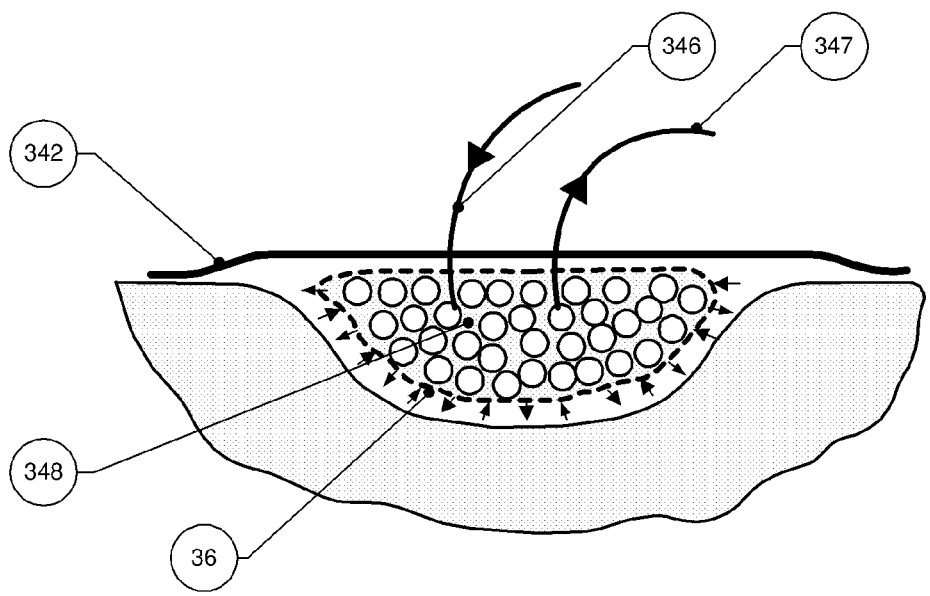
Figure 26:
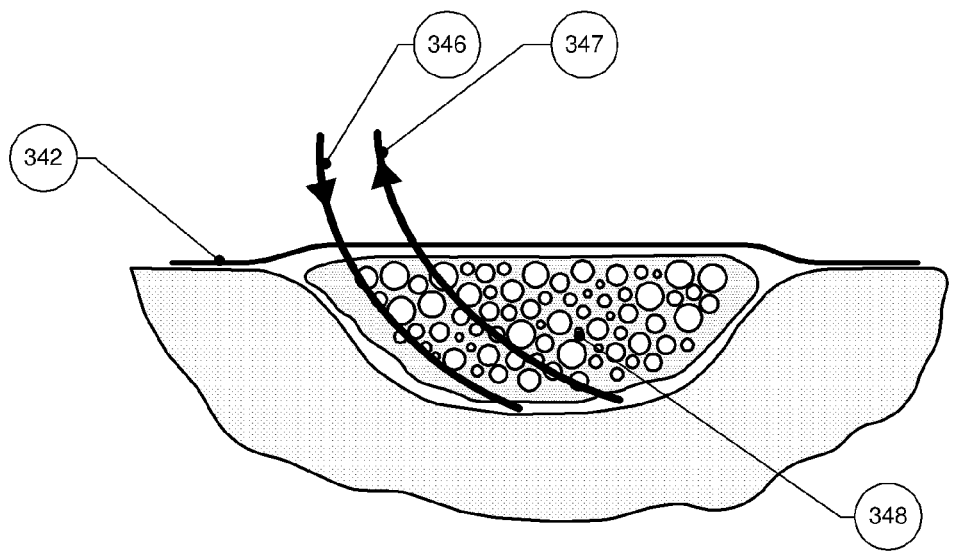

FIGS. 25 and 26 show dressings in which the inlet pipe (346) and outlet pipe (347) pass through the backing layer (342).

In FIG. 25, they communicates with the interior of a porous bag filler (348) defined by a porous film (369) and filled with elastically resilient plastics bead or crumb.

In FIG. 26, they communicate with the wound space just below a foam filler (348). The foam (348) may CaviCare™ foam, injected and formed in situ around the pipes (346) and (347).

Referring to FIG. 27, the apparatus (1) for aspirating, irrigating and/or cleansing wounds is a major a variant of the apparatus shown in FIG. 1.

The device for moving fluid through the wound and means for fluid cleansing (17) in FIG. 1 is a peristaltic pump (18), e.g. preferably a small portable peristaltic pump, acting on the fluid circulation tube (13) downstream of the dressing (2) to apply a low negative pressure on the wound.

In the apparatus (1) shown in FIG. 27, the peristaltic pump (18) is replaced by:
a) a peristaltic pump, acting on the fluid supply tube (7) upstream of the dressing (2), and
b) a vacuum pump assembly with pressure regulating means, acting on the fluid circulation tube (13) downstream of the dressing (2),
to apply a low negative pressure on the wound.

The vacuum pump assembly comprises a tank (911) with
an inlet tube (912) connecting to the fluid circulation tube (13) and communicating with the upper part of the tank (911),
a waste tube (913) connecting to a waste pump (914) with waste bag (915) and communicating with the lower part of the tank (911),
a pump tube (916) connecting to a vacuum pump (918) and communicating with the upper part of the tank (911), and
an outlet tube (917) connecting to the fluid circulation tube (13) to the means for cleansing (17) and communicating with the lower part of the tank (911).

The vacuum pump (918) is controlled by a pressure feedback regulator (919) through an electrical line (920), the regulator receiving signals from a tank sensor (921) in the upper part of the tank (911), and a dressing sensor (922) in the wound space respectively via lines (923) and (924).

The operation of the apparatus (1) is similar to that of the apparatus in FIG. 1 mutatis mutandis.

The pressure feedback regulator (919) regulates the pressure at the wound and/or the tank (911).

If the amount of fluid in circulation becomes excessive, e.g. because the wound continues to exude heavily, the waste pump (914) may be started to transfer fluid from the lower part of the tank (911) to the waste bag (915).

The use of the apparatus of the present invention will now be described by way of example only in the following Examples:

Example 1

Microfiltration Removal of Bioburden, Including Micro-Organisms from a Single-Phase System A single phase circuit essentially as in FIG. 1, but with a sample port S1 between the wound dressing and the pump and a sample port S2 downstream of a sterile 0.22 .mu.m filter filtration device as the cleansing means was sterilised by γ-irradiation Prior to inoculation with the test organism (*S aureus* NCTC 10788), the wound reservoir was filled with 45 ml sterile MRD (maximum recovery diluent) and then the MRD was inoculated with the test organism to give a final concentration of $10^4$ cfu/ml.

The culture was allowed to pre-circulate around the circuit (bypassing the sterile 0.22 μm filter) prior to being circulated through the filtration device. A sample (0.5 ml) of the pre-circulation fluid was taken from port S1 at 30 and 60 minutes. This was serially diluted in MRD to $10^{-3}$ and duplicate 1 ml tryptone soya agar (TSA) plates were repared from each dilution according to a standard validated protocol. Plates were incubated for at least 72 hours at 32° C. prior to counting.

After 1 hour, the fluid was allowed to circulate through the filtration device. 0.5 ml samples of the circulating fluid were taken from ports S1 at T=10, 30, 50 and 70 minutes and S2 at T=0, 20, 40, 60 and 80 minutes. All samples were enumerated as described above.

Results

TABLE 1

Bacterial counts of pre-circulation fluid taken from the single phase system

| Sample time (minutes) | Mean count (cfu/ml) | $Log_{10}$ count (cfu/ml) |
| --- | --- | --- |
| 30 | $2.31 \times 10^4$ | 4.36 |
| 60 | $1.87 \times 10^4$ | 4.27 |

TABLE 2

Bacterial counts of post-wound reservoir (port S1) fluid taken from the single phase Exudialysis system

| Sample time (minutes) | Mean count (cfu/ml) | $Log_{10}$ count (cfu/ml) |
| --- | --- | --- |
| 10 | $6.30 \times 10^3$ | 3.80 |
| 30 | $4.10 \times 10^3$ | 3.61 |
| 50 | $1.77 \times 10^3$ | 3.25 |
| 70 | $1.23 \times 10^3$ | 3.09 |

TABLE 3

Bacterial counts of post-filtration (port S2) fluid taken from the single phase Exudialysis system

| Sample time (minutes) | Mean count (cfu/ml) | $Log_{10}$ count (cfu/ml) |
| --- | --- | --- |
| 0 | $<1.0 \times 10^1$ | <1.00 |
| 20 | $<1.0 \times 10^1$ | <1.00 |
| 40 | $<1.0 \times 10^1$ | <1.00 |
| 60 | $1.0 \times 10^1$ | 1.00 |
| 80 | $<1.0 \times 10^1$ | <1.00 |

Conclusions

The single phase system was able to immediately remove bacterial cells from the wound circuit after passing through 0.22 .mu.m filter by approximately 3 logs and cause a gradual reduction in the overall numbers of circulating bacteria.

Example 2

Inhibition of Elastase in a Two-Phase System (Static Second Phase)

a) Preparation of an Immobilised Elastase Antagonist—a Conjugate ('the Inhibitor') of 4-(2-aminoethyl)-benzene-sulfonyl fluoride (AEBSF) with poly(maleic anhydride-alt-methylvinylether), and with 1% 5-(2-aminoethylamino)-1-naphthalenesulfonic acid (EDANS) Fluorescent Tag To a magnetically stirred solution of MAMVE (1.646 g, 10.5 mmol units) in DMF (100 ml) was added EDANS (30.4 mg, 0.1 mmol) in DMF (2 ml). After 15 minutes, a solution of AEBSF hydrochloride (2.502 g, 10.4 mmol) and triethylamine (1.056 g, 10.4 mmol) in DMF (20 ml) was added dropwise. After 5 h, this solution was precipitated dropwise into 0.5 M HCl (2000 ml), Buchner filtered and washed with 0.5 M HCl. The product was vacuum desiccated to dryness and stored at −4° C. Yield 3.702 g, 98%.

To a magnetically stirred solution of MAMVE (2.000 g, 12.8 mmol units) in DMF (100 ml) was added EDANS (37.0 mg, 0.1 mmol) in DMF (2 ml). After 15 minutes, a solution of phenethylamine (1.537 g, 12.7 mmol) in DMF (10 ml) was added dropwise. After 5 h, this solution was precipitated dropwise into 0.5 M HCl (2000 ml), Buchner filtered and washed with 0.5 M HCl. The product was vacuum desiccated to dryness and stored at room temperature.

Yield 3.426 g, 97%.

b) Elastase Inhibition

A two-phase circuit essentially as in FIG. 1 was used, with a two-phase cleansing means with static second phase, but with a sample port downstream of a cleansing means.

The cleansing means is a MiCroKros Cross Flow Syringe Filter (Spectrum Labs Inc) PS/400K MWCO 8 cm$^2$, with two separate chambers, any fluid in the outer being held static.

The outer chamber was filled with 2 mg/ml Inhibitor solution (~1 ml in TRIS) and connected up to the tubing. The inlet and outlet tubing was placed in a TRIS solution and TRIS was flushed through the inner chamber of the MiCoKros syringe and the tubing for 5 mins. The tubing was then emptied. 2 ml of elastase (0.311 mg/ml) was pipetted into the wound circuit.

The tubes were placed in the reservoir and the pump and the timer were started simultaneously.

10 microliter samples were taken every hour from the wound circuit for six hours and assayed in the following way immediately after sampling. A control of static elastase was assayed at every time point in order to determine the decrease in activity over the 6 hours.

c) Elastase Activity Assay

The elastase substrate N-Succ-(Ala)$_3$-nitronilide was prepared (10 mg/ml in DMSO). 25 microliter of the N-Succ-(Ala)$_3$-nitronilide (10 mg/ml) was added to 2.475 ml of TRIS in a 4.5 ml capacity disposable cuvette. This mixing was completed 10 mins before the elastase solution was due to be added into the cuvettes (in order to ensure the substrate was mixed well). The 10 microliter sample was then added to each cuvette and mixed well. The sample was incubated at room temp for 40 mins and the absorbance at 405 nm recorded.

Results and Conclusions

TABLE 1

The absorbance detected after 40 mins incubation (405 nm) for elastase + TRIS. The experiment was repeated in triplicate and control of static elastase was recorded every hour.

| Time/h | TRIS Run 1 | Run 2 | Run 3 | Elastase control |
|---|---|---|---|---|
| 0 | 0.266 | 0.284 | | |
| 1 | 0.255 | 0.258 | 0.239 | 0.283 |
| 2 | 0.271 | 0.242 | 0.225 | 0.284 |
| 3 | 0.219 | 0.218 | 0.209 | 0.291 |
| 4 | 0.208 | 0.203 | 0.203 | 0.277 |
| 5 | 0.197 | 0.17 | 0.194 | 0.304 |
| 6 | 0.198 | 0.161 | 0.182 | 0.288 |
| elastase final | 0.267 | 0.289 | 0.281 | |

TABLE 2

The absorbance detected after 40 mins incubation (405 nm) for elastase + MAMVE-AEBSF. The experiment was repeated in triplicate and control of static elastase was recorded every hour. The average of all the elastase control experiments was used to calculate the 100 % activity for 0 h.

| Time/h | MAMVE-AEBSF Run 1 | Run 2 | Run 3 | Elastase control |
|---|---|---|---|---|
| 0 | 0.362 | 0.39 | 0.371 | |
| 1 | 0.234 | 0.308 | 0.267 | 0.4 |
| 2 | 0.158 | 0.215 | 0.193 | 0.374 |
| 3 | 0.081 | 0.161 | 0.128 | 0.363 |
| 4 | 0.064 | 0.12 | 0.083 | 0.366 |
| 5 | 0.046 | 0.073 | 0.048 | 0.375 |
| 6 | 0.025 | 0.061 | 0.034 | 0.348 |

The average of all the elastase control experiments was used to calculate the 100% activity for 0 h.

TABLE 3

The average % elastase activity for 3 variables, with the SD

| % Average | | | SD | | |
|---|---|---|---|---|---|
| Time/h | TRIS | AEBSF | Time/h | TRIS | AEBSF |
| 0 | 100.00 | 100.00 | 0 | | |
| 1 | 88.55 | 72.47 | 1 | 3.61 | 9.96 |
| 2 | 86.90 | 50.70 | 2 | 8.22 | 7.73 |
| 3 | 76.07 | 33.14 | 3 | 1.95 | 10.80 |
| 4 | 72.30 | 23.92 | 4 | 1.02 | 7.65 |
| 5 | 66.06 | 14.96 | 5 | 5.23 | 4.04 |
| 6 | 63.70 | 10.75 | 6 | 6.55 | 5.03 |

The results indicate that for the elastase+Tris solution there is a 60-70% drop in activity. This can be explained as a dilution effect as the 2 ml of elastase mix with the 1 ml TRIS in the outer chamber (2/3). This indicates that the system is inert to elastase and the complete mixing/diffusion across the membrane occurs within 3 h.

The elastase+MAMVE-AEBSF within the 6 h shows a 90% drop in elastase activity.

Example 3

Sequestration of Iron Ions from a Two-Phase System (Static Second Phase)

A two-phase circuit essentially as in FIG. 1 was used, with a two-phase cleansing means with static second phase, but with a sample port downstream of a cleansing means, the latter being a Slide-A-Lyzer dialysis cassette (Pierce, 10,000 MWCO, 3-15 ml capacity, Product #66410) in a chamber of a Slide-A-Lyzer.

The cassette was loaded with one of the following:
a) 5 ml of phosphate buffer saline (PBS),
b) starch control (40, 120 and 200 mg/ml) or
c) starch-desferrioxamine (DFO) conjugate (supplied by Biomedical Frontiers Inc.) in solution (40, 120 and 200 mg/ml).

Each dialysis cassette was placed in a Slide-A-Lyzer chamber. In this arrangement, the cassette load is separated from the recirculating first fluid by the 10,000 MWCO membrane referred to above.

Transferrin (10 mg/ml, 35 ml volume) was injected into the sample port and circulated around the flow system by a Masterflex pump (Model No. 7523-37) at different flow rates (0.54, 0.82, 1.08 and 1.35 ml/min) for 8 hours.

Samples were collected at 0, 2, 4, 6 and 8 hours.

The iron content of the samples was measured using a ferrozine assay as follows: The sample was mixed with 50 mM acetate buffer, pH 4.8 to liberate iron from transferrin. Ascorbate (30 mM) was added to the sample to reduce released Fe (III) ions to Fe (II) ions. Ferrozine (5 mM) was mixed with the sample forming a coloured complex with Fe (II) ion. The absorbance was measured using UNICAM UV4-100 UV-Vis spectrophotometer V3.32 (serial no. 022405).

Results and Conclusions

Starch-DFO picked up iron from transferrin in a dose dependent manner over 8 hours. Approximately 20-25% iron removal occurred in the presence of 200 mg/ml of starch-DFO after 8 hours recirculation.

In the presence of different concentrations of starch control or PBS the iron content of transferrin dropped slightly due to a dilution effect but then slowly returned to normal, suggesting that iron pick-up by starch-DFO was mediated by DFO alone.

The iron pick-up profile for transferrin was similar at different flow rates suggesting that flow had no effect on iron transfer across the dialysis membrane.

Example 4

Infusion of Antibiotic from the Second Phase of a Two-Phase System (Moving Second Phase)

A two-phase circulation system essentially as in FIG. 1 with the second (dialysate) circuit essentially as in FIG. 2 was used. The pumps were peristaltic acting on silicone tubing. The second circuit was provided with a reservoir of dialysate with which to modify the wound fluid (50 ml Falcon centrifuge tube). The wound circuit was connected into the ends of a luer-fitting hollow fibre tangential membrane dialysis unit (Spectrum® MicroKros® X14S-100-04N, 8 cm2 surface area, 400 KD Mol. Wt. cut off,). The dialysate circuit was connected to the side ports of the same dialysis unit so that flow between the wound circuit and the dialysate circuit were in a counter current direction.

The wound circuit was flushed first with ethanol and then with sterile water as per the manufacturers' instruction. The wound reservoir was filled with 20 ml of sterile water. The wound pump was run at a speed setting of 100, which generated a measured flow rate of 2.09 $ml^{-1}$ in the wound circuit. The dialysate circuit was flushed first with ethanol and then with sterile water as per the manufacturers instruction. The dialysate reservoir was filled with 20 ml of sterile water. The dialysate pump was run at a speed setting of 100, which generated a measured flow rate of 1.93 ml $min^{-1}$ in the dialysate circuit. Samples (1 ml) were removed from the wound and the dialysate reservoirs by means of a length of silicone tube with a luer fitting attached to a 2 ml syringe At the start of the experiment, 5 ml of sterile water was removed from the dialysate reservoir and 5 ml of a 5 mg $ml^{-1}$ solution of gentamycin sulphate was added (EP standard gentamycin sulphate, CRS; (activity 616 IU $mg^{-1}$)). Both the wound and the dialysate pumps were started at the same time. Samples were removed from the dialysate circuit and the wound circuit at intervals over 230 minutes. No volumes were replaced during the experiment.

Samples (1 ml) were diluted with 2 ml of sterile water and the UV absorbance at 190 nm was checked to get an approximate measure of the movement of gentamycin from the dialysate circuit to the wound circuit using a previously generated standard curve.

Samples were subsequently analysed with a quantitative zone of inhibition assay for gentamycin activity according to an assay that uses *Staphylococcus epidermidis* as the indicator bacteria.

Results and Conclusions

The results of the antimicrobial activity-zone of inhibition assays of the fluid show that the level of gentamycin in the wound circuit increases steadily over 230 min with the rate of increase slowing as the levels of drug in the two circuits approach each other. The gentamycin levels in the dialysate circuit show a steady decrease as expected if drug is moving from the dialysate circuit to the wound circuit. At the pressure and flow rates useful in clinical practice, drugs for wound healing can be delivered in acceptable quantities and on an acceptable timescale.

Example 5

Regeneration of Glutathione (Reduction of Oxidised Glutathione (GSSG) to Glutathione (GSH) by Localised Glutathione Reductase (GR) and Cofactor NADP (Reduced Form) in a Two-Phase System (Static Second Phase)

A two-phase circuit essentially as in FIG. 1 was used, with a two-phase cleansing means with static second phase, but with a sample port downstream of a cleansing means, the latter being a Slide-A-Lyzer dialysis cassette (Pierce, 10,000 MWCO, 3-15 ml capacity, Product #66410) in a chamber of a Slide-A-Lyzer.

Into the internal cavity of separate 15 ml capacity Slide-A-Lyzer cassettes was injected 5 ml of each stock solution:
a) 2 mg/ml NADP prepared in distilled water (NADP)
b) 2 mg/ml Glutathione reductase prepared in NADP stock solution (GR+NADP)
c) 2 mg/ml Glutathione reductase prepared in distilled water (GR) in triplicate.

The cassettes were laid flat and into the upper, outer cavity was aliquoted 15 ml of GSSG stock solution (50 microM GSSG prepared in distilled water (30.6 mg/l). This was circulated around the first phase circuit. The latter was sampled (1 ml) every hour for 6 h in total into 1.5 ml capacity disposable UV cuvettes. At the end of this period, each aliquot was assayed using a Glutathione Assay Kit (from Calbiochem). Triplicates were averaged and SD determined for each data point. These data were plotted as GSSG concentration versus time for each of the three control systems.

Results & Conclusions

GSSG was depleted by the combination of GR and its cofactor NADP to a significantly greater extent than by GR or NADP alone. Thus depletion is not attributable to non-specific binding. Approximately 40% of GSSG was depleted in 6 h at the stated enzyme and cofactor concentrations.

Example 6

Degradative Removal of Bacterial Autoinducers from a Single-Phase System

The exchange of extra cellular signalling molecules called auto-inducers is used by bacteria and is essential to the co-ordination of the expression of key bacterial virulence genes activated at a critical bacterial cell density, and thus to achieving successful bacterial colonization and invasion of tissue. The system is called Quorum Sensing. Conversely, (usually enzymic) degradation or sequestration of the autoinducer species is one way to disrupt the essential communication and aid the prevention of infection in wounds.

The AiiA enzyme is a degrader of the 3-oxododecylhomoserine lactone signal molecule which is used by *S. aureus* as an autoinducer.

The AiiA enzyme used is one produced at the University of Nottingham and is bound to a maltose binding protein.

a) Preparation of AiiA Enzyme Bound to a Polymer Support

Cyanogen bromide activated Sepharose 6 MB (from Sigma) (200-300 μm diameter for a higher through-flow rate) were washed in 1 mM hydrochloric acid and allowed to soak and swell for a period of 30 minutes. The gel was washed with multiple volumes of distilled water and then with $NaHCO_3$/NaCl pH 8.5 and used immediately.

The AiiA enzyme solution (approx. 1 mg/ml) was added to the polymer support beads and allowed to stand at 4° C. overnight. The coupled beads were washed with pH 8.5

NaHCO$_3$/NaCl and stored as a slurry. The washings from the beads were also collected in order to determine the amount of uncoupled enzyme and hence the coupling efficiency.

Blank, uncoupled beads were used as a control.

Different amounts of the enzyme coupled beads, 1 mg, 10 mg and 100 mg, are trapped in a chamber defined by two glass frits across a cylindrical glass cylinder with axial inlet and outlet ports for throughflow, which formed the cleansing means in a single phase system, which also has a sample port downstream of a cleansing means. A 10 microM stock of 3-oxododecylhomoserine lactone (ODHSL) is pumped through the chamber at 1.93 ml min$^{-1}$ and 37° C. for 6 hr.

The circulating fluid is sampled (1 ml) every hour for 6 h in total into 1.5 ml capacity disposable UV cuvettes.

At the end of this period, each aliquot was assayed using the assay of Swift et al. 1997, J. Bacteriol. 179: 5271-5281, which uses bioluminescence-based plasmid reporter systems in E. coli. The 100 mg sample shows an 86% reduction in ODHSL concentration in 6 hours.

What is claimed is:

1. An apparatus for treating a wound, comprising:
   a wound dressing comprising:
      a backing layer configured to form a closure over the wound; and
      an irrigation system, the irrigation system comprising:
         a spiral tube member comprising an elongated tubular body extending along a length, wherein the elongated tubular body curves around a center point constantly receding from and circling the center point; and
         a plurality of apertures along the length of the spiral tube member wherein the spiral tube member is configured to deliver circulating fluid directly to the wound through the plurality of apertures along its length.

2. The apparatus of claim 1, further comprising an outlet tube configured to connect to the backing layer and draw fluid away from the wound.

3. The apparatus of claim 2, wherein the outlet tube is configured to be mounted to the backing layer at an opening in the backing layer.

4. The apparatus of claim 3, wherein the outlet tube is configured to provide fluid communication between a vacuum pump and the wound dressing.

5. The apparatus of claim 1, wherein the backing layer comprises an adhesive on a periphery of the backing layer, wherein the adhesive is configured to attach the backing layer to skin around the wound.

6. The apparatus of claim 1, further comprising:
   a membrane layer comprising a plurality of apertures configured to contact the wound; and
   a wound filler.

7. The apparatus of claim 6, wherein a periphery of the backing layer extends beyond and surrounds the membrane layer.

8. The apparatus of claim 1, further comprising a vacuum pump configured to apply negative pressure to the wound dressing.

9. The apparatus of claim 1, further comprising a collection container in fluid communication with the wound dressing and configured to store fluid removed from the wound.

10. The apparatus of claim 9, further comprising a pressure sensor to detect pressure in the collection canister.

11. The apparatus of claim 1, further comprising a reservoir configured to be in fluid communication with the wound dressing and to store fluid to be provided to the wound through the irrigation system.

12. The apparatus of claim 11, wherein the fluid stored in the reservoir comprises medicated fluids.

13. The apparatus of claim 1, further comprising a controller configured to control a vacuum pump.

14. The apparatus of claim 1, further comprising a pressure sensor to detect pressure in the wound.

15. A method of treating a wound, comprising:
   applying a wound dressing over a wound comprising:
      a backing layer configured to form a closure over the wound; and
      an irrigation system, the irrigation system comprising:
         a spiral tube member comprising an elongated tubular body extending along a length, wherein the elongated tubular body curves around a center point constantly receding from and circling the center point; and
         a plurality of apertures along the length of the spiral tube member;
   delivering fluid to the wound through the plurality of apertures of the irrigation system; and
   applying negative pressure to at least the wound dressing to facilitate removal of fluid from the wound.

16. The method of claim 15, further comprising drawing fluid away from the wound with a fluid offtake tube connected to the backing layer.

17. The method of claim 16, wherein fluid drawn away from the wound is stored in a collection canister.

18. The method of claim 15, further comprising detecting a pressure in the wound with a pressure sensor at the wound.

19. The method of claim 15, wherein the wound dressing is applied to skin around the wound with an adhesive.

20. The method of claim 15, further comprising delivering medicated fluid to the wound through the plurality of apertures of the irrigation system.

* * * * *